(12) United States Patent
Wiley

(10) Patent No.: US 10,323,276 B2
(45) Date of Patent: *Jun. 18, 2019

(54) ADAPTIVE IMMUNITY PROFILING AND METHODS FOR GENERATION OF MONOCLONAL ANTIBODIES

(71) Applicant: ADAPTIVE BIOTECHNOLOGIES CORPORATION, Seattle, WA (US)

(72) Inventor: Steven R. Wiley, Seattle, WA (US)

(73) Assignee: ADAPTIVE BIOTECHNOLOGIES CORPORATION, Seattle, WA (US)

( * ) Notice: Subject to any disclaimer, the term of this patent is extended or adjusted under 35 U.S.C. 154(b) by 901 days.

This patent is subject to a terminal disclaimer.

(21) Appl. No.: 14/174,767

(22) Filed: Feb. 6, 2014

(65) Prior Publication Data

US 2014/0155277 A1 Jun. 5, 2014

Related U.S. Application Data

(63) Continuation of application No. 13/144,645, filed as application No. PCT/US2010/021264 on Jan. 15, 2010, now Pat. No. 8,685,898.

(60) Provisional application No. 61/145,039, filed on Jan. 15, 2009.

(51) Int. Cl.

| C40B 50/06 | (2006.01) |
| C12Q 1/6874 | (2018.01) |
| C07K 16/20 | (2006.01) |
| C12N 15/10 | (2006.01) |

(52) U.S. Cl.
CPC .......... *C12Q 1/6874* (2013.01); *C07K 16/205* (2013.01); *C12N 15/1034* (2013.01); *C40B 50/06* (2013.01); *C12N 15/1072* (2013.01)

(58) Field of Classification Search
None
See application file for complete search history.

(56) References Cited

U.S. PATENT DOCUMENTS

| 3,270,960 A | 9/1966 | Phillips |
| 3,773,919 A | 11/1973 | Boswell et al. |
| 4,474,754 A | 10/1984 | Shimizu et al. |
| 4,683,195 A | 7/1987 | Mullis et al. |
| 4,683,202 A | 7/1987 | Mullis |
| 4,751,188 A | 6/1988 | Valet |
| 4,800,159 A | 1/1989 | Mullis et al. |
| 4,876,189 A | 10/1989 | Schetters |
| 4,942,124 A | 7/1990 | Church |
| 4,965,188 A | 10/1990 | Mullis et al. |

(Continued)

FOREIGN PATENT DOCUMENTS

| CN | 101225441 A | 7/2008 |
| CN | 102272327 A | 12/2011 |

(Continued)

OTHER PUBLICATIONS

US 8,642,750 B2, 02/2014, Faham et al. (withdrawn)

(Continued)

*Primary Examiner* — Christian C Boesen
(74) *Attorney, Agent, or Firm* — Cooley LLP

(57) ABSTRACT

Methods are provided for producing monoclonal antibody candidates using adaptive immunity profiling. In some aspects, the method provides for the use of massively parallel signature sequencing.

9 Claims, 6 Drawing Sheets

(56) References Cited

U.S. PATENT DOCUMENTS

| | | |
|---|---|---|
| 5,075,217 A | 12/1991 | Weber |
| 5,126,022 A | 6/1992 | Soane et al. |
| 5,149,625 A | 9/1992 | Church et al. |
| 5,168,038 A | 12/1992 | Tecott et al. |
| 5,189,147 A | 2/1993 | Saito et al. |
| 5,210,015 A | 5/1993 | Gelfand et al. |
| 5,213,960 A | 5/1993 | Chang |
| 5,231,012 A | 7/1993 | Mosmann et al. |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,364,759 A | 11/1994 | Caskey et al. |
| 5,399,491 A | 3/1995 | Kacian et al. |
| 5,418,134 A | 5/1995 | Morley |
| 5,449,752 A | 9/1995 | Fujii et al. |
| 5,498,392 A | 3/1996 | Wilding et al. |
| 5,506,126 A | 4/1996 | Seed et al. |
| 5,587,128 A | 12/1996 | Wilding et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,698,396 A | 12/1997 | Pfreundschuh |
| 5,699,798 A | 12/1997 | Hochman et al. |
| 5,741,676 A | 4/1998 | Dunn |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,854,033 A | 12/1998 | Lizardi |
| 5,858,195 A | 1/1999 | Ramsey |
| 5,925,517 A | 7/1999 | Tyagi et al. |
| 5,935,793 A | 8/1999 | Wong |
| 5,969,108 A | 10/1999 | McCafferty et al. |
| 5,981,176 A | 11/1999 | Wallace |
| 5,981,179 A | 11/1999 | Lorinez et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,087,096 A | 7/2000 | Dau et al. |
| 6,090,592 A | 7/2000 | Adams et al. |
| 6,091,000 A | 7/2000 | Haynes |
| 6,143,496 A | 11/2000 | Brown et al. |
| 6,172,214 B1 | 1/2001 | Brenner |
| 6,174,670 B1 | 1/2001 | Wittwer et al. |
| 6,228,589 B1 * | 5/2001 | Brenner ............ C07H 21/00 435/6.11 |
| 6,258,540 B1 | 7/2001 | Lo et al. |
| 6,258,568 B1 | 7/2001 | Nyren |
| 6,291,183 B1 | 9/2001 | Pirrung et al. |
| 6,300,070 B1 | 10/2001 | Boles et al. |
| 6,312,690 B1 | 11/2001 | Edelman et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,605,272 B2 | 8/2003 | Novak et al. |
| 6,613,525 B2 | 9/2003 | Nelson et al. |
| 6,667,159 B1 | 12/2003 | Walt |
| 6,753,147 B2 | 6/2004 | Vogelstein et al. |
| 6,787,308 B2 | 9/2004 | Balasubramanian et al. |
| 6,794,499 B2 | 9/2004 | Wengel et al. |
| 6,806,079 B1 | 10/2004 | McCafferty et al. |
| 6,858,412 B2 | 2/2005 | Willis et al. |
| 6,919,434 B1 | 7/2005 | Goto et al. |
| 6,948,850 B2 | 11/2005 | Bevilacqua |
| 6,964,850 B2 | 11/2005 | Bevilacqua |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,323,306 B2 | 1/2008 | Dunn et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,709,197 B2 | 5/2010 | Drmanac |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,955,794 B2 | 6/2011 | Shen et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | MacEvicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,685,898 B2 | 4/2014 | Wiley |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,217,176 B2 | 12/2015 | Faham et al. |
| 9,228,232 B2 | 1/2016 | Faham et al. |
| 9,279,159 B2 | 3/2016 | Robins et al. |
| 9,371,558 B2 | 6/2016 | Robins et al. |
| 9,394,567 B2 | 7/2016 | Asbury et al. |

(56) References Cited

U.S. PATENT DOCUMENTS

| | | |
|---|---|---|
| 9,416,420 B2 | 8/2016 | Faham et al. |
| 9,506,119 B2 | 11/2016 | Faham et al. |
| 9,512,487 B2 | 12/2016 | Faham et al. |
| 9,708,657 B2 | 7/2017 | Asbury et al. |
| 9,809,813 B2 | 11/2017 | Robins et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0018489 A1 | 1/2004 | Ma et al. |
| 2004/0033490 A1 | 2/2004 | Laird et al. |
| 2004/0121364 A1 | 6/2004 | Chee et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | MacEvicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0275752 A1 | 7/2006 | Sindhi |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0233802 A1 | 9/2009 | Bignell et al. |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0129874 A1 | 5/2010 | Mitra et al. |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0323355 A1 | 12/2010 | Dittmer |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0166034 A1 | 7/2011 | Kwong et al. |
| 2011/0183863 A1 | 7/2011 | Wagner et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0010096 A1 | 1/2012 | Wohlgemuth et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2012/0308999 A1 | 12/2012 | Sarma et al. |
| 2013/0005584 A1 | 1/2013 | Faham |
| 2013/0017957 A1 | 1/2013 | Faham et al. |
| 2013/0045221 A1 | 2/2013 | Stauss et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0137108 A1 | 5/2013 | Tripathi et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0273647 A1 | 10/2013 | Sahin et al. |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0065629 A1 | 3/2014 | Barken et al. |
| 2014/0094376 A1 | 4/2014 | Han |
| 2014/0127699 A1 | 5/2014 | Han |
| 2014/0141982 A1 | 5/2014 | Jacobson et al. |
| 2014/0186848 A1 | 7/2014 | Robins et al. |

(56) References Cited

U.S. PATENT DOCUMENTS

| | | |
|---|---|---|
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0227705 A1 | 8/2014 | Vogelstein et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |
| 2015/0017630 A1 | 1/2015 | Oved et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0087535 A1 | 3/2015 | Patel et al. |
| 2015/0133317 A1 | 5/2015 | Robinson et al. |
| 2015/0154352 A1 | 6/2015 | Johnson et al. |
| 2015/0167080 A1 | 6/2015 | Moorhead et al. |
| 2015/0203897 A1 | 7/2015 | Robins et al. |
| 2015/0215062 A1 | 7/2015 | Li et al. |
| 2015/0218656 A1 | 8/2015 | Kirsch et al. |
| 2015/0232936 A1 | 8/2015 | Shoemaker et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0275308 A1 | 10/2015 | Carlton et al. |
| 2015/0299785 A1 | 10/2015 | Livingston et al. |
| 2015/0299786 A1 | 10/2015 | Robins et al. |
| 2015/0299800 A1 | 10/2015 | Faham et al. |
| 2016/0115532 A1 | 4/2016 | Faham |
| 2016/0138011 A1 | 5/2016 | Dewitt et al. |
| 2016/0186260 A1 | 6/2016 | Klinger et al. |
| 2016/0201133 A1 | 7/2016 | Faham et al. |
| 2016/0251721 A1 | 9/2016 | Robins et al. |
| 2016/0251728 A1 | 9/2016 | Faham et al. |
| 2016/0258025 A1 | 9/2016 | Klinger et al. |
| 2016/0304956 A1 | 10/2016 | Robins et al. |
| 2016/0319340 A1 | 11/2016 | Robins et al. |
| 2017/0037469 A1 | 2/2017 | Robins et al. |
| 2017/0292149 A1 | 10/2017 | Emerson et al. |
| 2017/0335386 A1 | 11/2017 | Livingston et al. |
| 2017/0335390 A1 | 11/2017 | Asbury et al. |
| 2017/0335391 A1 | 11/2017 | Emerson et al. |
| 2017/0349954 A1 | 12/2017 | Faham et al. |
| 2018/0037953 A1 | 2/2018 | Emerson et al. |
| 2018/0073015 A1 | 3/2018 | Robins et al. |
| 2018/0080090 A1 | 3/2018 | Faham et al. |
| 2018/0087109 A1 | 3/2018 | Klinger et al. |
| 2018/0112278 A1 | 4/2018 | Faham et al. |
| 2018/0312832 A1 | 11/2018 | Robins et al. |
| 2018/0355429 A1 | 12/2018 | Klinger et al. |

FOREIGN PATENT DOCUMENTS

| | | | |
|---|---|---|---|
| CN | 103097888 A | 5/2013 | |
| EA | 007958 B1 | 2/2007 | |
| EP | 0303459 A2 | 2/1989 | |
| EP | 0799897 A1 | 10/1997 | |
| EP | 1516929 A2 | 3/2005 | |
| EP | 1544308 A1 | 6/2005 | |
| EP | 1549764 B1 | 7/2005 | |
| EP | 0972081 B1 | 6/2007 | |
| EP | 1544308 B1 | 1/2009 | |
| EP | 2062982 A1 | 5/2009 | |
| EP | 2088205 A1 | 8/2009 | |
| EP | 2088432 A1 | 8/2009 | |
| EP | 2418287 A2 | 2/2012 | |
| EP | 2364368 B1 | 1/2014 | |
| JP | 4262799 A | 9/1992 | |
| JP | 2002-503954 A | 2/2001 | |
| JP | 2005-245381 A | 9/2005 | |
| JP | 2006-501842 A | 1/2006 | |
| JP | 2007-515955 A | 6/2007 | |
| JP | 2007-536939 A | 12/2007 | |
| JP | 2008-099588 A | 5/2008 | |
| JP | 2011-505123 A | 2/2011 | |
| JP | 2012-508011 A | 4/2012 | |
| JP | 2013-524848 A | 6/2013 | |
| JP | 2013-524849 A | 6/2013 | |
| WO | WO 1993/001838 A1 | 2/1993 | |
| WO | WO 2005/059176 A1 | 6/1995 | |
| WO | WO 1995/028481 A1 | 10/1995 | |
| WO | WO 1997/013868 A1 | 4/1997 | |
| WO | WO 1997/013877 A1 | 4/1997 | |
| WO | WO 1997/018330 A1 | 5/1997 | |
| WO | WO 1997/046706 A1 | 12/1997 | |
| WO | WO 1998/001738 A2 | 1/1998 | |
| WO | WO 1998/044151 A1 | 10/1998 | |
| WO | WO 1999/019717 A1 | 4/1999 | |
| WO | WO 1999/020798 A1 | 4/1999 | |
| WO | WO 2001/014424 A2 * | 3/2001 | ............. C07K 16/00 |
| WO | WO 2002/024322 A2 | 3/2002 | |
| WO | WO 2003/008624 A2 | 1/2003 | |
| WO | WO 2003/044225 A2 | 5/2003 | |
| WO | WO 2003/052101 A1 | 6/2003 | |
| WO | WO 2003/059155 A2 | 7/2003 | |
| WO | WO 2004/003820 A2 | 1/2004 | |
| WO | WO 2004/033728 A2 | 4/2004 | |
| WO | WO 2004/034031 A2 | 4/2004 | |
| WO | WO 2004/044209 A1 | 5/2004 | |
| WO | WO 2004/046098 A2 | 6/2004 | |
| WO | WO 2004/063706 A2 | 7/2004 | |
| WO | WO 2004/096985 A2 | 11/2004 | |
| WO | WO 2005/003375 A2 | 1/2005 | |
| WO | WO 2005/005651 A2 | 1/2005 | |
| WO | WO 2005/010200 A2 | 2/2005 | |
| WO | WO 2005/042774 A2 | 5/2005 | |
| WO | WO 2005/053603 A2 | 6/2005 | |
| WO | WO 2005/056828 A1 | 6/2005 | |
| WO | WO 2005/084134 A2 | 9/2005 | |
| WO | WO 2005/111242 A2 | 11/2005 | |
| WO | WO 2005/113803 A1 | 12/2005 | |
| WO | WO 2006/076025 A2 | 7/2006 | |
| WO | WO 2006/076205 A2 | 7/2006 | |
| WO | WO 2006/110855 A2 | 10/2006 | |
| WO | WO 2006/116155 A2 | 11/2006 | |
| WO | WO 2006/138284 A2 | 12/2006 | |
| WO | WO 2007/008759 A2 | 1/2007 | |
| WO | WO 2007/134220 A2 | 11/2007 | |
| WO | WO 2008/026927 A2 | 3/2008 | |
| WO | WO 2008/039694 A2 | 4/2008 | |
| WO | WO 2008/108803 A2 | 9/2008 | |
| WO | WO 2008/147879 A1 | 12/2008 | |
| WO | WO 2009/015296 A1 | 1/2009 | |
| WO | WO 2009/017678 A2 | 2/2009 | |
| WO | WO 2009/019657 A2 | 2/2009 | |
| WO | WO 2009/021215 A1 | 2/2009 | |
| WO | WO 2009/045898 A2 | 4/2009 | |
| WO | WO 2009/070767 A2 | 6/2009 | |
| WO | WO 2009/095567 A2 | 8/2009 | |
| WO | WO 2009/108860 A2 | 9/2009 | |
| WO | WO 2009/108866 A2 | 9/2009 | |
| WO | WO 2009/137255 A2 | 11/2009 | |
| WO | WO 2009/137832 A2 | 11/2009 | |
| WO | WO 2009/145925 A1 | 12/2009 | |
| WO | WO 2009/151628 A2 | 12/2009 | |
| WO | WO 2009/152928 A2 | 12/2009 | |

(56) References Cited

FOREIGN PATENT DOCUMENTS

| | | |
|---|---|---|
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A1 | 5/2010 |
| WO | WO 2010/083456 A1 | 7/2010 |
| WO | WO 2010/151416 A1 | 12/2010 |
| WO | WO 2011/017151 A2 | 2/2011 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/012703 A2 | 1/2012 |
| WO | WO 2012/017081 A1 | 2/2012 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/122484 A1 | 9/2012 |
| WO | WO 2012/142213 A2 | 10/2012 |
| WO | WO 2012/148497 A2 | 11/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/123442 A1 | 8/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2014/145992 A1 | 9/2014 |
| WO | WO 2015/002908 A1 | 1/2015 |
| WO | WO 2015/013461 A2 | 1/2015 |
| WO | WO 2015/058159 A1 | 4/2015 |
| WO | WO 2015/106161 A1 | 7/2015 |
| WO | WO 2015/134787 A2 | 9/2015 |
| WO | WO 2015/153788 A1 | 10/2015 |
| WO | WO 2015/160439 A2 | 10/2015 |
| WO | WO 2016/069886 A1 | 5/2016 |
| WO | WO 2016/138122 A1 | 9/2016 |
| WO | WO 2016/161273 A1 | 10/2016 |

OTHER PUBLICATIONS

Duenas et al. (1996) Immunology vol. 89 pp. 1 to 7.*
Lorimer et al 1995 Nucleic Acids Research vol. 23 pp. 3067 to 3068.*
Tam (1998) PNAS USA vol. 85 pp. 5409 to 5413.*
Ohlin et al. (1996) Molecular Immunology vol. 33 pp. 47 to 56.*
Chinese Application No. 201380042163.X, Search Report dated Apr. 12, 2016 (English translation), 2 pages.
European Patent Application No. 13828563.0, Extended European Search Report dated Feb. 12, 2016, 10 pages.
European Patent Application No. 13757482.8, Extended European Search Report dated Jun. 6, 2016, 5 pages.
PCT/US2015/058035, International Search Report and Written Opinion dated Jan. 29, 2016, 14 pages.
Akatsuka, Y. et al., "Rapid screening of T-cell receptor (TCR) variable gene usage by multiplex PCR: Application for assessment of clonal composition", *Tissue Antigens*, 53:122-134 (1999).
Al-Lazikani, B. et al., "Standard Conformations for the Canonical Structures of Immunoglobulins," *J. Mol. Biol.*, 273:927-948 (1997).
Alexandre, D. et al. "*H. sapiens* rearranged T-cell receptor gamma chain gene, V2-JP1", GenBank accession No. X57737, NCBI, Nov. 14, 2006, 8 pages. [online] [retrieved on Jun. 26, 2013] Retrieved from the internet <URL:http://www.ncbi.nlm.nih.gov/nuccore/x57737>.
Alexandre, D. et al. "*H. sapiens* rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Arstila, T.P., et al., "A direct estimate of the human $\alpha\beta$ T cell receptor diversity," *Science*, 286(5441):958-961 (1999).
Bahloul, M. et al., "Clinical impact of molecular diagnostics in low-grade lymphoma," *Best Practice & Research Clinical Haematology*, 18(1):97-111 (2005).
Benichou, J. et al., "Rep-Seq: uncovering the immunological repertoire through next-generation sequencing", *Immunology*, 135(3):183-191 (2012).
Bernardin, F. et al., "Estimate of the total Number of CD8+ clonal expansions in healthy adults using a new DNA heteroduplex-tracking assay for CDR3 repertoire analysis", *Journal of Immunological Methods*, 274(1-2):159-175 (2003).
Berquam-Vrieze, K. et al., "Cell of origin strongly influences genetic selection in a mouse model of T-ALL", *Blood*, 118:4646-4656 (2011).
Blow, N., "PCR's next frontier," *Nature Methods*, 4(10):869-875 (2007).
Bolotin, D.A. et al., "Next generation sequencing for TCR repertoire profiling: Platform-specific features and correction algorithms", *Eur. J. Immunol.*, 42:3073-3083 (2012).
Bonarius, H.P.J. et al., "Monitoring the T-Cell Receptor Repertoire at Single-Clone Resolution", *PLoS One*, 1(e55):1-10 (2006).
Boyd, S.D. et al., Individual Variation in the Germline Ig Gene Repertoire Inferred from Variable Region Gene Rearrangements, *The Journal of Immunology*, 184(12):6986-6992 (2010).
Boyd, S.D. et al., "Measurement and Clinical Monitoring of Human Lymphocyte Clonality by Massively Parallel V-D-J Pyrosequencing," *Science Translational Medicine*, 1:12ra23, 40 pages, Supplementary Materials (2009).
Bradfield, S.M. et al., "Graft-versus-leukemia effect in acute lymphoblastic leukemia: the importance of tumor burden and early detection," *Leukemia*,18:1156-1158 (2004).
Brenan, C. et al., "High throughput, nanoliter quantitative PCR," *Drug Discovery Today: Technologies*, 2(3):247-253 (2005).
Buck, G.A. et al., "Design Strategies and Performance of Custom DNA Sequencing Primers", *Biotechniques*, 27(3):528-536 (1999).
Butkus, B., "Hutch Team Uses ddPCR to Quantify T-Cell Response in Tumors; Adaptive Biotech Eyes Market", *PCR Insider*, Dec. 12, 2013, 3 pages http://www.genomeweb.com/print/1323296.
Campana, D., "Progress of Minimal Residual Disease Studies in Childhood Acute Leukemia," *Curr Hematol Malig Rep*, 5:169-176 (2010).
Caporaso, J.G. et al., "Global patterns of 16S rRNA diversity at a depth of millions of sequences per sample", *PNAS*, 108(Suppl. 1):4516-4522 (2010).
Carlson, C.S. et al., "Using synthetic templates to design an unbiased multiplex PCR assay", *Nature Communications*, 4:2680, pp. 1-9 (2013).

(56) References Cited

OTHER PUBLICATIONS

Cavé, H. et al., "Clinical Significance of minimal residual disease in childhood acute lymphoblastic leukemia," *The New England Journal of Medicine*, 339:591-598 (1998).
Chen, Y. et al., "T-cell receptor gene expression in tumour-infiltrating lymphocytes and peripheral blood lymphocytes of patients with nasopharyngeal carcinoma", *British Journal of Cancer*, 72(1):117-22 (1995).
Chothia, C. et al., "Canonical structures for the hypervariable regions of immunoglobulins," *J. Mol. Biol.*, 196:901-917, Abstract only (1987).
Chothia, C. et al., "Conformations of immunoglobulin hypervariable regions," *Nature*, 342:877-883 (1989).
Ciudad, J. et al., "Detection of abnormalities in B-cell differentiation pattern is a useful tool to predict relapse in precursor-B-ALL," *British Journal of Haematology*, 104:695-705 (1999).
Coustan-Smith, E. et al., "Clinical importance of minimal residual disease in childhood acute lymphoblastic leukemia," *Blood*, 96(8):2691-2696 (2000).
Coustan-Smith, E. et al., "Early T-cell precursor leukaemia: a subtype of very high-risk acute lymphoblastic leukaemia," *Lancet Oncology*, 10:147-156 (2009).
Coustan-Smith, E. et al., "Prognostic importance of measuring early clearance of leukemic cells by flow cytometry in childhood acute lymphoblastic leukemia", *Blood*, 100(1):52-58 (2002).
Curran-Everett, D., "Multiple comparisons: philosophies and illustrations", *Am J Physiol Regulatory Integrative Comp Physiol.*, 279:R1-R8 (2000).
Dash, P. et al., "Paired analysis of TCR[alpha] and TCR[beta] chains at the single-cell level in mice", *Journal of Clinical Investigation*, 121(1):288-295 (2011).
De Jonge, H.J.M., et al., "Evidence Based Selection of Housekeeping Genes," *PLoS One*, 9(e989):1-5 (2007).
DeNucci, C.C. et al., "Integrin function in T-cell homing to lymphoid and nonlymphoid sites: getting there and staying there," *Critical Reviews in Immunology*, 29(2):87-109 (2009).
Dheda, K., et al., "Validation of housekeeping genes for normalizing RNA expression in real-time PCR," *Bio Techniques*, 37:112-119 (2004).
Dik, W., et al. "New insights on human T cell development by quantitative T cell receptor gene rearrangement studies and gene expression profiling," *JEM*, 201(11):1715-1723 (2005).
Dobosy, J. et al., "RNase H-dependent PCR (rhPCR): improved specificity and single nucleotide polymorphism detection using blocked cleavable primers," *BMC Biotechnology*, 11(80):1-18 (2011).
Droese, J., et al., "Validation of BIOMED-2 multiplex PCR tubes for detection of TCRB gene rearrangements in T-cell malignancies," *Leukemia*, 18:1531-1538 (2004).
Duby, A.D. et al., "Human T-cell receptor aberrantly rearranged beta-chain J1.5-Dx-J2.1 gene," *PNAS*, GenBank accession No. M13574.1, bases 1 to 100, 4 pages (1986).
Edwards and Gibbs, "Multiplex PCR: advantages, development, and applications," *Genome Research*, 3:S65-S75 (1994).
Elnifro, E.M., et al., "Multiplex PCR: Optimization and Application in Diagnostic Virology", *Clinical Microbiology Reviews*, 13(4):559-570 (2000).
Emerson, R.O. et al., "High-throughput sequencing of T-cell receptors reveals a homogeneous repertoire of tumour-infiltrating lymphocytes in ovarian cancer", *Journal of Pathology*, 231:433-440 (2013).
Faham, M. et al., "Deep-sequencing approach for minimal residual disease detection in acute lymphoblastic leukemia", *Blood*, 120(26):5173-5180 (2012).
Flohr, T., et al., "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", *Leukemia*, 22:771-782 (2008).

Freeman, J.D., et al., "Profiling the T-Cell Receptor Beta-Chain Repertoire by Massively Parallel Sequencing", *Genome Research*, 19(10):1817-1824 (2009).
Gerlinger, M. et al., "Ultra deep T cell receptor sequencing reveals the complexity and intratumour heterogeneity of T cell clones in renal cell carcinomas", *Journal of Pathology*, 231:424-432 (2013).
Gonzalez, S.F., et al., "Trafficking of B Cell Antigen in Lymph Nodes," *Ann. Rev. Immunol.*, 29:215-233 (2011).
Henegariu, O. et al., "Multiplex PCR: Critical Parameters and Step-By-Step Protocol," *Biotechniques*, Informa HealthCare, 23(3):504-511 (1997).
Hodges, E. et al., "Diagnostic role of tests for T cell receptor (TCR) genes", *J Clin Pathol.*, 56(1):1-11 (2003).
Hwang, H.Y. et al., "Identification of a Commonly used CDR3 Region of Infiltrating T Cells Expressing Vβ13 and Vβ15 Derived from Psoriasis Patients", *The Journal of Investigative Dermatology*, 120(3):359-364 (2003).
Jochems and Schlom, "Tumor-infiltrating immune cells and prognosis: the potential link between conventional cancer therapy and immunity," *Experimental Biology and Medicine*, 236:567-579 (2011).
Kalinina, O. et al., "Nanoliter scale PCR with TaqMan detection," *Nucleic Acids Research*, 25(10)1999-2004 (1997).
Kalos, M. et al., "T Cells with Chimeric Antigen Receptors Have Potent Antitumor Effects and Can Establish Memory in Patients with Advanced Leukemia", *Science Translational Medicine*, 3(95ra73):1-11 (2011).
Kaplinski and Remm, "MultiPLX Automatic Grouping and Evaluation of PCR Primers", *Methods in Molecular Biology*, 402(PCR Primer Design):287-303 (2004).
Klarenbeek, P.L. et al., "Human T-cell memory consists mainly of unexpanded clones", *Immunology Letters*, 133:42-48 (2010).
Katz, S.C. et al., "T Cell Infiltrate Predicts Long-Term Survival Following Resection of Colorectal Cancer Liver Metastases," *Ann. Surg. Oncol.*, 16:2524-2530 (2009).
Kehrl, J.H. et al., "Chemoattractant Receptor Signaling and Its Role in Lymphocyte Motility and Trafficking," *Current Topics in Microbiology and Immunology*, 334:107-127 (2009).
Kiianitsa, et al., "Development of Tools for T-Cell Repertoire Analysis (TCRB Spectratyping) for the Canine Model of Hematopoietic Cell Transplantation", *Blood*, ASH—Annual Meeting Abstracts, 110:Abstract 4873, 2 pages (2007).
Kneba, M., et al., "Analysis of Rearranged T-cell Receptor β-Chain Genes by Polymerase Chain Reaction (PCR) DNA Sequencing and Automated High Resolution PCR Fragment Analysis", *Blood*, 86:3930-3937 (1995).
Ladányi, A., et al., "Prognostic impact of B-cell density in cutaneous melanoma", *Cancer Immunol. Immunother*, 60(12):1729-1738 (2011).
Larimore, K., et al., "Shaping of Human Germline IgH Repertoires Revealed by Deep Sequencing," *The Journal of Immunology*, 189(6):3221-3230 (2012).
Ladetto, M. et al., "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).
Ladetto, M. et al., "Real-time polymerase chain reaction in multiple myeloma: Quantitative analysis of tumor contamination of stem cell harvests", *Experimental Hematology*, 30:529-536 (2002).
Logan, A.C. et al., "High-throughput VDJ sequencing for quantification of minimal residual disease in chronic lymphocytic leukemia and immune reconstitution assessment", *PNAS*, 108(52):21194-21199 (2011).
Lowe, T., et al., "A computer program for selection of oligonucleotide primers for polymerase chain reactions," *Nucleic Acids Research*, 18(7):1757-1761 (1990).
Lúcio, P. et al., "Flow cytometric analysis of normal B cell differentiation: a frame of reference for the detection of minimal residual disease in precursor-B-ALL", *Leukemia*, 13:419-427 (1999).
Mahmoud, S.M.A. et al., "Tumor-Infiltrating CD8+ Lymphocytes Predict Clinical Outcome in Breast Cancer", *Journal of Clinical Oncology*, 29(15):1949-1955 (2011).
Marelli-Berg, F.M., et al., "Memory T-cell trafficking: new directions for busy commuters," *Immunology*, 130:158-165 (2010).

(56) References Cited

OTHER PUBLICATIONS

Mariani, S. et al., "Comprehensive assessment of the TCRBV repertoire in small T-cell samples by means of an improved and convenient multiplex PCR method," *Experimental Hematology*, 37(6):728-738 (2009).

Markoulatos, P. et al., "Multiplex Polymerase Chain Reaction: A Practical Approach", *Journal of Clinical Laboratory Analysis*, 16:47-51 (2002).

Maryanski, J.L. et al., "A quantitative, single-cell PCR analysis of an antigen-specific TCR repertoire 8 selected during an in vivo CD8 response: direct evidence for a wide range of clone sizes with uniform tissue distribution", *Molecular Immunology*, 36:745-753 (1999).

Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).

Merriam-Webster, 4 pages (definition of "substantial," accessed Apr. 25, 2014).

Merriam-Webster, 2 pages, (definition of "e.g.," accessed Apr. 25, 2014).

Miqueu, P. et al., "Statistical analysis of CDR3 length distributions for the assessment of T and B cell repertoire biases," *Molecular Immunology*, 44:1057-1064 (2007).

Monod, M.Y. et al., "IMGT/JunctionAnalysis: the first tool for the analysis of the immunoglobulin and T cell receptor complex V-J and V-D-J JUNCTIONs", *Bioinformatics*, 20(Suppl 1):i379-385 (2004).

Slightom, J.L. et al., "*Homo sapiens* germline beta T-cell receptor locus," NCBI Accession No. L36092 NCBI, 254 pages (2009) Retrieved from the Internet: <URL:http://www.ncbi.nlm.nih.gov/nuccore/L36092>.

Nicot, N. et al., "Housekeeping gene selection for real-time RT-PCR normalization in potato during biotic and abiotic stress," Journal of Experimental Botany, 56(421):2907-2914 (2005).

Nolan, T. et al., "Quantification of mRNA using real-time RT-PCR," *Nature Protocols*, 1(3):1559-1582 (2006).

PCT International Search Report and Written Opinion, PCT/US2010/021264, dated Apr. 14, 2010, 7 pages.

PCT International Preliminary Report on Patentability, PCT/US2010/021264, dated Jul. 19, 2011, 5 pages.

PCT International Search Report and Written Opinion for PCT/US2013/040221, dated Sep. 23, 2013, 15 pages.

PCT International Preliminary Report on Patentability, PCT/US2013/040221, dated Apr. 24, 2014, 41 pages.

PCT International Search Report and Written Opinion, PCT/US2010/037477, dated Sep. 24, 2010, 10 pages.

PCT International Preliminary Report on Patentability, PCT/US2010/037477, dated Jan. 4, 2012, 7 pages.

PCT International Search Report and Written Opinion, PCT/US2012/061193, dated Mar. 28, 2013, 13 pages.

PCT International Preliminary Report on Patentability, PCT/US2012/061193, dated Apr. 22, 2014, 8 pages.

PCT International Search Report and Written Opinion, PCT/US2012/068617, dated Mar. 28, 2013, 10 pages.

PCT International Preliminary Report on Patentability, PCT/US2012/068617, dated Jun. 10, 2014, 6 pages.

PCT International Search Report and Written Opinion, PCT/US2013/062925, dated Nov. 25, 2013, 12 pages.

PCT Second Written Opinion for PCT/US2013/062925 dated Jan. 23, 2015, 7 pages.

PCT International Search Report and Written Opinion, PCT/US2011/049012, dated Apr. 10, 2012, 9 pages.

PCT International Preliminary Report on Patentability, PCT/US2011/049012, dated Feb. 26, 2013, 5 pages.

PCT International Search Report and Written Opinion, PCT/US2013/045994, dated Oct. 25, 2013, 15 pages.

PCT International Preliminary Report on Patentability, PCT/US2013/045994, dated Dec. 16, 2014, 10 pages.

PCT International Search Report and Written Opinion, PCT/US2011/026373, dated Oct. 20, 2011, 17 pages.

PCT International Preliminary Report on Patentability, PCT/US2011/026373, dated Aug. 28, 2012, 11 pages.

PCT International Search Report and Written Opinion, PCT/US2014/030859, dated Jul. 18, 2014, 7 pages.

Pekin, D. et al., "Quantitative and sensitive detection of rare mutations using droplet-based microfluidics",*Lab Chip*, 11(3):2156 (2011).

Perkel, J., "Overcoming the Challenges of Multiplex PCR," Biocompare Editorial Article, Oct. 23, 2012, 6 Pages, can be retrieved at URL:http://www.biocompare.com/Editorial-Articles/117895-Multiplex-PCR/>.

Pohl, G. and Shih, "Principle and applications of digital PCR," *Expert Rev. Mol. Diagn.*, 4(1):41-47 (2004).

Puisieux, I. et al., "Oligoclonality of Tumor-Infiltrating Lymphocytes from Human Melanomas," *The Journal of Immunology*, 153:2807-2818 (1994).

Rasmussen, T. et al., Quantitation of minimal residual disease in multiple myeloma using an allele-specific real-time PCR assay, *Experimental Hematology*, 28:1039-1045 (2000).

Reischl and Kochanowski, et al., "Quantitative PCR a Survey of the Present Technology," *Molecular Biotechnology*, 3:55-71 (1995).

Robins, H. et al., "Comprehensive assessment of T-cell receptor β-chain diversity in αβ T cells", *Blood*, 114(19):4099-4107 (2009).

Robins, H.S. et al., "Digital Genomic Quantification of Tumor Infiltrating Lymphocytes", *Science Translational Medicine*, 5:214ra169, 19 pages, Supplementary Materials (2013).

Robins, H. et al., "Detecting and monitoring lymphoma with high-throughput sequencing," *Oncotarget*, 2:287-288 (2011).

Robins, H. et al., "Overlap and Effective Size of the Human CD8+ T Cell Receptor Repertoire", *Science Transitional Medicine*, 2(47, 47ra64):17 pages, Supplemental Materials (2010).

Robins, H. et al., "The Computational Detection of Functional Nucleotide Sequence Motifs in the Coding Regions of Organisms", *Exp Bioi Med*, 233(6):665-73 (2008).

Robins, H., et al., "Ultra-sensitive detection of rare T cell clones", *Journal of Immunological Methods*, 375:14-19 (2012).

Rock, E.P. et al., "CDR3 Length in Antigen-specific Immune Receptors", *J. Exp. Med.*, 179:323-328 (1994).

Rosenberg, S.A. et al., "New Approach to the Adoptive Immunotherapy of Cancer with Tumor-Infiltrating Lymphocytes", *Science*, 233(4770):1318-1321 (1986).

Roshal, M. et al., "Immaturity Associated Antigens Are Lost During Induction for T Cell Lymphoblastic Leukemia: Implications for Minimal Residual Disease Detection", *Cytometry Part B (Clinical Cytometry)*, 78:139-146 (2010).

Rozen, S., et al., "Primer3 on the WWW for General Users and for Biologist Programmers," *Methods in Molecular Biology*, Bioinformatics Methods and Protocols, 132:365-386 (2000).

Saada, R. et al., "Models for antigen receptor gene rearrangement: CDR3 length", Immunology and Cell Biology, 85:323-332 (2007).

Santalucia, Jr., J., "Physical Principles and Visual-OMP Software for Optimal PCR Design," *Methods in Molecular Biology*, 402(*PCR Primer Design*):3-33, 40 pages (2007).

Santamaria, P. et al., "Beta-Cell-Cytotoxic CDS T Cells from Nonobese Diabetic Mice Use Highly Homologous T Cell Receptor a-Chain CDR3 Sequences", *The Journal of Immunology*, 154(5):2494-2503 (1995).

Schlissel, M.S. et al., "Leukemia and lymphoma: a cost of doing business for adaptive immunity", *Genes Dev.*, 20(12):1539-44 (2006).

Schrappe, M. et al., "Late MRD response determines relapse risk overall and in subsets of childhood T-cell ALL: results of the AIEOP-BFM-All 2000 study", *Blood*, 118(8):2077-2084 (2011).

Sherwood, A., et al., "Deep Sequencing of the Human TCRγ and TCRβ Repertoires Suggests that TCR β Rearranges After αβ and γδ T Cell Commitment," *Science Translational Medicine*, 3(90):1-7 (2011).

Silver, N. et al., "Selection of housekeeping genes for gene expression studies in human reticulocytes using real-time PCR", *BMC Molecular Biology*, 7(33):1-9 (2006).

(56) References Cited

OTHER PUBLICATIONS

Sint, D., et al., "Advances in multiplex PCR: balancing primer efficiencies and improving detection success," *Methods in Ecology and Evolution*, 3(5):898-905 (2012).
Standard Sequencing Primers, Max Planck Genome Center Cologne, Jan. 15, 2011, downloaded from https://genomecentre.mpipz.mpg.de/SeqOrderDB/export/sequencing-primers.html.
Stein and Nombela-Arrieta, "Chemokine control of lymphocyte trafficking: a general overview," *Immunology*, 116(10):1-12 (2005).
Steinmetz, O.M. et al., "Chemokines and B cells in renal inflammation and allograft rejection," *Frontiers in Bioscience* (Schol. Ed.), 1:13-22 (2009).
Straten, Per thor, et al., "T-cell clonotypes in cancer", *Journal of Translational Medicine*, 2(1):11 (2004).
Supplementary European Search Report for European Application No. 10732172.1, dated May 29, 2012, 5 pages.
Szczepanski, T. et al., "Minimal residual disease in leukemia patients", *Lancet Oncology*, 2:409-417 (2001).
Tewhey, R. et al., "Corrigendum: Microdroplet-based PCR enrichment for large-scale targeted sequencing", *Nature Biotechnology*, 28(2):178, 1 page (2010).
Tewhey, R. et al., "Microdroplet-based PCR enrichment for large-scale targeted sequencing," *Nature Biotechnology*, 27(11):1025-1031 (2009).
Triebel, F. et al., "A Unique V-J-C-Rearranged Gene Encodes a γ Protein Expressed on the Majority of CD3+ T Cell Receptor -a/fr Circulating Lymphocytes", *J. Exp. Med.*, 167:694-699 (1988).
Van Der Velden, VHJ et al., "Analysis of minimal residual disease by Ig/TCR gene rearrangements: guidelines for interpretation of real-time quantitative PCR data," *Leukemia*, 21:604-611 (2007).
Van Der Velden, VHJ et al., "Optimization of PCR-based minimal residual disease diagnostics for childhood acute lymphoblastic leukemia in a multi-center setting," *Leukemia*, 21:706-713 (2007).
Van Der Velden, V.H.J., et al., "Detection of minimal residual disease in hematologic malignancies by realtime quantitative PCR: principles, approaches, and laboratory aspects," *Leukemia*, 17:1013-1034 (2003).
Van Der Velden, V.H.J., et al., "Real-time quantitative PCR for detection of minimal residual disease before allogeneic stem cell transplantation predicts outcome in children with acute lymphoblastic leukemia", *Leukemia*, 15:1485-1487 (2001).
Van Dongen, J.J.M. et al., "Design and standardization of PCR primers and protocols for detection of clonal immunoglobulin and T-cell receptor gene recombinations in suspect lymphoproliferations: Report of the BIOMED-2 Concerted Action BMHC-CT98-3936", *Leukemia*, 17:2257-2317 (2003).
Van Dongen, J.J.M. et al., "Prognostic value of minimal residual disease in acute lymphoblastic leukaemia in childhood," *The Lancet*, 352:1731-1738 (1998).
Venturi, V. et al., "The molecular basis for public T-cell responses?" *Nature Reviews*, 8:231-238 (2008).
Venturi, V. et al., "TCR β-Chain Sharing in Human CD8+ T Cell Responses to Cytomegalovirus and EBV[1]", *The Journal of Immunology*, 181:7853-7862 (2008).
Verhagen, O.J.H.M., et al., "Application of germline IGH probes in real-time quantitative PCR for the detection of minimal residual disease in acute lymphoblastic leukemia," *Leukemia*, 14:1426-1435 (2000).
Volgelstein and Kinzler, "Digital PCR," Genetics, *PNAS*, 96:9236-9241 (1999).
Wang, X. et al., "Quantitative Measurement of Pathogen Specific Human Memory T Cell Repertoire Diversity using a CDR3 B-Specific Microarray", *BMC Genomics*, 8(329): 1-13 (2007).
Ward and Marelli-Berg, "Mechanisms of chemokine and antigen-dependent T-lymphocyte navigation," *Biochem. J.*, 418:13-27 (2009).
Weinstein, J.A. et al., "High-Throughput Sequencing of the Zebrafish Antibody Repertoire", *Science*, 324:807-810 (2009).
Wood, B., "9-Color and 10-Color Flow Cytometry in the Clinical Laboratory," *Arch Pathol Lab Med*, 130:680-690 (2006).
Wu, H.D. et al., "The Lymphocytic Infiltration in Calcific Aortic Stenosis Predominantly Consists of Clonally Expanded T Cells", *The Journal of Immunology*, 178(8):5329-5339 (2007).
Wu, Y-C. et al., "High-throughput immunoglobulin repertoire analysis distinguishes between human IgM memory and switched memory B-cell populations", *Blood Journal*, 116(7):1070-1078, 22 pages (2010).
Xu, W. et al., "A Novel Universal Primer-Multiplex-PCR Method with Sequencing Gel Electrophoresis Analysis," *PLoS One*, 7(1):e22900, pp. 1-10 (2012).
Yassai, M.B. et al., "A clonotype nomenclature for T cell receptors", *Immunogenetics*, 61:493-502 (2009).
Zhong, Q. et al., "Multiplex digital PCR: breaking the one target per color barrier of quantitative PCR", *Lab Chip*, 11:2167-2174 (2011).
Abath et al. "Single-tubed nested PCR using immobilized internal primers", *Biotechniques*, 33(6): 1210-2, 1214 (2002).
Abbott, et al. "Design and use of signature primers to detect carry-over of amplified material", *J Virol Methods*, 46(1):51-59, Abstract Only (1994).
Ahmadzadeh et al. "FOXP3 expression accurately defines the population of intratumoral regulatory T cells that selectively accumulate in metastatic melanoma lesions", *Blood*, 112(13): 4953-4960 (2008).
Alatrakchi et al. "T-cell clonal expansion in patients with B-cell lymphoproliferative disorders", *Journal of Immunotherapy*, 21(5):363-370 (1998).
Altin et al. "The role of CD45 and CD45-associated molecules in T cell activation", *Immunology and Cell Biology*, 75: 430-445 (1997).
Altman, et al. "Phenotypic analysis of antigen-specific T lymphocytes", The *Journal of Immunology*, 187(1):7-9 (2011).
Altschul, et al. "Basic local alignment search tool", *J Mol Biol.*, 215(3):403-410 (1990).
Andreasson, et al. "The human IgE-encoding transcriptome to assess antibody repertoires and repertoire evolution", *J Mol Biol.*, 362(2):212-227 (2006). Epub Aug. 14, 2006.
Arnaout. "Specificity and overlap in gene segment-defined antibody repertoires", *BMC Genomics*, 6: 148 (2005).
Arden, et al. "Human T-cell receptor variable gene segment families", *Immunogenetics*, 42(6):455-500, Abstract Only (1995).
Armand, P. et al., "Detection of circulating tumour DNA in patients with aggressive B-cell non-Hodgkin lymphoma", *Brit. J. Haematol.*, vol. 163, pp. 123-126 (2013).
Aslanzadeh. "Preventing PCR amplification carryover contamination in a clinical laboratory", *Ann Clin Lab Sci.*, 34(4):389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).
Ateya, et al. "The good, the bad, and the tiny: a review of microflow cytometry", *Anal Bioanal Chem.*, 391(5): 1485-1498 (2008). doi: 10.1007/s00216-007-1827-5. Epub Jan. 29, 2008.
Babrzadeh et al. "Development on High-throughput Sequencing Technology: emPCR Titration and Barcode Design", *Stanford School of Medicine*, 2 pages (2011).
Bagnara, et al. "IgV gene intraclonal diversification and clonal evolution in B-cell chronic lymphocytic leukaemia", *British Journal of Haematology*, 133(1):50-58 (2006).
Baldauf, "Phylogeny for the faint of heart: a tutorial," Trends in Genetics, 19(6): 345-351 (2003).
Barbas, et al. "Assembly of combinatorial antibody libraries on phage surfaces: the gene III site", *PNAS*, 88(18): 7978-7982, Abstract Only (1991).
Barker, et al. "A second type II restriction endonuclease from Thermus aquaticus with an unusual sequence specificity", *Nucleic Acids Res.*, 12(14): 5567-5581 (1984).
Batzoglou, S. "The many faces of sequence alignment", *Briefings in Bioinformatics*, 6:6-22 (2005).
Baum and McCune et al. "Direct measurement of T-cell receptor repertoire diversity with AmpliCot", *Nat Methods*, 3(11): 895-901 (2006).

(56) References Cited

OTHER PUBLICATIONS

Becker-André and Hahlbrock. "Absolute mRNA quantification using the polymerase chain reaction (PCR). A novel approach by a PCR aided transcript titration assay (PATTY)", *Nucleic Acids Res.*, 17(22): 9437-9446 (1989).

Becton-Dickinson, CD marker handbook. bdbiosciences.com/go/mousecdmarkers, p. 1-47 (2010).

Becton-Dickinson T-Cell Research Tools, "Novel multicolor flow cytometry tools for the study of CD4+ T-cell differentiation and plasticity", 16 pages (2009).

Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", *Blood*, 83(8):2238-2247 (1994).

Ben-Ezra, et al. Effect of fixation on the amplification of nucleic acids from paraffin-embedded material by the polymerase chain reaction, *The Journal of Histochemistry and Cytochemistry*, 39(3): 351-354 (1991).

Béné and Kaeda, "How and why minimal residual disease studies are necessary in leukemia: a review from WP10 and WP12 of the European LeukaemiaNet", *Haematologica*, 94(8):1135-1150 (2009).

Benecke. "DNA typing in forensic medicine and in criminal investigations: a current survey", *Naturwissenschaften*, 84(5): 181-188 (1997).

Benichou, J. et al., "The restricted DH gene reading frame usage in the expressed human antibody repertoire is selected based upon its amino acid content", *J Immunol.*, 190(11): 5567-77, 29 pages (2013).

Bentley, et al. "Accurate whole human genome sequencing using reversible terminator chemistry", *Nature*, 456(7218) :53-59 (2008). doi: 10.1038/nature07517.

Bereczki, et al. "Optimization of PCR amplification for B- and T-cell clonality analysis on formalin-fixed and paraffin-embedded samples", *Pathology Oncology Research*, 13(3): 209-214 (2007). Epub Oct. 7, 2007.

Berger, et al. "The clonotypic T cell receptor is a source of tumor-associated antigens in cutaneous T cell lymphoma", *Annals of the New York Academy of Sciences*, 941:106-122, Abstract Only (2001).

Berget, et al. "Detection of clonality in follicular lymphoma using formalin-fixed, paraffin-embedded tissue samples and BIOMED-2 immunoglobulin primers", *J Clin Pathol.*, 64(1):37-41 (2011). doi: 10.1136/jcp.2010.081109. Epub Oct. 28, 2010.

Bernard et al. "Color multiplexing hybridization probes using the apolipoprotein E locus as a model system for genotyping", Anal Biochem., 273(2):221-228 (1999).

Bertness, et al. "T-Cell Receptor Gene Rearrangements as Clinical Markers of Human T-Cell Lymphomas", *The New England Journal of Medicine*, 313:534-538 (1985).

Berzofsky, et al. "Progress on new vaccine strategies for the immunotherapy and prevention of cancer", *J Clin Invest.*, 113(11): 1515-1525 (2004).

Biagi, et al. "Responses to human CD40 ligand/human interleukin-2 autologous cell vaccine in patients with B-cell chronic lymphocytic leukemia", *Clin Cancer Res.*, 11(19 Pt 1): 6916-6923 (2005).

Biggerstaff, et al. "Enumeration of leukocyte infiltration in solid tumors by confocal laser scanning microscopy", BMC Immunol., 7:16, 13 pages (2006).

Brochet et al. "IMGTN-QUEST: the highly customized and integrated system for Ig and TR standardized V-J and V-D-J sequence analysis", *Nucleic Acids Research*, vol. 36, Web Server issue W503-W508 (2008).

Bonner et al. "Fluorescence activated cell sorting", Rev Sci Instrum., 43(3):404-409, Abstract Only (1972).

Boria, et al. "Primer sets for cloning the human repertoire of T cell receptor variable regions", *BMC Immunology*, 9:50, 9 pages (2008).

Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.

Boudinot et al. "New perspectives for large-scale repertoire analysis of immune receptors", *Molecular Immunology*, 45: 2437-2445 (2008).

Bousso. "Generation of MHC-peptide tetramers: a new opportunity for dissecting T-cell immune responses", Microbes Infect., 2(4):425-429, Abstract Only (2000).

Boyce, et al. "Human regulatory T-cell isolation and measurement of function", *BD Biosciences*, pp. 1-20 (2010).

Boyd, S.D. et al., "Measurement and Clinical Monitoring of Human Lymphocyte Clonality by Massively Parallel V-D-J Pyrosequencing," *Science Translational Medicine*, 1:12ra23, 40 pages, including Supplementary Materials (2009).

Bradfield, et al. "Graft-versus-leukemia effect in acute lymphoblastic leukemia: the importance of tumor burden and early detection", Leukemia, 18(6): 1156-1158 (2004).

Bravo and Irizarry. "Model-Based Quality Assessment and Base-Calling for Second-Generation Sequencing Data", Biometrics, 66(3): 665-674 (2010).

Brehm-Stecher and Johnson. "Single-cell microbiology: tools, technologies, and applications", *Microbiology and Molecular Biology Reviews*, 68(3):538-559 (2004).

Brenner, et al. "In vitro cloning of complex mixtures of DNA on microbeads: physical separation of differentially expressed cDNAs", *PNAS*, 97(4): 1665-1670 (2000).

Brennan et al. "Predictable αβ T-cell receptor selection toward an HLA-B*3501-restricted human cytomegalovirus epitope", J. Virol., 81(13): 7269-7273 (2007).

Brentjens, et al. "CD19-targeted T cells rapidly induce molecular remissions in adults with chemotherapy-refractory acute lymphoblastic leukemia", Sci Transl Med., 5(177): 177ra38 (2013). doi: 10.1126/scitranslmed.3005930.

Brisco, et al. "Determining the repertoire of IGH gene rearrangements to develop molecular markers for minimal residual disease in B-lineage acute lymphoblastic leukemia", *J Mol Diagn.*, 11(3):194-200 (2009).

Brisco, et al. "Outcome prediction in childhood acute lymphoblastic leukaemia by molecular quantification of residual disease at the end of induction", *Lancet*, 343:196-200 (1994).

Brockman et al, "Quality scores and SNP detection in sequencing-by-synthesis systems," Genome Research, 18: 763-770 (2008).

Brody, et al. "Active and passive immunotherapy for lymphoma: proving principles and improving results", J Clin Oncol., 29(14):1864-1875, Abstract Only (2011). doi: 10.1200/JCO.2010.33.4623. Epub Apr. 11, 2011.

Brody, et al., "Immunotransplant for mantle cell lymphoma: Phase I/II study preliminary results", *Journal of Clinical Oncology*, ASCO Annual Meeting Abstracts Part 1, vol. 29, No. 15, 1 page (2011).

Brody, et al. "Lymphoma immunotherapy: vaccines, adoptive cell transfer and immunotransplant", *Immunotherapy*, 1(5): 809-824 (2009). doi: 10.2217/imt.09.50.

Brown, et al. "Current techniques for single-cell lysis", *J. R. Soc. Interface*, 5:S131-S138 (2008).

Brownie et al. "The elimination of primer-dimer accumulation in PCR", Nucleic Acids Research, 25(16): 3235-3241 (1997).

Brüggemann, et al. "Clinical significance of minimal residual disease quantification in adult patients with standard-risk acute lymphoblastic leukemia", *Blood*, 107(3):1116-1123 (2006). Epub Sep. 29, 2005.

Brüggemann, et al. "Rearranged T-cell receptor beta genes represent powerful targets for quantification of minimal residual disease in childhood and adult T-cell acute lymphoblastic leukemia", *Leukemia*, 18(4): 709-719 (2004).

Brüggemann, et al. "Standardized MRD quantification in European ALL trials: proceedings of the Second International Symposium on MRD assessment in Kiel, Germany, Sep. 18-20, 2008", *Leukemia*, 24(3):521-535 (2010). doi: 10.1038/leu.2009.268. Epub Dec. 24, 2009.

Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.

(56) References Cited

OTHER PUBLICATIONS

Buccisano, et al. "Monitoring of minimal residual disease in acute myeloid leukemia", Curr Opin Oncol., 21(6):582-588, Abstract Only (2009). doi: 10.1097/CCO.0b013e3283311856.

Bystrykh. "Generalized DNA Barcode Design Based on Hamming Codes", PLoS One, 7(5): e36852, 1-8 (2012).

Campana. "Minimal residual disease in acute lymphoblastic leukemia", Semin Hematol.,46(1):100-106 (2009).

Campana, et al. "Role of minimal residual disease monitoring in adult and pediatric acute lymphoblastic leukemia", Hematol Oncol Clin North Am., 23(5): 1083-1098 (2009). doi: 10.1016/j.hoc.2009.07.010.

Campbell et al. "Subclonal phylogenetic structures in cancer revealed by ultra-deep sequencing," PNAS, 105(35):13081-13086 (2008).

Carlotti, et al. "Transformation of follicular lymphoma to diffuse large B-cell lymphoma may occur by divergent evolution from a common progenitor cell or by direct evolution from the follicular lymphoma clone", Blood, 113(15): 3553-3557 (2009). doi: 10.1182/blood-2008-08-174839. Epub Feb. 6, 2009.

Carlson et al. "Profiling the repertoire of TCRB usage in induced and natural Treg cells", The Journal of Immunology, 186: 62.5, Abstract (2011).

Carlson, et al. "Immune Profiling Suggests an IGH Signaling-Dependent Subtype of Aggressive B-ALL", Blood, 120: 1428, Abstract (2012).

Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.

Carlson, et al. "Detection of tumor tagging clones in multiple myeloma via high throughput sequencing is robust to significant levels of SHM", Presented for the 2014 ASH Annual Meeting. Poster. 1 page. Dec. 5-9, 2014.

Casali, et al. "Human monoclonals from antigen-specific selection of B lymphocytes and transformation by EBV", Science, 234(4775): 476-479, Abstract Only (1986).

Casbon et al. "A method for counting PCR template molecules with application to next-generation sequencing", Nucleic Acids Research, 39(12): e81, 8 pages. (2011).

Catherwood, M.A. et al., "Improved clonality assessment in germinal centre/post germinal centre non-Hodgkin's lymphomas with high rates of somatic hypermutation", J. Clin. Pathol., 60:524-528, Abstract (2007).

Chan et al. "Evaluation of Nanofluidics Technology for High-Throughput SNP Genotyping in a Clinical Setting", The Journal of Molecular Diagnostics, 13(3): 305-312 (2011).

Chattopadhyay, et al. "A live-cell assay to detect antigen-specific CD4+ T cells with diverse cytokine profiles", Nat Med., 11(10): 1113-1117 (2005). Epub Sep. 25, 2005.

Chen et al. "A novel approach for the analysis of T-cell reconstitution by using a T-cell receptor β-based oligonucleotide microarray in hematopoietic stem cell transplantation", Exp Hematol., 35(5):831-841 (2007).

Chen et al. "Identification of racehorse and sample contamination by novel 24-plex STR system", Forensic Science International: Genetics, 4:158-167 (2010).

Chen, et al. "Microfluidic cell sorter with integrated piezoelectric actuator", Biomed Microdevices, 11(6): 1223-1231 (2009). doi: 10.1007/s10544-009-9341-5.

Chen, et al. "Total Gene Synthesis: Novel Single-Step and Convergent Strategies Applied to the Construction of a 779 Base Pair Bacteriorhodopsis", Gene. J. Am. Chem Soc., 116: 8799-8800, Abstract Only (1994).

Chiu, et al. "Non-invasive prenatal assessment of trisomy 21 by multiplexed maternal plasma DNA sequencing: large scale validity study", BMJ, 342:c7401, 9 pages (2011). doi: 10.1136/bmj.c7401.

Choi, et al. "Relapse in children with acute lymphoblastic leukemia involving selection of a preexisting drug-resistant subclone", Blood, 110(2):632-639 (2007).

Choi, et al. "Clonal evolution in B-lineage acute lymphoblastic leukemia by contemporaneous $V_H$-$V_H$ gene replacements and $V_H$-$DJ_H$ gene rearrangements", Blood, 87(6):2506-2512 (1996).

Churchill and Waterman. "The Accuracy of DNA Sequences: Estimating Sequence Quality", Genomics, 14:89-98 (1992).

Chute, et al. "Detection of immunoglobulin heavy chain gene rearrangements in classic Hodgkin lymphoma using commercially available BIOMED-2 primers", Diagn Mol Pathol., 17(2): 65-72 (2008). doi: 10.1097/PDM.0b013e318150d695.

Citri et al. "Comprehensive qPCR profiling of gene expression in single neuronal cells", Nature Protocols, 7(1): 118-127 (2012).

Cleary, et al. "Production of complex nucleic acid libraries using highly parallel in situ oligonucleotide synthesis", Nat Methods, 1(3): 241-248 (2004). Epub Nov. 18, 2004.

Clemente, et al. "Deep sequencing of the T-cell receptor repertoire in CD8+ T-large granular lymphocyte leukemia identifies signature landscapes", Blood, 122(25): 4077-85 (2013). doi: 10.1182/blood-2013-05-506386. Epub Oct. 22, 2013.

Cooper, et al. "BRAF inhibition is associated with increased clonality in tumor infiltrating lymphocytes", Oncoimmunology, 2(10):e26615 (2013). Epub Oct. 15, 2013.

Costabile, et al. "Molecular approaches in the diagnosis of primary immunodeficiency diseases", Human Mutation, 27(12):1163-1173 (2006).

Craig et al. "Identification of genetic variants using bar-coded multiplex sequencing", Nature Methods, 5(10): 887-893 (2008) and Supplemental Materials.

Cronin, et al. "Comprehensive next-generation cancer genome sequencing in the era of targeted therapy and personalized oncology", Biomark Med., 5(3):293-305 (2011). (Abstract only). doi: 10.2217/bmm.11.37.

Cronn et al. "Multiplex sequencing of plant chloroplast genomes using Solexa sequencing-by-synthesis technology", Nucleic Acids Research, 36(19):e122, 1-11 (2008).

Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", The Journal of Immunology, 172:1935-1944 (2004).

Currier and Robinson. "Spectratype/immunoscope analysis of the expressed TCR repertoire", Current Protocols in Immunology, Supplement 38:10.28.1-10.28.24 (2000).

Dahl et al. "Multiplex amplification enabled by selective circularization of large sets of genomic DNA fragments", Nucleic Acids Res., 33(8): e71 (2005).

Damle et al. "B-cell chronic lymphocytic leukemia cells express a surface membrane phenotype of activated, antigen-experienced B lymphocytes", Blood, 99(11): 4087-93 (2002).

Davi, et al. "Lymphocytic progenitor cell origin and clonal evolution of human B-lineage acute lymphoblastic leukemia", Blood, 88(2):609-621 (1996).

Davila, et al. Efficacy and toxicity management of 19-28z CART cell therapy in B cell acute lymphoblastic leukemia, Sci Transl Med., 6(224):224ra25 (2014). doi: 10.1126/scitranslmed.3008226.

Davis, et al. "Interrogating the repertoire: broadening the scope of peptide-MHC multimer analysis", Nat Rev Immunol., 11(8):551-558 (2011). doi: 10.1038/nri3020.

Davis, et al. "Staining of cell surface human CD4 with 2'-F-pyrimidine-containing RNA aptamers for flow cytometry", Nucleic Acids Research, 26(17):3915-3924 (1998).

De Bona et al. "Optimal spliced alignments of short sequence reads", Bioinformatics, 9(Suppl 10):O7, 2 pages (2008).

Dean, et al. "Rapid amplification of plasmid and phage DNA using Phi 29 DNA polymerase and multiply-primed rolling circle amplification", Genome Res., 11(6): 1095-1099 (2001).

Decoste et al. "Relative and Absolute Quantitative Real-Time PCR-Based Quantifications of hcnC and phlD Gene Transcripts in Natural Soil Spiked with Pseudomonas sp. Strain LBUM300", Applied and Environmental Microbiology, 77(1): 41-47 (2011).

Dedhia, et al. "Evaluation of DNA extraction methods and real time PCR optimization on formalin-fixed paraffin-embedded tissues", Asian Pac J Cancer Prev., 8(1): 55-59 (2007).

(56) References Cited

OTHER PUBLICATIONS

Deiman, et al. "Characteristics and applications of nucleic acid sequence-based amplification (NASBA)", Mol Biotechnol., 20(2): 163-179, Abstract Only (2002).
DeKosky et al. "High-throughput sequencing of the paired human immunoglobulin heavy and light chain repertoire", Nature Biotechnology, 31(2): 166-169 (2013).
Delaney, et al. "Evolution and Clinical Implications of the T cell Repertoire Following Cord Blood Transplant", Biology of Blood and Marrow Transplant, vol. 19, Issue 2, S201-S202. Published Feb. 2013.
Deng et al. "Gene profiling involved in immature CD4+ T lymphocyte responsible for systemic lupus erythematosus", Molecular Immunology, 43:1497-1507 (2006).
Deschoolmeester, et al. "Tumor infiltrating lymphocytes: an intriguing player in the survival of colorectal cancer patients", BMC Immunology, 11:19, 12 pages (2010). doi: 10.1186/1471-2172-11-19.
Desmarais, et al. "Deep profiling of the mouse TCRβ CDR3 region in thymus and spleen". Oct. 2010. Poster. 1 page.
Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.
Desmarais and Robins. "High-throughput sequencing of memory and naïve T cell receptor repertoires at the RNA and DNA levels reveals differences in relative expression of expanded TCR clones", The Journal of Immunology, 188: 178.12 (2012).
Dictor et al. "Resolving T-cell receptor clonality in two and genotype in four multiplex polymerase chain reactions", Haematologica, 90(11): 1524-1532 (2005).
Diederichsen, et al. "Prognostic value of the CD4+/CD8+ ratio of tumour infiltrating lymphocytes in colorectal cancer and HLA-DR expression on tumour cells", Cancer Immunol Immunother., 52(7):423-428 (2003). Epub Apr. 15, 2003.
Diehl, et al. "BEAMing: single-molecule PCR on microparticles in water-in-oil emulsions", Nat Methods, 3(7):551-559, Abstract Only (2006).
Diluvio et al. "Identical TCRβ-chain rearrangements in streptococcal angina and skin lesions of patients with psoriasis vulgaris", J Immunol., 176(11 ): 7104-11 (2006).
Ding, et al. "Clonal evolution in relapsed acute myeloid leukaemia revealed by whole-genome sequencing", Nature, 481(7382):506-510 (2012). doi: 10.1038/nature10738.
Diviacco, et al. "A novel procedure for quantitative polymerase chain reaction by coamplification of competitive templates", Gene, 122(2):313-320 (1992).
Do and Batzoglou. "What is the expectation maximization algorithm?", Nature Biotechnology, 26(8): 897-899 (2008).
Dohm, et al. "Substantial biases in ultra-short read data sets from high throughput DNA sequencing", Nucleic Acids Research, 36:e105, 10 pages. (2008).
Dou, et al. "Analysis of T cell receptor $V_\beta$ gene usage during the course of disease in patients with chronic hepatitis B", Journal of Biomedical Science, 5(6):428-434 (1998).
Dressman, et al. "Transforming single DNA molecules into fluorescent magnetic particles for detection and enumeration of genetic variations", PNAS, 100(15):8817-8822 (2003). Epub Jul. 11, 2003.
Drmanac, et al. "Human genome sequencing using unchained base reads on self-assembling DNA nanoarrays", Science, 327(5961):78-81 (2010). doi: 10.1126/science.1181498. Epub Nov. 5, 2009.
Droege, et al. "The Genome Sequencer FLX System—longer reads, more applications, straight forward bioinformatics and more complete data sets", J Biotechnol., 136(1-2):3-10 (2008). doi: 10.1016/j.jbiotec.2008.03.021. Epub Jun. 21, 2008.
Drossman, et al. "High-speed separations of DNA sequencing reactions by capillary electrophoresis", Anal Chem., 62(9): 900-903 (1990).
Du et al. "TCR spectratyping revealed T lymphocytes associated with graft-versus-host disease after allogeneic hematopoietic stem cell transplantation", Leukemia & Lymphoma, 48(8):1618-1627 (2007).
Dudgeon, et al. "The evolution of thymic lymphomas in p53 knockout mice", Genes Dev., 28(23): 2613-20 (2014). doi: 10.1101/gad.252148.114.
Dunn, et al. "Focus on TILs: Prognostic significance of tumor infiltrating lymphocytes in human glioma", Cancer Immun., 7:12, 16 pages (2007).
Eason et al. "Characterization of synthetic DNA bar codes in Saccharomyces cerevisiae gene-deletion strains," PNAS, 101(30): 11046-11051 (2004).
Edd et al. "Controlled encapsulation of single cells into monodisperse picoliter drops", Lab Chip, 8(8):1262-1264 (2008).
Eichler, et al. "Haplotype and interspersion analysis of the FMR1 CGG repeat identifies two different mutational pathways for the origin of the fragile X syndrome", Hum Mol Genet., 5(3):319-330 (1996).
Eichler, et al. "Length of uninterrupted CGG repeats determines instability in the FMR1 gene", Nat Genet., 8(1):88-94, Abstract Only (1994).
Eid et al. "Real-time DNA sequencing from single polymerase molecules", Science, 323(5910):133-138 (2009). doi: 10.1126/science.1162986. Epub Nov. 20, 2008.
Eis, et al. "An invasive cleavage assay for direct quantitation of specific RNAs", Nat Biotechnol., 19(7):673-676, Abstract Only (2001).
Eisenstein. "Personalized, sequencing-based immune profiling spurs startups", Nat Biotechnol., 31(3):184-6 (2013). doi: 10.1038/nbt0313-184b.
Elkord et al. "T regulatory cells in cancer: recent advances and therapeutic potential", Expert Opinion on Biological Therapy, 10(11): 1573-1586 (2010).
Emerson, et al. "Correlation of TCR diversity with immune reconstitution after cord blood transplant", Presented at the American Society of Clinical Oncology's annual meeting. May 2012. Poster. 1 page.
Emerson et al. "Defining the Alloreactive T Cell Repertoire Using High-Throughput Sequencing of Mixed Lymphocyte Reaction Culture", PLoS One, 9(11): e111943 (2014).
Emerson, et al. "CD4+ and CD8+ T cell β antigen receptors have different and predictable V and J gene usage and CDR3 lengths", Presented at the Annual Meeting of the American Association of Immunologists 2012 in Boston, MA May 2012. Poster.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, et al. TCR repertoire diversity assessed with immunosequencing is associated with patient mortality following cord blood transplant. Presented for the 2014 ASH Annual Meeting. Poster. 1 page. Dec. 5-9, 2014.
Estorninho, et al. "A novel approach to tracking antigen-experienced CD4 T cells into functional compartments via tandem deep and shallow TCR clonotyping", J Immunol., 191(11): 5430-40 (2013). doi: 10.4049/jimmunol.I300622. Epub Oct. 25, 2013.
Erlich, et al. "Alta-Cyclic: a self-optimizing base caller for next-generation sequencing", Nat Methods., 5(8): 679-682 (2008). doi: 10.1038/nmeth.1230. Epub Jul. 6, 2008.
European Application No. 09764927.1, Notice of Opposition dated Oct. 14, 2014, Reference# 547-7.
European Application No. 09764927.1, Notice of Opposition dated Oct. 14, 2014, Reference# BR0-0001EP.
European Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", Lung Cancer, 59(1): 32-40 (2008).
European Patent Application No. 13195379.6, European Search Report and Opinion dated Mar. 13, 2014, 6 pages.
European Patent Application No. 11777704.5, European Search Report dated Jul. 26, 2013, 6 pages.

(56) References Cited

OTHER PUBLICATIONS

European Patent Application No. 13804085.2, Extended European Search Report dated Nov. 16, 2015, 10 pages.
European Patent Application No. 13775514.6, Extended European Search Report dated Dec. 1, 2015, 12 pages.
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated Nov. 23, 2015.
Ewing and Green, "Base-calling of automated sequencer traces using Phred. I. Accuracy Assessment," Genome Research, 8: 175-185 (1998).
Felsenstein, et al. "Evolutionary Trees from DNA Sequences: A Maximum Likelihood Approach", J Mol Evol, 17:368-376 (1981).
Ferradini et al. "Analysis of T Cell Receptor Variability in Tumor-infiltrating Lymphocytes from a Human Regressive Melanoma", *J. Clin. Invest.*, pp. 1183-1190 (1993).
Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.
Fisher et al. "The Relation Between the Number of Species and the Number of Individuals in a Random Sample of an Animal Population", *Journal of Animal Ecology*, 12(1): 42-58 (1943).
Flaherty et al. "Ultrasensitive detection of rare mutations using next-generation targeted resequencing", *Nucleic Acids Research*, 40(1): e2, 12 pages (2012).
Flicek and Birney, "Sense from sequence reads: methods for alignment and assembly," Nature Methods Supplement, 6(11s): S6-S12 (2009).
Frampton, et al. "Development and validation of a clinical cancer genomic profiling test based on massively parallel DNA sequencing", *Nat Biotechnol.*, 31(11): 1023-1031 (2013). doi: 10.1038/nbt.2696. Epub Oct. 20, 2013.
Frank. "BARCRAWL and BARTAB: software tools for the design and implementation of barcoded primers for highly multiplexed DNA sequencing," *BMC Bioinformatics*, 10: 362 (2009).
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", *Biotechniques*, 6(1): 112-125 (1999).
Fridman, et al. "Prognostic and predictive impact of intra- and peritumoral immune infiltrates", *Cancer Research*, 71(17): 5601-5605 (2011). doi: 10.1158/0008-5472.CAN-11-1316. Epub Aug. 16, 2011.
Fritz et al. "Alterations in the spinal cord T cell repertoire during relapsing experimental autoimmune encephalomyelitis," *J Immunol*, 164:6662-6668 (2000).
Fu et al. "Counting individual DNA molecules by the stochastic attachment of diverse labels", *PNAS*, 108(22): 9026-9031 and Supporting Materials, 8 pages (2011).
Fuller, et al. "The challenges of sequencing by synthesis", *Nat Biotechnol.*, 7(11): 1013-23 (2009) (Abstract only). doi: 10.1038/nbt.1585. Epub Nov. 6, 2009.
Furmanski, et al. "Public T cell receptor β-chains are not advantaged during positive selection", *The Journal of Immunology*, 180(2): 1029-39 (2008).
García-Castillo and Núnez, et al. "Detection of clonal immunoglobulin and T-cell receptor gene recombination in hematological malignancies: monitoring minimal residual disease", *Cardiovascular & Haematological Disorders-Drug Targets*, 9:124-135 (2009).
Gauss, et al. "Mechanistic constraints on diversity in human V(D)J recombination", *Mol Cell Biol.*, 16(1):258-269 (1996).
Gawad, et al. "Massive evolution of the immunoglobulin heavy chain locus in children with B precursor acute lymphoblastic leukemia", *Blood*, 120(22):4407-4417 (2012). doi: 10.1182/blood-2012-05-429811. Epub Aug. 28, 2012.

Gerlinger and Swanton. "How Darwinian models inform therapeutic failure initiated by clonal heterogeneity in cancer medicine", *British Journal of Cancer*, 103(8):1139-1143 (2010). doi: 10.1038/sj.bjc.6605912. Epub Sep. 28, 2010.
Germano, et al. "Clonality profile in relapsed precursor-B-ALL children by GeneScan and sequencing analyses. Consequences on minimal residual disease monitoring", *Leukemia*, 17(8):1573-1582 (2003).
Giga—Roche 454 FLX technology how it works. Fiche technique du Centre Interdisciplinaire de Genoproteomique Appliquee (Universite de Liege, Belgique). Accessed Oct. 15, 2014.
Gilbert, et al. "The isolation of nucleic acids from fixed, paraffin-embedded tissues-which methods are useful when?", *PLoS One*, 2(6):e537, 12 pages (2007).
Giuggio, et al. "Evolution of the intrahepatic T cell repertoire during chronic hepatitis C virus infection", *Viral Immunology*, 18(1):179-189 (2005).
Gloor et al. "Microbiome profiling by Illumina sequencing of combinatorial sequence-tagged PCR products," *PLoS One*, 5(10): e15406, 15 pages (2010).
Godelaine, et al. "Polyclonal CTL responses observed in melanoma patients vaccinated with dendritic cells pulsed with a MAGE-3.A1 peptide", *J Immunol.*, 171(9):4893-4897 (2003).
Golembowski, et al. "Clonal evolution in a primary cutaneous follicle center B cell lymphoma revealed by single cell analysis in sequential biopsies", *Immunobiology*, 201(5):631-644 (2000).
Gomes, et al. "Single-tube nested PCR using immobilized internal primers for the identification of dengue virus serotypes", *J Virol Methods.*, 145(1):76-9 (2007). Epub Jun. 15, 2007.
Gonzalez, et al. "Incomplete DJH rearrangements of the IgH gene are frequent in multiple myeloma patients: immunobiological characteristics and clinical implications", *Leukemia*, 17:1398-1403 (2003).
Gonzalez et al., "Incomplete DJH rearrangements as a novel tumor target for minimal residual disease quantitation in multiple myeloma using real-time PCR", Leukemia, 17:1051-1057 (2003).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", *J Immunol.*, 152(10):5109-5119 (1994).
Gottenberg, et al. "Markers of B-lymphocyte activation are elevated in patients with early rheumatoid arthritis and correlated with disease activity in the ESPOIR cohort", *Arthritis Res Ther.*, 11(4): R114 (2009). doi: 10.1186/ar2773. Epub Jul. 23, 2009.
Gratama and Kern. "Flow cytometric enumeration of antigen-specific T lymphocytes", *Cytometry A*, 58(1): 79-86 (2004).
Gratama, et al. "Measuring antigen-specific immune responses", 2008 update. *Cytometry A.*, 73(11): 971-974 (2008). doi: 10.1002/cyto.a.20655.
Green, et al. "Clonal diversity of Ig and T-cell-receptor gene rearrangements identifies a subset of childhood B-precursor acute lymphoblastic leukemia with increased risk of relapse", *Blood*, 92(3):952-958 (1998).
Greenberg, et al. "Profile of immunoglobulin heavy chain variable gene repertoires and highly selective detection of malignant clonotypes in acute lymphoblastic leukemia" J Leukoc Biol., 57(6):856-864 (1995).
Greenman, et al. "Patterns of somatic mutation in human cancer genomes", *Nature*, 446(7132): 153-158 (2007).
Gribben, JG. "Stem cell transplantation in chronic lymphocytic leukemia", *Biol. Blood Marrow Transplant.*, 15(1 Suppl): 53-58 (2009). doi: 10.1016/j.bbmt.2008.10.022.
Grupp, et al. "Chimeric antigen receptor-modified T cells for acute lymphoid leukemia", N Engl J Med., 368(16):1509-18 (2013). doi: 10.1056/NEJMoa1215134. Epub Mar. 25, 2013.
Grupp, et al. "Adoptive transfer of autologous T cells improves T-cell repertoire diversity and long-term B-cell function in pediatric patients with neuroblastoma", Clin Cancer Res., 18(24):6732-41 (2012). doi: 10.1158/1078-0432.CCR-12-1432. Epub Oct. 23, 2012.

(56) References Cited

OTHER PUBLICATIONS

Gulliksen, et al. "Real-time nucleic acid sequence-based amplification in nanoliter volumes", Anal Chem., 76(1): 9-14, Abstract Only (2004).

Gunderson et al. "Decoding Randomly Ordered DNA Arrays", Genome Research, 14: 870-877 (2004).

Guo, et al. "Sequence changes at the V-D junction of the $V_H1$ heavy chain of anti-phosphocholine antibodies alter binding to and protection against Streptococcus pneumoniae", Int Immunol., 9(5):665-677 (1997).

Gupta, Pushpendra K. "Single-molecule DNA sequencing technologies for future genomics research", Trends Biotechnol., 26(11): 602-611 (2008). doi: 10.1016/j.tibtech.2008.07.003. Epub Aug. 21, 2008.

Gurrieri, et al. "Chronic lymphocytic leukemia B cells can undergo somatic hypermutation and intraclonal immunoglobulin $V_HDJ_H$ gene diversification", J Exp Med., 196(5):629-639 (2002).

Hadrup, et al. "Parallel detection of antigen-specific T-cell responses by multidimensional encoding of MHC multimers", Nat Methods, 6(7): 520-526 (2009) (Abstract Only). doi: 10.1038/nmeth.1345. Epub Jun. 21, 2009.

Halldórsdóttir, et al. "Application of BIOMED-2 clonality assays to formalin-fixed paraffin embedded follicular lymphoma specimens: superior performance of the IGK assays compared to IGH for suboptimal specimens", Leukemia & Lymphoma, 48(7): 1338-1343 (2007).

Hamady, et al. "Error-correcting barcoded primers for pyrosequencing hundreds of samples in multiplex", Nature Methods, 5(3):235-237 (2008). doi: 10.1038/nmeth.1184. Epub Feb. 10, 2008.

Han et al. "Immunorepertoire analysis by multiplex PCR amplification and high throughput sequencing", The Journal of Immunology, 182:42.6, 1 page (2009).

Hanahan, et al. "Hallmarks of cancer: the next generation", Cell, 144(5): 646-674 (2011). doi: 10.1016/j.cell.2011.02.013.

Harismendy et al. "Evaluation of next generation sequencing platforms for population targeted sequencing studies", Genome Biology, 10:R32, 13 pages (2009).

Harris et al. "Single-Molecule DNA Sequencing of a Viral Genome", Science, 320: 106-109 (2008).

Hathcock, et al. "ATM influences the efficiency of TCRβ rearrangement, subsequent TCRβ-dependent T cell development, and generation of the pre-selection TCRβ CDR3 repertoire", PLoS One, 8(4):e62188 (2013). doi: 10.1371/journal.pone.0062188. Print 2013.

Hawkins, et al. "Whole genome amplification—applications and advances", Curr Opin Biotechnol., 13(1): 65-67 (2002).

He, et al. "IgH gene rearrangements as plasma biomarkers in Non-Hodgkin's lymphoma patients", Oncotarget, 2(3): 178-185 (2011).

Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq e=el&hq m=966798 &hq I=10&hq v=2357e2f0b3. Accessed Apr. 6, 2011.

Heger. "Roche's 454 Eyes Immune Repertoire Sequencing as Key Application for Long-Read Platform". Feb. 2, 2010. 4 pages. http://www.genomeweb.com/print/932624.

Hensel et al. "Simultaneous identification of bacterial virulence genes by negative selection", Science, 269(5222): 400-403 (1995).

Hill, et al. "Using ecological diversity measures with bacterial communities", FEMS Microbiol Ecol., 43(1):1-11 (2003). doi: 10.1111/j.1574-6941.2003.tb01040.x.

Hirohata, et al. "Regulation of human B cell function by sulfasalazine and its metabolites", Int Immunopharmacol., 2(5): 631-640, Abstract Only (2002).

Holder and Lewis. "Phylogeny estimation: traditional and bayesian approaches", Nat Rev Genet., 4(4): 275-84 (2009).

Holt. "Q &A: BC cancer agency's Robert Holt on sequencing the immune repertoire in immune reconstitution," Genome Web (www.genomeweb.com) Jun. 30, 2009.

Holt and Jones. "The new paradigm of flow cell sequencing", Genome Research, 18:839-846 (2008).

Hoogenboom, et al. "Multi-subunit proteins on the surface of filamentous phage: methodologies for displaying antibody (Fab) heavy and light chains", Nucleic Acids Res., 19(15): 4133-4137 (1991).

Hoogendoorn, et al. "Primary allogeneic T-cell responses against mantle cell lymphoma antigen-presenting cells for adoptive immunotherapy after stem cell transplantation", Clin Cancer Res., 11(14): 5310-5318 (2005).

Hoos, et al. "Improved endpoints for cancer immunotherapy trials", J Natl Cancer Inst., 102(18): 1388-1397 (2010). doi: 10.1093/jnci/djq310. Epub Sep. 8, 2010.

Hoover and Lubkowski. "DNAWorks: an automated method for designing oligonucleotides for PCR-based gene synthesis", Nucleic Acids Res., 30(10): e43, 7 pages (2002).

Hosono, et al. "Unbiased whole-genome amplification directly from clinical samples", Genome Res., 13(5): 954-964 (2003). Epub Apr. 14, 2003.

Hoven, et al. "Detection and isolation of antigen-specific B cells by the fluorescence activated cell sorter (FACS)", J Immunol Methods, 117(2): 275-284, Abstract Only, 2 pages (1989).

Howe, et al. "T cell receptor clonotype analysis of T cell responses: Diagnostic application of a clonotypic database", Blood, 102:Abstract 3918 (2003).

Huang, et al. "Isolation of cell-free DNA from maternal plasma using manual and automated systems", Methods Mol Biol., 444: 203-208, Abstract Only (2008). doi: 10.1007/978-1-59745-066-9_15.

Huh, et al. "Microfluidics for flow cytometric analysis of cells and particles", Physiol Meas., 26(3): R73-98, Abstract Only (2005). Epub Feb. 1, 2005.

Huijsmans, et al. "Comparative analysis of four methods to extract DNA from paraffin-embedded tissues: effect on downstream molecular applications", BMC Res Notes, 3:239, 9 pages (2010). doi: 10.1186/1756-0500-3-239.

Huse, et al. "Generation of a large combinatorial library of the immunoglobulin repertoire in phage lambda", Science, 246(4935): 1275-1281, Abstract Only (1989).

Huse et al. "Accuracy and quality of massively parallel DNA pyrosequencing", Genome Biology, 8: R143 (2007).

Iancu, et al. "Profile of a serial killer: cellular and molecular approaches to study individual cytotoxic T-cells following therapeutic vaccination", J Biomed Biotechnol., 2011: 452606 (2011). doi: 10.1155/2011/452606. Epub Nov. 14, 2010.

Illumina. Genome analyzer pipeline software version 1.0 user guide. Part #1004759, 176 pages (2008).

Illumina. Data Sheet: Sequencing. Genomic Sequencing. Pub. No. 770.2008-016 Reference states: "Current as of Jan. 30, 2009", 6 pages (2010).

Illumina. Data Sheet, "TruSeq™ exome enrichment kit", 5 pages (2011).

Illumina Systems & Software, Technology Spotlight, DNA Sequencing with Solexa® Technology, Illumina, Inc., Pub. No. 770-2007-002, 4 pages (2007).

Illumina. "Technical Note: Systems and Software. Calling sequencing SNPs", 3 pages (2010).

Illumina. TruSeq Sample Preparation Kit and Data Sheet. Illumina, Inc., San Diego, CA, 4 pages (2011).

Ishii et al. "Isolation and expression profiling of genes upregulated in the peripheral blood cells of systemic lupus erythematosus patients," DNA Research, 12:429-439 (2005).

Jabara et al. "Accurate sampling and deep sequencing of the HIV-1 protease gene using a Primer ID", PNAS, 108(50): 20166-20171 (2011).

Jacobi et al. "Activated memory B cell subsets correlate with disease activity in systemic lupus erythematosus: delineation by expression of CD27, IgD, and CD95", Arthritis & Rheumatism, 58(6):1762-1773 (2008).

Jacobi et al. "Correlation between circulating $CD27^{high}$ plasma cells and disease activity in patients with systemic lupus erythematosus" Arthritis & Rheumatism, 48(5):1332-1342 (2003).

(56) References Cited

OTHER PUBLICATIONS

Jaffe, et al. "Classification of lymphoid neoplasms: the microscope as a tool for disease discovery", Blood, 112(12): 4384-4399 (2008). doi: 10.1182/blood-2008-07-077982.
Jalla, et al. "Enumeration of lymphocyte subsets using flow cytometry: Effect of storage before and after staining in a developing country setting", Indian J Clin Biochem., 19(2): 95-99 (2004). doi: 10.1007/BF02894264.
Jena, et al. "Amplification of genes, single transcripts and cDNA libraries from one cell and direct sequence analysis of amplified products derived from one molecule", J. Immunol. Methods, 190:199-213 (1996).
Jones, et al. "Human autoimmunity after lymphocyte depletion is caused by homeostatic T-cell proliferation", Proc Natl Acad Sci USA, 110(50) :20200-5 (2013). doi: 10.1073/pnas.1313654110. Epub Nov. 26, 2013.
Jung, et al. "Unraveling V(D)J recombination; insights into gene regulation", Cell, 116(2): 299-311 (2004).
Jurkat, Clone 6-1 (ATCC TIB-152) Webpage retrievable from the ATCC under http://www.lgcstandards-atcc.org/Products/ All MB-152.aspx#characteristics. Accessed Oct. 14, 2014.
Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt.2012.06.005. Epub Jun. 12, 2012.
Kato et al. "Analysis of accumulated T cell clonotypes in patients with systemic lupus erythematosus," Arthritis & Rheumatism, 43(12):2712-2721 (2000).
Kedzierska, et al. "Tracking phenotypically and functionally distinct T cell subsets via T cell repertoire diversity", Mol Immunol., 45(3): 607-618 (2008). Epub Aug. 24, 2007.
Kim, et al. "An efficient and reliable DNA extraction method for preimplantation genetic diagnosis: a comparison of allele drop out and amplification rates using different single cell lysis methods", Fertility and Sterility, 92: 814-818 (2009).
Kim, et al. "Polony multiplex analysis of gene expression (PMAGE) in mouse hypertrophic cardiomyopathy", Science, 316(5830):1481-1484 (2007).
Kinde et al. "Detection and quantification of rare mutations with massively parallel sequencing," PNAS, 108(23): 9530-9535 and Supporting Information, 16 pages (2011).
Kircher, et al. "Improved base calling for the Illumina Genome Analyzer using machine learning strategies", Genome Biol., 10(8): R83, 9 pages (2009). doi: 10.1186/gb-2009-10-8-r83. Epub Aug. 14, 2009.
Kirsch, et al. "Defining immunoglobulin somatic hypermutation in de novo diffuse large b-cell lymphoma patients: potential application prognosis and risk stratification", Presented for the 2014 ASH Annual Meeting. Poster. 1 page. Dec. 5-9, 2014.
Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.
Kita, et al. "T cell receptor clonotypes in skin lesions from patients with systemic lupus erythematosus", Journal of Investigative Dermatology,110(1): 41-6 (1988).
Kivioja et al. "Counting absolute numbers of molecules using unique molecular identifiers," Nature Methods, 9(1): 72-76 (2012).
Klinger et al. "Combining next-generation sequencing and immune assays: a novel method for identification of antigen-specific T cells", PLoS One, 8(9): e74231, 1-9 (2013).
Klebanoff, et al. "Therapeutic cancer vaccines: are we there yet?", Immunol Rev., 239(1): 27-44 (2011). doi: 10.1111/j.1600-065X.2010.00979.x.
Klenerman, et al. "Tracking T cells with tetramers: new tales from new tools", Nat Rev Immunol., 2(4):263-272 (2002).
Kneba, et al. "Characterization of clone-specific rearrangement T-cell receptor gamma-chain genes in lymphomas and leukemias by the polymerase chain reaction and DNA sequencing", Blood, 84(2):574-581 (1994).

Kobari, et al. "T cells accumulating in the inflamed joints of a spontaneous murine model of rheumatoid arthritis become restricted to common clonotypes during disease progression", Int Immunol., 16(1):131-138 (2004).
Koboldt et al., "VarScan: variant detection in massively parallel sequencing of individual and pooled samples", Bioinformatics, 25(17): 2283-2285 (2009).
Koch, et al. "Tumor infiltrating T lymphocytes in colorectal cancer: Tumor-selective activation and cytotoxic activity in situ," Ann Surg., 244(6): 986-992; discussion 992-993 (2006).
Kojima et al. "PCR amplification from single DNA molecules on magnetic beads in emulsion: application for high-throughput screening of transcription factor targets", Nucleic Acids Research, 33: 17, e150, 9 pages (2005).
Kohlmann, et al. "Integration of next-generation sequencing into clinical practice: are we there yet?", Semin Oncol., 39(1): 26-36, Abstract Only (2012). doi: 10.1053/j.seminoncol.2011.11.008.
Kou, et al. "T-Cell receptor Vbeta repertoire CDR3 length diversity differs within CD45RA and CD45RO T-cell subsets in healthy and human immunodeficiency virus-infected children", Clin Diagn Lab Immunol., 7(6):953-9 (2000).
Krause et al. "Epitope-Specific Human Influenza Antibody Repertoires Diversify by B Cell Intraclonal Sequence Divergence and Interclonal Convergence", The Journal of Immunology, 187: 3704-3711 (2011).
Krueger, et al. "Large scale loss of data in low-diversity illumine sequencing libraries can be recovered by deferred cluster calling", PLoS One, 6(1): e16607, 7 pages (2011). doi: 10.1371/journal.pone.0016607.
Ku, et al. "Exome sequencing: dual role as a discovery and diagnostic tool", Ann Neurol., 71(1):5-14, Abstract Only (2012). doi: 10.1002/ana.22647.
Kumar, et al. "PEG-labeled nucleotides and nanopore detection for single molecule DNA sequencing by synthesis",Sci Rep., 2:684, 8 pages (2012). Epub Sep. 21, 2012.
Kwak, et al. "Induction of immune responses in patients with B-cell lymphoma against the surface-immunoglobulin idiotype expressed by their tumors", N Engl J Med., 327(17):1209-1215 (1992).
Kyu et al. "Frequencies of human influenza-specific antibody secreting cells or plasmablasts post vaccination from fresh and frozen peripheral blood mononuclear cells", Journal of Immunological Methods, 340: 42-47 (2009).
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", Blood, vol. 120 , No. 21, Abstract 788 (Conference Abstract), Entire Abstract (2012).
Landwehr-Kenzel, et al. "Novel GMP-compatible protocol employing an allogeneic B cell bank for clonal expansion of allospecific natural regulatory T cells", Am J Transplant., 14(3):594-606 (2014). doi: 10.1111/ajt.12629. Epub Jan. 27, 2014.
Langerak, et al. "Immunoglobulin/T-cell receptor clonality diagnostics", Expert Opin. Med. Diagn., 1(3):451-461 (2007).
Langerak, et al. "Polymerase chain reaction-based clonality testing in tissue samples with reactive lymphoproliferations: usefulness and pitfalls. A report of the BIOMED-2 Concerted Action BMH4-C198-3936", Leukemia, 21(2):222-229 (2007).
Laplaud et al. "Blood T-cell receptor β chain transcriptome in multiple sclerosis. Characterization of the T cells with altered CDR3 length distribution", Brain, 127:981-995 (2004).
Laplaud et al. "Serial blood T cell repertoire alterations in multiple sclerosis patients; correlation with clinical and MRI parameters", Journal of Neuroimmunology, 177(1-2):151-160 (2006).
Lassmann, et al. "Application of BIOMED-2 primers in fixed and decalcified bone marrow biopsies: analysis of immunoglobulin H receptor rearrangements in B-cell non-Hodgkin's lymphomas", J Mol Diagn., 7(5): 582-591 (2005).
Lazareva-Ulitsky et al, "On the quality of tree-based protein classification," Bioinformatics, 21(9): 1876-1890 (2005).
Lee, et al. "Characterization of circulating T cells specific for tumor-associated antigens in melanoma patients", Nat Med., 5(6): 677-685, Abstract Only (1999).

(56) References Cited

OTHER PUBLICATIONS

Lee, et al. "Prognostic implications of type and density of tumour-infiltrating lymphocytes in gastric cancer", *Br J Cancer*, 99(10): 1704-1711 (2008). doi: 10.1038/sj.bjc.6604738. Epub Oct. 21, 2008.
Lefranc. "IMGT, the international ImMunoGeneTics database", *Nucleic Acids Res.*, 31(1):307-310 (2003).
Leiden, J.M. et al. "The Complete Primary Structure of the T-Cell Receptor Genes From an Alloreactive Cytotoxic Human T-Lymphocyte Clone", Immunogenetics, 24(1): 17-23 (1986).
Leisner, et al. "One-pot, mix-and-read peptide-MHC tetramers", *PLoS One*, 3(2):e1678, 11 pages (2008). doi: 10.1371/journal.pone. 0001678.
Lennon, et al. "A scalable, fully automated process for construction of sequence-ready barcoded libraries for 454", *Genome Biol.*, 11(2):R15, 9 pages (2010). doi: 10.1186/gb-2010-11-2-r15. Epub Feb. 5, 2010.
Leary, et al. "Development of personalized tumor biomarkers using massively parallel sequencing", Sci Transl Med., 2(20): 20ra14 (2010). doi: 10.1126/scitranslmed.3000702.
Leone, et al. "Molecular beacon probes combined with amplification by NASBA enable homogeneous, real-time detection of RNA", *Nucleic Acids Research*, 26(9): 2150-2155 (1998).
Leproust, et al. "Synthesis of high-quality libraries of long (150mer) oligonucleotides by a novel depurination controlled process", *Nucleic Acids Res.*, 38(8): 2522-2540 (2010). doi: 10.1093/nar/gkq163. Epub Mar. 22, 2010.
Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).
Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).
Li, et al. "An improved one-tube RT-PCR protocol for analyzing single-cell gene expression in individual mammalian cells", *Anal. Bioanal. Chem.*, 397: 1853-1859 (2010).
Li, et al. "β cell-specific CD4+ T cell clonotypes in peripheral blood and the pancreatic islets are distinct", *J Immunol.*, 183(11): 7585-7591 (2009). doi: 10.4049/jimmunol.0901587. Epub Nov. 16, 2009.
Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).
Li, et al. "Detailed clonality analysis of relapsing precursor B acute lymphoblastic leukemia: implications for minimal residual disease detection", *Leukemia Research*, 25:1033-1045 (2001).
Li et al, "Mapping short DNA sequencing reads and calling variants using mapping quality scores," Genome Research, 18: 1851-1858 (2008).
Li, et al. "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection", *Blood*, 102:4520-4526 (2003).
Liedtke, et al. "A comparison of methods for RNA extraction from lymphocytes for RT-PCR", *PCR Methods and Applications*, 4(3): 185-187 (1994).
Lin, et al. "Multiplex genotype determination at a large number of gene loci", *Proc Natl Acad Sci USA*, 93(6): 2582-2587 (1996).
Liu, et al. "CD127 expression inversely correlates with FoxP3 and suppressive function of human CD4+ T reg cells", *J Exp Med.*, 203(7): 1701-1711 (2006). Epub Jul. 3, 2006.
Lo, et al. "T cell immunodominance is dictated by the positively selecting self-peptide", Elife, 3:e01457 (2014). doi: 10.7554/eLife. 01457. Epub Jan. 14, 2014.
Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).
Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).
Lossos, et al. "Transformation of follicular lymphoma to diffuse large-cell lymphoma: alternative patterns with increased or decreased expression of c-myc and its regulated genes", *PNAS*, 99(13): 8886-8891 (2002).
Lovisa, et al. "IGH and IGK gene rearrangements as PCR targets for pediatric Burkitt's lymphoma and mature B-ALL MRD analysis", *Lab Invest.*, 89(10):1182-1186 (2009).
Lowman, et al. "Monovalent phage display: a method for selecting variant proteins from random libraries", *Methods: A Companion to Methods in Enzymology*, 3: 205-216, Abstract Only (1991).
Lyamichev, et al. "Polymorphism identification and quantitative detection of genomic DNA by invasive cleavage of oligonucleotide probes", *Nat Biotechnol.*, 17(3): 292-396 (1999).
Luo et al. "Analysis of the interindividual conservation of T cell receptor α- and β-chain variable regions gene in the peripheral blood of patients with systemic lupus erythematosus", *Clinical & Experimental Immunology*, 154(3):316-324 (2008).
Mackay, et al. "Real-time PCR in virology", *Nucleic Acids Res.*, 30(6): 1292-305 (2002).
Maldonado, et al. "Intramuscular therapeutic vaccination targeting HPV16 induces T cell responses that localize in mucosal lesions", Sci Transl Med., 6(221): 221ra13 (2014). doi: 10.1126/scitranslmed. 3007323.
Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.
Manion et al., "Reducing Error in Next Generation Sequencing Data with NextGENe Software's Condensation Tool™", Mar. 2009, pp. 1-3. XP055226038.
Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.
Mar et al. "Inferring steady state single-cell gene expression distributions from analysis of mesoscopic samples", *Genome Biology*, 7(12): R119, 12 pages (2006).
Mardis. "Next-generation DNA sequencing methods", *Annu. Rev. Genomics Hum. Genet.*, 9:387-402 (2008). doi: 10.1146/annurev. genom.9.081307.164359.
Margulies, et al. "Genome sequencing in microfabricated high-density picolitre reactors", *Nature*, 437(7057):376-380 (2005). Epub Jul. 31, 2005.
Marrero, et al. "High-throughput sequencing of islet-infiltrating memory CD4+ T cells reveals a similar pattern of TCR Vβ usage in prediabetic and diabetic NOD mice", PLoS One, 8(10):e76546 (2013). doi: 10.1371/joumal.pone.0076546. eCollection 2013.
Martin-Jimenez, et al. "Molecular characterization of heavy chain immunoglobulin gene rearrangements in Waldenström's macroglobulinemia and IgM monoclonal gammopathy of undetermined significance", *Haematologica*, 92(5): 635-642 (2007).
Mary et al. "Analysis of gene expression at the single-cell level using microdroplet-based microfluidic technology", *Biomicrofluidics*, 5: 024109-1-024109-10 (2011).
Mato et al. "Correlation of clonal T cell expansion with disease activity in systemic lupus erythematosus", *Int Immunol.*, 9(4):547-554 (1997).
Matolcsy, et al. "Clonal evolution of B cells in transformation from low- to high-grade lymphoma", *Eur. J. Immunol.*,29(4):1253-1264 (1999).
Matsubara, et al. "Microchamber array based DNA quantification and specific sequence detection from a single copy via PCR in nanoliter volumes", *Biosens Bioelectron*, 20(8): 1482-1490, Abstract Only (2005).
Matsumoto et al. "CDR3 spectratyping analysis of the TCR repertoire in Myasthenia Gravis", *The Journal of Immunology*, 176:5100-5107 (2006).

(56) References Cited

OTHER PUBLICATIONS

Matsumoto et al. "Complementarity-determining region 3 spectratyping analysis of the TCR repertoire in multiple sclerosis", *The Journal of Immunology*, 170:4846-4853 (2003).

Mazor et al. "Antibody internalization studied using a novel IgG binding toxin fusion", *Journal of Immunological Methods*, 321: 41-59 (2007).

Mazumder, et al., "Detection of multiple myeloma cells in peripheral blood using high-throughput sequencing assay" *Blood*, vol. 120, No. 21, Abstract 321 (Conference Abstract), Entire Abstract (2012).

McCloskey et al. "Encoding PCR products with batch-stamps and barcodes," *Biochem. Genet.*, 45: 761-767 (2007).

McGoldrick, et al. "Cytomegalovirus-specific T cells are primed early after cord blood transplant but fail to control virus in vivo", *Blood*, 121(14): 2796-803 (2013). doi: 10.1182/blood-2012-09-453720. Epub Feb. 14, 2013.

McLean et al. "Recognition of human cytomegalovirus by human primary immunoglobulins identifies an innate foundation to an adaptive immune response", J. Immunol., 174(8): 4768-4778 (2005).

Mei et al. "Blood-borne human plasma cells in steady state are derived from mucosal immune responses", *Blood*, 113(11): 2461-2469 (2009).

Meijer et al. "Isolation of Human Antibody Repertoires with Preservation of the Natural Heavy and Light Chain Pairing", *J. Mol. Biol.*, 358: 764-772 (2006).

Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.

Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).

Meier, et al. "The influence of different stimulation conditions on the assessment of antigen-induced CD154 expression on CD4+ T cells", *Cytometry A.*, (11):1035-1042 (2008). doi: 10.1002/cyto.a.20640.

Meleshko, et al. "Rearrangements of IgH, TCRD and TCRG genes as clonality marker of childhood acute lymphoblastic leukemia", *Experimental Oncology*, 27(4):319-324 (2005).

Menezes et al. "A public T cell clonotype within a heterogeneous autoreactive repertoire is dominant in driving EAE", *J Clin Invest*, 117(8):2176-2185 (2007).

Metzker, "Sequencing Technologies—The Next Generation", *Nature Reviews, Genetics*, 11:31-46 (2010).

Meyer et al. "Targeted high-throughput sequencing of tagged nucleic acid samples", *Nucleic Acids Research*, 35(15): e97, 5 pages (2007).

Miceli and Parnes. "The roles of CD4 and CD8 in T cell activation", *Seminars in Immunology*, 3(3): 133-141 (1991). Abstract only.

Michálek, et al. "Detection and long-term in vivo monitoring of individual tumor-specific T cell clones in patients with metastatic melanoma", *J Immunol.*, 178(11):6789-6795 (2007).

Michálek, et al. "Identification and monitoring of graft-versus-host specific T-cell clone in stem cell transplantation", *The Lancet*, 361(9364): 1183-1185 (2003).

Miller, et al., "Assembly algorithms for next-generation sequencing data", Genomics, 95(6): 315-327 (2010).

Miltenyi, et al. "High gradient magnetic cell separation with MACS", *Cytometry*, 11(2): 231-238 (1990).

Miner et al. "Molecular barcodes detect redundancy and contamination in hairpin-bisulfite PCR", *Nucleic Acids Research*, 32(17): e135, 4 pages (2004).

Mitra, et al. "Fluorescent in situ sequencing on polymerase colonies", *Anal Biochem.*, 320(1): 55-65, Abstract Only (2003).

Mittelstadl, et al. "Thymocyte responsiveness to endogenous glucocorticoids is required for immunological fitness", J Clin Invest., 122(7):2384-94 (2012). doi: 10.1172/JCI63067. Epub Jun. 1, 2012.

Miyashita, et al. "N-Methyl substituted 2',4'—BNANC: a highly nuclease-resistant nucleic acid analogue with high-affinity RNA selective hybridization", *Chem Commun* (Camb), (36): 3765-3767, Abstract Only (2007). Epub Jul. 9, 2007.

Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).

Molloy, et al. "Soluble T cell receptors: novel immunotherapies", *Curr Opin Pharmacol.*, 5(4): 438-443 (2005) (Abstract Only).

Moody, et al. "Antigen-specific B cell detection reagents: use and quality control", *Cytometry A.*, 73(11): 1086-1092 (2008). doi: 10.1002/cyto.a.20599.

Morgan, et al. "Cancer regression in patients after transfer of genetically engineered lymphocytes", Science, 314(5796): 126-129 (2006). Epub Aug. 31, 2006.

Morozova et al. "Applications of New Sequencing Technologies for Transcriptome Analysis", *Annu. Rev. Genomics Hum. Genet.*, 10: 135-151 (2009).

Morrissy et al. "Next-generation tag sequencing for cancer gene expression profiling", *Genome Research*, 19: 1825-1835 (2009).

Moss, et al. "The human T cell receptor in health and disease", *Annu. Rev. Immunol.*, 10:71-96 (1992).

Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.

Mueller, et al. "Human Treg responses allow sustained recombinant adeno-associated virus-mediated transgene expression", J Clin Invest., 123(12): 5310-8 (2013). doi: 10.1172/JCI70314. Epub Nov. 15, 2013.

Muraro et al. "Molecular tracking of antigen-specific T cell clones in neurological immune-mediated disorders", *Brain*, 126(Pt 1):20-31 (2003).

Muraro, et al. "T cell repertoire following autologous stem cell transplantation for multiple sclerosis", J Clin Invest., 124(3): 1168-72 (2014). doi: 10.1172/JCI71691. Epub Feb. 17, 2014.

Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.

Naito, et al. "CD8+ T cells infiltrated within cancer cell nests as a prognostic factor in human colorectal cancer", *Cancer Research*, 58(16): 3491-3494 (1998).

Nakano, et al. "Single-molecule PCR using water-in-oil emulsion", *J Biotechnol.*, 102(2): 117-124, Abstract Only (2003).

Nardi, et al. "Quantitative monitoring by polymerase colony assay of known mutations resistant to ABL kinase inhibitors", *Oncogene*, 27(6):775-782 (2008). Epub Aug 6, 2007 1-8.

Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342. Epub Nov 2, 2010.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Neller, et al. "High frequency of herpesvirus-specific clonotypes in the human T cell repertoire can remain stable over decades with minimal turnover", J Virol., 87(1): 697-700 (2013). doi: 10.1128/NI.02180-12. Epub Oct. 17, 2012.

Nelson. "CD20+ B cells: the other tumor-infiltrating lymphocytes", *The Journal of Immunology*, 185(9): 4977-4982 (2010). doi: 10.4049/jimmunol.1001323.

Newman, et al. "Identification of an antigen-specific B cell population", *J Immunol Methods*, 272(1-2): 177-187, Abstract Only (2003).

Nguyen et al. "Identification of errors introduced during high throughput sequencing of the T cell receptor repertoire" *BMC Genomics*, 12: 106, 13 pages (2011).

(56) References Cited

OTHER PUBLICATIONS

Nie, et al. "Optical detection of single molecules", *Annu. Rev. Biophys. Biomol. Struct.*, 26: 567-596 (1997).
Nielsen, et al. "Peptide nucleic acid (PNA). A DNA mimic with a pseudopeptide backbone", *Chem. Soc. Rev.*, 26:73-78, Abstract Only (1997).
Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.
Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).
Nucleis product webpage, "Exonuclease I-Shrimp alkaline phosphatase clean up of PCR products," (Published on webpage 2013) Downloaded Dec. 15, 2015.
Oble, et al. "Focus on TILs: prognostic significance of tumor infiltrating lymphocytes in human melanoma", *Cancer Immunity*, 9: 3, 20 pages (2009).
O'Brian et al., "Sorting out mix-ups. The provenance of tissue sections may be confirmed by PCR using microsatellite markers", *Am. J. Clin. Pathol.*, 106(6): 758-764 (1996). (Abstract Only).
Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.
Ogle, et al. "Direct measurement of lymphocyte receptor diversity", *Nucleic Acids Research*, 31(22):e139, 6 pages (2003).
Ohtani. "Focus on TILs: prognostic significance of tumor infiltrating lymphocytes in human colorectal cancer", *Cancer Immunity*, 7: 4, 9 pages (2007).
Okajima et al. "Analysis of T cell receptor Vβ diversity in peripheral $CD4^+$ and $CD8^+$ T lymphocytes in patients with autoimmune thyroid diseases", *Clinical & Experimental Immunology*, 155:166-172 (2008).
Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.
Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).
Packer and Muraro. "Optimized clonotypic analysis of T-cell receptor repertoire in immune reconstitution", *Experimental Hematology*, 35(3):516-521 (2007).
Pagés, Franck. Tumor-associated immune parameters for personalized patient care. Sci Transl Med., 5(214):214fs42 (2013). doi: 10.1126/scitranslmed.3007942.
Palmowski, et al. "The use of HLA class I tetramers to design a vaccination strategy for melanoma patients", *Immunol Rev.*, 188: 155-163 (2002) (Abstract Only).
Palomaki, et al. "DNA sequencing of maternal plasma reliably identifies trisomy 18 and trisomy 13 as well as Down syndrome: an international collaborative study", *Genet Med.*, 14(3): 296-305 (2012). doi: 10.1038/gim.2011.73. Epub Feb. 2, 2012.
Pan, et al. "A new FACS approach isolates hESC derived endoderm using transcription factors", *PLoS One*, 6(3): e17536, 9 pages (2011). doi: 10.1371/journal.pone.0017536.
Panzer-Grümayer et al. "Immunogenotype changes prevail in relapses of young children with TEL-AML1-positive acute lymphoblastic leukemia and derive mainly from clonal selection", *Clin Cancer Research*, 11(21):7720-7727 (2005).
Parameswaran et al. "A pyrosequencing-tailored nucleotide barcode design unveils opportunities for large-scale sample multiplexing", *Nucleic Acids Research*, 35(19): e130, 9 pages (2007).
Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.
Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.
Paszkiewicz et al, "De novo assembly of short sequence reads," Briefings in Bioinformatics, 11(5): 457-472 (2010).
Payne, et al. "Peripheral blood mononuclear cells of patients with breast cancer can be reprogrammed to enhance anti-HER-2/neu reactivity and overcome myeloid-derived suppressor cells", Breast Cancer Res Treat., 142(1):45-57 (2013). doi: 10.1007/s10549-013-2733-5. Epub Oct. 25, 2013.
Peet. "The Measurement of Species Diversity", *Annual Review of Ecology and Systematics*, 5: 285-307, Abstract Only (1974).
Petrosino, et al. "Metagenomic pyrosequencing and microbial identification", *Clin Chem.*, 55(5): 856-866 (2009). doi: 10.1373/clinchem.2008.107565. Epub Mar. 5, 2009.
PCT/US2009/006053, International Search Report dated Jun. 15, 2010, 6 pages.
PCT/US2009/006053, Written Opinion dated Jun. 15, 2010, 4 pages.
PCT/US2009/006053, International Preliminary Report on Patentability dated May 10, 2011, 5 pages.
PCT/US2011/000791, International Search Report and Written Opinion dated Sep. 22, 2011, 13 pages.
PCT/US2011/000791, International Preliminary Report on Patentability dated Nov. 6, 2012, 10 pages.
PCT/US2013/028942, International Search Report and Written Opinion dated May 9, 2013, 10 pages.
PCT/US2013/028942, International Preliminary Report on Patentability dated May 5, 2015, 9 pages.
PCT/US2013/054189, International Search Report and Written Opinion dated Oct. 21, 2013, 10 pages.
PCT/US2013/054189, International Preliminary Report on Patentability dated Feb. 10, 2015, 7 pages.
PCT/US2013/035857 International Search Report and Written Opinion dated Aug. 7, 2013, 10 pages.
PCT/US2013/035857 International Preliminary Report on Patentability dated Oct. 14, 2014, 8 pages.
PCT/US2013/045276, International Search Report and Written Opinion dated Jan. 29, 2014, 11 pages.
PCT/US2013/045276 International Preliminary Report on Patentability dated Dec. 16, 2014, 2014, 7 pages.
PCT/US2013/051539 International Search Report and Written Opinion dated Nov. 27, 2013, 9 pages.
PCT/US2013/051539, International Preliminary Report on Patentability dated Jan. 27, 2015, 7 pages.
PCT/US2014/030859 International Preliminary Report on Patentability dated Sep. 15, 2015, 8 pages.
PCT/US2014/044971 International Search Report and Written Opinion dated Oct. 30, 2014, 14 pages.
PCT/US2014/044971 International Preliminary Examination Report dated Jan. 6, 2016, 12 pages.
PCT/US2015/018967, International Search Report and Written Opinion dated Jul. 30, 2015, 17 pages.
PCT/US2015/019029, International Search Report and Written Opinion dated Sep. 15, 2015, 19 pages.
PCT/US2015/023915, International Search Report and Written Opinion dated Aug. 26, 2015, 11 pages.
Pels et al. "Clonal evolution as pathogenetic mechanism in relapse of primary CNS lymphoma", *Neurology*, 63(1):167-169 (2004).
Pira et al. "Human naive CD4 T-cell clones specific for HIV envelope persist for years in vivo in the absence of antigenic challenge", *J Acquir Immune Defic Syndr.*, 40(2):132-139 (2005).
Plasilova et al. "Application of the Molecular Analysis of the T-Cell Receptor Repertoire in the Study of Immune-Mediated Hematologic Diseases", *Hematology*, 8(3): 173-181 (2003).
Polstra, et al. "Development of real-time NASBA assays with molecular beacon detection to quantify mRNA coding for HHV-8 lytic and latent genes", *BMC Infect Dis.*, 2: 18 (2002). Epub Sep. 4, 2002.
Pop and Salzberg. "Bioinformatics challenges of new sequencing technology", *NIH, Trends Genet.*, 24(3): 142-149 (2008).
Pourmand, et al. "Direct electrical detection of DNA synthesis", *PNAS*, 103(17): 6466-6470 (2006). Epub Apr. 13, 2006.

(56) References Cited

OTHER PUBLICATIONS

Polz and Cavanaugh. "Bias in Template-to-Product Ratios in Multitemplate PCR", *Applied and Environmental Microbiology*, 64(10): 3724-3730 (1998).
Porter, et al. "Chimeric antigen receptor-modified T cells in chronic lymphoid leukemia", N Engl J Med., 365(8):725-33 (2011). doi: 10.1056/NEJMoa1103849. Epub Aug. 10, 2011.
Prabakaran et al. "454 antibody sequencing—error characterization and correction", *BMC Research Notes*, 4: 404 (2011).
Putnam, et al. "Clinical grade manufacturing of human alloantigen-reactive regulatory T cells for use in transplantation", Am J Transplant., 13(11): 3010-20 (2013). doi: 10.1111/ajt.12433. EpubSep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Qu et al. "Efficient frequency-based de novo short-read clustering for error trimming in next-generation sequencing", *Genome Research*, 19: 1309-1315 (2009).
Quick. SOLiD System—a next-gen DNA sequencing platform announced, Gizmag online magazine, http://www.mizmag.com/go/8248, pp. 1-5, Oct. 2007.
Quince et al. "Removing Noise From Pyrosequenced Amplicons", *BMC Informatics*, 12: 38 (2011).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Ray, et al. "Single cell multiplex PCR amplification of five dystrophin gene exons combined with gender determination", *Molecular Human Reproduction*, 7(5): 489-494 (2001).
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Reddy and Georgiou. "Systems analysis of adaptive immunity by utilization of high-throughput technologies", *Current Opinion in Biotechnology*, 22(4): 584-589 (2011).
Reinartz et al. "Massively parallel signature sequencing (MPSS) as a tool for in-depth quantitative gene expression profiling in all organisms", *Brief Funct Genomic Proteomic.*, 1(1):95-104 (2002).
Ria, et al. "Collagen-specific T-cell repertoire in blood and synovial fluid varies with disease activity in early rheumatoid arthritis", *Arthritis Res Ther.*, 10(6):R135, 18 pages (2008). Epub Nov. 17, 2008.
Rickinson and Moss. "Human cytotoxic T lymphocyte responses to Epstein-Barr virus infection", *Annu Rev Immunol.*, 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", *Lancet*, 364:355-364 (2004).
Robert, et al. "CTLA4 blockade broadens the peripheral T-cell receptor repertoire", Clin Cancer Res., 20(9):2424-32 (2014). doi: 10.1158/1078-0432.CCR-13/2648. Epub Feb. 28, 2014.
Robins, et al. "CD4+ and CD8+ T cell β antigen receptors have different and predictable V and J gene usage and CDR3 lengths", *J. Immunol.*, 188: 115.10, Abstract (2012).
Robins et al. "Detecting and monitoring lymphoma with high-throughput sequencing" *Oncotarget*, 2:287-288 (2011).
Robins, H. et al. "Comprehensive assessment of T-cell receptor β-chain diversity in αβ T cells", *Blood*, 114(19):4099-4107 (and Supplemental Materials) (2009).
Robins, et al. "Effects of aging on the human adaptive immune system revealed by high-throughput DNA sequencing of T cell receptors", *J Immunol.*, 188: 47.16, Abstract (2012).
Robins, et al. "High-throughput sequencing of T-cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", *Curr Opin Immunol.*, 25(5): 646-652 (2013). doi: 10.1016/j.coi.2013.09.017. Epub Oct. 16, 2013.
Robins, et al. "Overlap of the human CD8+ T cell receptor repertoire." Oct. 2010. Poster. 1 page.
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Robins, H. et al. "The Computational Detection of Functional Nucleotide Sequence Motifs in the Coding Regions of Organisms", *Exp Biol Med*, 233(6): 665-673 (2008).
Ronaghi, et al. "A sequencing method based on real-time pyrophosphate", *Science*, 281(5375): 363, 365, 5 pages. (1998).
Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).
Rothberg, et al. "An integrated semiconductor device enabling non-optical genome sequencing", *Nature*, 475(7356): 348-352 (2011). doi: 10.1038/nature10242.
Rothberg et al. "The development and impact of 454 sequencing", *Nature Biotechnology*, 26(10): 1117-1124 (2008).
Rougemont, et al. "Probabilistic base calling of Solexa sequencing data", *BMC Bioinformatics*, 9:431, 12 pages (2008).
Ryan et al. "Clonal evolution of lymphoblastoid cell lines", *Laboratory Investigation*, 86(11):1193-1200 (2006). Epub Oct. 2, 2006.
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex lmmunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Sartorius Stedim Biotech product brochure, "Primer removal after a PCR reaction with Vivacon® 2", (2010).
Sato et al. "Intraepithelial CD8+ tumor-infiltrating lymphocytes and a high CD8+ Iregulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schaufelberger et al. "An uneven expression of T cell receptor V genes in the arterial wall and peripheral blood in giant cell arteritis", *Inflammation*, 31(6):372-383 (2008).
Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone. 002731 0.
Schmitt et al. "Detection of ultra-rare mutations by next-generation sequencing," *PNAS*, 109(36): 14508-14513 and Supporting Information, 9 pages (2012).

(56) References Cited

OTHER PUBLICATIONS

Schøller et al. "Analysis of T cell receptor αβ variability in lymphocytes infiltrating melanoma primary tumours and metastatic lesions", *Cancer Immunol Immunother*. 39(4):239-248 (1994).

Schreiber et al. "Cancer immunoediting: integrating immunity's roles in cancer suppression and promotion", *Science*, 331(6024): 1565-1570 (2011). doi: 10.1126/science.1203486.

Schwab et al. "CD8+ T-cell clones dominate brain infiltrates in Rasmussen encephalitis and persist in the periphery", *Brain*, 132:1236-1246 (2009).

Schweiger et al. "Genome-wide massively parallel sequencing of formaldehyde fixed-paraffin embedded (FFPE) tumor tissues for copy-number- and mutation-analysis",*PLoS One*, 4(5): e5548, 7 pages (2009). doi: 10.1371/journal.pone.0005548. Epub May 14, 2009.

Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).

Sehouli et al. "Epigenetic quantification of tumor-infiltrating T-lymphocytes" *Epigenetics*, 6(2): 236-246 (2011). Epub Feb. 1, 2011.

Seitz, et al. "Reconstitution of paired T cell receptor α- and β-chains from microdissected single cells of human inflammatory tissues", *PNAS*, 103: 12057-12062 (2006).

Seo, et al. "Four-color DNA sequencing by synthesis on a chip using photocleavable fluorescent nucleotides", *PNAS*, 102(17): 5926-5931 (2005). Epub Apr. 13, 2005.

Sequenta and iRepertoire Join Forces on Blood Cancer Testing. Business Wire. Aug. 8, 2013. http://www.businesswire.com/news/home/20130808005363/en/SequentaiRepertoire-Join-Forces-Blo...#.VGTT9WdOyUk. 2 pages.

Sfanos et al. "Human Prostate-Infiltrating CD8+ T Lymphocytes are Oligoclonal and PD-1+", *The Prostate*, 69(15): 1694-1703 (2009).

Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.

Shen et al. "Comparing platforms for *C. elegans* mutant identification using high-throughput whole-genome sequencing", *PLoS One*, 3(12):e4012, 6 pages (2008).

Shendure, et al. "Accurate multiplex polony sequencing of an evolved bacterial genome", *Science*, 309(5741): 1728-1732, Abstract Only (2005). Epub Aug. 4, 2005.

Shendure, et al. "Advanced sequencing technologies: methods and goals", *Nat Rev Genet.*, 5(5): 335-344 (2004).

Shendure and JI. "Next-generation DNA sequencing", *Nature Biotechnology*, 26(10):1135-1145 (2008).

Sherwood, A. et al. "Deep Sequencing of the Human TCRγ and TCRβ Repertoires Suggests that TCR β Rearranges After αβ and γδ T Cell Commitment", Science Translational Medicine, *Sci. Transl. Med.*, 3(90): 1-7 (2011).

Sherwood, et al. "New Technologies for Measurements of Tumor Infiltrating Lymphocytes", Presented Nov. 7, 2012 Moscone Center, Exhibit Halls ABC.

Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.

Shino, et al. "Usefulness of immune monitoring in lung transplantation using adenosine triphosphate production in activated lymphocytes", *The Journal of Heart and Lung Transplant*, 31: 996-1002 (2012).

Shiroguchi et al. "Digital RNA sequencing minimizes sequence-dependent bias and amplification noise with optimized single-molecule barcodes", *PNAS*, 109(4): 1347-1352 (2012).

Shoemaker et al. "Quantitative phenotypic analysis of yeast deletion mutants using a highly parallel molecular bar-coding strategy," *Nature Genetics*, 14(4): 450-456 (1996).

Shumaker et al. "Mutation detection by solid phase primer extension", *Hum Mutat.*, 7(4): 346-354, Abstract Only (1996).

Sia, et al. "Microfluidic devices fabricated in poly(dimethylsiloxane) for biological studies", *Electrophoresis*, 24(21): 3563-3576, Abstract Only (2003).

Sims, et al. "Fluorogenic DNA sequencing in PDMS microreactors", *Nat Methods*, 8(7): 575-580 (2011). doi: 10.1038/nmeth.1629.

Sims, et al. "MHC-peptide tetramers for the analysis of antigen-specific T cells", *Expert Rev Vaccines*, 9(7): 765-774 (2010). doi: 10.1586/erv.10.66.

Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", *Hepatology*, 33(5):1288-1298 (2001).

Singapore Application No. 11201407888R, Written Opinion dated Aug. 14, 2015, 12 pages.

Singapore Application No. 11201500313Y, Search Report and Written Opinion dated Dec. 9, 2015, 11 pages.

Skulina et al. "Multiple Sclerosis: Brain-infiltrating $CD8^+$ T cells persist as clonal expansions in the cerebrospinal fluid and blood", *PNAS*, 101(8):2428-2433 (2004).

Smith, et al. "Comparison of biosequences", *Advances in Applied Mathematics*, 2: 482-489 (1981).

Smith et al. "Rapid generation of fully human monoclonal antibodies specific to a vaccinating antigen", *Nature Protocols*, 4(3): 372-384 and Corrigenda (2009).

Smith et al. "Rapid whole-genome mutational profiling using next-generation sequencing technologies", *Genome Research*, 18: 1638-1642 (2008).

Smith et al. "Quantitative phenotyping via deep barcode sequencing", *Genome Research*, 19: 1836-1842 (2009).

Smith et al, "Using quality scores and longer reads improves accuracy of Solexa read mapping," BMC Bioinformatics, 9: 128 (2008).

Sobrino, et al. "SNPs in forensic genetics: a review on SNP typing methodologies", *Forensic Sci Int.*, 154(2- 3): 181-194, Abstract Only (2005). Epub Jan. 11, 2005.

Spreafico, et al. "A circulating reservoir of pathogenic-like CD4+ T cells shares a genetic and phenotypic signature with the inflamed synovial micro-environment", *Ann Rheum Dis.*, 0: 1-7 (2014). doi: 10.1136/annrheumdis-2014-206226. [Epub ahead of Print].

Sramkova, et al. "Detectable minimal residual disease before allogeneic hematopoietic stem cell transplantation predicts extremely poor prognosis in children with acute lymphoblastic leukemia", *Pediatr. Blood Cancer*, 48(1):93-100 (2007).

Srinivasan et al. "Effect of fixatives and tissue processing on the content and integrity of nucleic acids", *Am J Pathol.*, 161(6): 1961-1971 (2002).

Srivastava and Robins. "Palindromic nucleotide analysis in human T cell receptor rearrangements", PLoS One, 7(12):e52250 (2012). doi: 10.1371/joumal.pone.0052250. Epub Dec. 21, 2012.

Stanley. Essentials of Immunology & Serology, Delmar, Thomson Learning, Chapter 7, T cells, p. 95 (2002).

Steenbergen, et al. "Distinct ongoing Ig heavy chain rearrangement processes in childhood B-precursor acute lymphoblastic leukemia", *Blood*, 82(2):581-589 (1993).

Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).

Stemmer, et al. "Single-step assembly of a gene and entire plasmid from large numbers of oligodeoxyribonucleotides", *Gene*, 164(1): 49-53 (1995).

Steward et al. "A polymerase chain reaction study of the stability of Ig heavy-chain and T-cell receptor delta gene rearrangements between presentation and relapse of childhood B-lineage acute lymphoblastic leukemia", *Blood*, 83(5):1355-1362 (1994).

Stewart and Schwartz. "Immunoglobulin V regions and the B cell", *Blood*, 83(7): 1717-1730 (1994).

Stickler, et al. "An in vitro human cell-based assay to rank the relative immunogenicity of proteins", *Toxicol Sci.*, 77(2): 280-289 (2004). Epub Dec. 22, 2003.

(56) References Cited

OTHER PUBLICATIONS

Stiller et al. "Direct multiplex sequencing (DMPS)—a novel method for targeted high-throughput sequencing of ancient and highly degraded DNA", *Genome Research*, 19: 1843-849 (2009).
Stratton. "Exploring the genomes of cancer cells: progress and promise", *Science*, 331(6024): 1553-1558 (2011). doi: 10.1126/science.1204040.
Striebich, et al. "Selective Accumulation of Related CD41 T Cell Clones in the Synovial Fluid of Patients with Rheumatoid Arthritis", *J Immunol.*, 161(8): 4428-36 (1998).
Struyk et al. "T cell receptors in rheumatoid arthritis", *Arthritis & Rheumatism*, 38(5):577-589 (1995).
Sumida et al. "T cell receptor repertoire of infiltrating T cells in lips of Sjögren's syndrome patients", *J Clin Invest.*, 89:681-685 (1992).
Sumida et al. "T cell receptor Va repertoire of infiltrating T cells in labial salivary glands from patients with Sjögren's syndrome", *J Rheumatol.*, 21:1655-1661 (1994).
Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.
Szczepanski et al. "Comparative analysis of Ig and TCR gene rearrangements at diagnosis and at relapse of childhood precursor-B-ALL provides improved strategies for selection of stable PCR targets for monitoring of minimal residual disease", *Blood*, 99(7):2315-2323 (2002).
Szczepanski et al. "Why and how to quantify minimal residual disease in acute lymphoblastic leukemia?", *Leukemia*, 21(4):622-626 (2007). Epub Feb. 15, 2007.
Tackenberg et al. "Clonal expansions of CD4+ β helper T cells in autoimmune myasthenia gravis", *European Journal of Immunology*, 37(3):849-863 (2007).
Tajiri et al. "Cell-microarray analysis of antigen-specific B-cells: single cell analysis of antigen receptor expression and specificity", *Cytometry Part A*, 71A: 961-967 (2007).
Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).
Taubenheim et al. "High Rate of Antibody Secretion Is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
Ten Bosch et al. "Keeping Up With the Next Generation Massively Parallel Sequencing in Clinical Diagnostics", *Journal of Molecular Diagnostics*, 10(6): 484-492 (2008).
Thiel, et al. "Antigen-specific cytometry—new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Tokimitsu et al. "Single lymphocyte analysis with a microwell array chip", *Cytometry Part A*, 71A:1003-1010 (2007).
Toriello et al. "Integrated microfluidic bioprocessor for single-cell gene expression analysis", *PNAS*, 105(51): 20173-20178 (2008).
Tsai et al. "Discovery of rare mutations in populations: TILLING by sequencing", Plant Physiology, 156(3): 1257-1268 (and Supplemental Data) (2011).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Turcotte and Rosenberg. "Immunotherapy for metastatic solid cancers", *Adv Surg.*, 45: 341-360 (2011).
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 27, 2011 for UK application No. GB1105068.9.
UK Search Report and office action dated Jan. 13, 2012 for UK application No. GB1120209.0.
UK Search Report and office action dated Jul. 7, 2010 for UK application No. GB1009641.0.
Umibe et al. "Clonal expansion of T cells infiltrating in the airways of non-atopic asthmatics", *Clinical & Experimental Immunology*, 119(3):390-397 (2000).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Urquhart, et al. "Rate-controlled delivery systems in drug and hormone research", *Annu Rev Pharmacol Toxicol.*, 24: 199-236, Abstract Only (1984).
Vanderborght, et al. "Dynamic T cell receptor clonotype changes in synovial tissue of patients with early rheumatoid arthritis: effects of treatment with cyclosporin A (Neoral)", *J Rheumatol.*, 29(3): 416-426 (2002).
Varley and Mitra. "Nested patch PCR enables highly multiplexed mutation discovery in candidate genes", *Genome Research*, 18: 1844-1850 (2008).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Vester, et al. "LNA (locked nucleic acid): high-affinity targeting of complementary RNA and DNA", *Biochemistry*, 43(42): 13233-13241, Abstract Only (2004).
Vlassov, et al. "Circulating nucleic acids as a potential source for cancer biomarkers", *Curr Mol Med.*, 10(2): 142-165 (2010).
Vogelstein et al. "Cancer genome landscapes", *Science*, 339(6127): 1546-1558 (2013). doi: 10.1126/science.1235122.
Wälchli, et al. "A practical approach to T-cell receptor cloning and expression", *PLoS One*, 6(11): e27930, 11 pages. (2011). doi: 10.1371/journal.pone.0027930. Epub Nov. 21, 2011.
Wang, et al. "Balanced-PCR amplification allows unbiased identification of genomic copy changes in minute cell and tissue samples", *Nucleic Acids Research*, 32(9): e76, 10 pages (2004).
Wang, et al. "High throughput sequencing reveals a complex pattern of dynamic interrelationships among human T cell subsets", *PNAS*, 107(4): 1518-1528 (2010).
Wang, et al. "HIV integration site selection: Analysis by massively parallel pyrosequencing reveals association with epigenetic modifications", *Genome Research*, 17(8): 1186-1194 (2007). EpubJun. 1, 2007.
Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.
Warren et al. "Exhaustive T-cell repertoire sequencing of human peripheral blood samples reveals signatures of antigen selection and a directly measured repertoire size of at least 1 million clonotypes", *Genome Res.*, 21(5): 790-797 (2011). doi: 10.1101/gr.115428.110. Epub Feb. 24, 2011.
Warren et al. "Profiling model T-cell metagenomes with short reads", *Bioinformatics*, 25(4):458-464 (2009).

(56) References Cited

OTHER PUBLICATIONS

Weinstein, J.A. et al. "High-Throughput Sequencing of the Zebrafish Antibody Repertoire", *Science*, 324(5928): 807-810, Supporting/Supplementary Materials (2009).
Weiss et al. "Clonal Rearrangements of T-Cell Receptor Genes in Mycosis Fungoides and Dermatopathic Lymphadenopathy", *The New England Journal of Medicine*, 313(9):539-544 (1985).
Welch and Link. "Genomics of AML: clinical applications of next-generation sequencing", *American Society of Hematology*, 2011: 30-35 (2011). doi: 10.1182/asheducation-2011.1.30.
Wells, et al. "Rapid evolution of peptide and protein binding properties in vitro", *Curr Opin Biotechnol.*, 3(4): 355-362, Abstract Only (1992).
Wells, et al. "Strategies for preimplantation genetic diagnosis of single gene disorders by DNA amplification", *Prenatal Diagnosis*, 18(13):1389-1401 (1998).
Weng, et al. "Minimal residual disease monitoring with high-throughput sequencing of T cell receptors in cutaneous T cell lymphoma", Sci Transl Med., 5(214):214ra171 (2013). doi: 10.1126/scitranslmed.3007420.
Westermann and Pabst. "Distribution of lymphocyte subsets and natural killer cells in the human body", *Clin Investig.*, 70(7): 539-544 (1992).
Wetmur and Chen. "An emulsion polymerase chain reaction-based method for molecular haplotyping", *Methods in Molecular Biology*, 410: 351-361 (1996).
Wetmur and Chen. "Linking emulsion PCR haplotype analysis", chapter 11, Park, D.J. (ed.), *PCR Protocols, Methods in Molecular Biology*, 687: 165-175 (2011).
Wetmur et al. "Molecular haplotyping by linking emulsion PCR: analysis of paraoxonase 1 haplotypes and phenotypes", *Nucleic Acids Research*, 33(8):2615-2619 (2005).
Weusten, et al. "Principles of quantitation of viral loads using nucleic acid sequence-based amplification in combination with homogeneo detection using molecular beacons", Nucleic Acids Res., 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Williams, et al. "Amplification of complex gene libraries by emulsion PCR", *Nat Methods*, 3(7): 545-550 (2006).
Wlodarski et al. "Molecular strategies for detection and quantitation of clonal cytotoxic T-cell responses in aplastic anemia and myelodysplastic syndrome", *Blood*, 108(8):2632-2641 (2006).
Wlodarski et al. "Pathologic clonal cytotoxic T-cell responses: nonrandom nature of the T-cell-receptor restriction in large granular lymphocyte leukemia", *Blood*, 106:2769-2779 (2005).
Wolda. "Similarity Indices, Sample Size and Diversity", *Oecologia* (Berl), 50:296-302 (1981).
Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Wrammert et al. "Rapid cloning of high-affinity human monoclonal antibodies against influenza virus", *Nature*, 453: 667-672 (2008).
Wu, et al. "High-throughput sequencing detects minimal residual disease in acute T lymphoblastic leukemia", Sci Transl Med., 4(134):134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu et al. "Focused Evolution of HIV-1 Neutralizing Antibodies Revealed by Structures and Deep Sequencing", *Science*, 333: 1593-1602 (2011).
Xiong, et al. "Chemical gene synthesis: strategies, softwares, error corrections, and applications", *FEMS Microbiol Rev.*, 32(3): 522-540 (2008). doi: 10.1111/j.1574-6976.2008.00109.x. Epub Apr. 2, 2008.
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
Yao, et al. "Analysis of the CDR3 length repertoire and the diversity of TCRα chain in human peripheral blood T Lymphocytes", Cell Mol Immunol., 4(3): 215-220 (2007).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).
Yon and Fried. "Precise gene fusion by PCR", *Nucleic Acids Research*, 17(12):4895, 1 page (1989).
York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.
Yu and Fu. "Tumor-infiltrating T lymphocytes: friends or foes?", *Lab Invest.*, 86(3): 231-245 (2006).
Zagnoni, et al. "Droplet Microfluidics for High-throughput Analysis of Cells and Particles", *Methods in Cell Biology*, Chapter 2, 102: 23-48 (2011).
Zaliova, et al. "Quantification of fusion transcript reveals a subgroup with distinct biological properties and predicts relapse in BCR/ABL-positive ALL: implications for residual disease monitoring", *Leukemia*,23(5):944-951 (2009).
Zehentner et al. "Minimal Disease Detection and Confirmation in Hematologic Malignancies: Combining Cell Sorting with Clonality Profiling", *Clinical Chemistry*, 52(3): 430-437 (2006).
Zeng et al. "High-performance single cell genetic analysis using microfluidic emulsion generator arrays", *Anal. Chem.*, 82(8):3183-3190 (2010).
Zhou et al. "High throughput analysis of TCR-β rearrangement and gene expression in single cells", *Laboratory Investigation*, 86: 314-321 (2006).
Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.
Zhu, et al. "Immune surveillance by CD8αα+ skin-resident T cells in human herpes virus infection", Nature, 497(7450):494-7 and Corrigendum (2013). doi: 10.1038/nature12110. Epub May 8, 2013.
Zimmerman and Mannhalter. "Technical aspects of quantitative competitive PCR", *Biotechniques*, 21: 268-279 (1996).
Chinese Patent Application No. 201510054401.X, Search Report dated Jul. 14, 2016, 2 pages.
European Application No. 16162568.6, Extended European Search Report dated Jul. 20, 2016, 6 pages.
European Patent Application No. 10732172.1 (EP Patent No. 2387627), EPO's Communication with Notice of Opposition, dated Jan. 4, 2017, filed by Ablynx, 26 pages.
European Patent Application No. 14819680.1, Extended European Search Report dated Feb. 10, 2017, 10 pages.
European Patent Application No. 16165939.6, Extended European Search Report dated Oct. 7, 2016, 9 pages.
Ilakovac, V., "Statistical hypothesis testing and some pitfalls." Biochemia Medica (2009); 19(1): 10-16, 4 pages, [online]. [Retrieved

(56) References Cited

OTHER PUBLICATIONS on Apr. 12, 2016]. Retrieved from the Internet: <URL:http://www.biochemia-medica.com/contentlstatistical-hypothesis-testing-and-some-pitfalls>PDF.
Klarenbeek, P.L. et al. "Deep sequencing of antiviral T-cell responses to HCMV and EBV in humans reveals a stable repertoire that is maintained for many years." PLoS Pathogens (2012); 8.9: e1002889.
PCT/US2015/019029, International Preliminary Report on Patentability dated Sep. 6, 2016, 14 pages.
PCT/US2015/023915, International Preliminary Report on Patentability dated Oct. 4, 2016, 7 pages.
PCT/US2015/058035, International Preliminary Report on Patentability dated May 2, 2017, 8 pages.
PCT/US2016/019343, International Search Report and Written Opinion dated Jul. 22, 2016, 23 pages.
PCT/US2016/025535, International Search Report and Written Opinion dated Jul. 11, 2016, 9 pages.
Schwartzman, Armin. "Empirical null and false discovery rate inference for exponential families." The Annals of Applied Statistics (2008); 2(4): 1332-1359.
Woodsworth, Daniel J., et al., "Sequence analysis of T-cell repertoires in health and disease." Genome Medicine (2013); 5: 98, 13 pages.
Xie, Yang, et al., "A note on using permutation-based false discovery rate estimates to compare different analysis methods for microarray data." Bioinformatics (2005); 21.23: 4280-4288.
Cha et al., "Improved Survival with T Cell Clonotype Stability After Anti-CTLA-4 Treatment in Cancer Patients." Sci Transl Med (2014); 6(238): 238ra70.
Chinese Patent Application No. 2014800254909, Search Report and English translation, dated May 25, 2017, mailed by the Chinese Patent Office dated Jun. 6, 2017, 5 pages.
European Patent Application No. 16183402.3, Extended European Search Report dated Feb. 21, 2017, 8 pages.
European Patent Application No. 15772627.4, Extended European Search Report dated Jul. 19, 2017, 8 pages.
PCT/US2015/018967, International Preliminary Report on Patentability dated Oct. 18, 2016, 11 pages.
Van Heijst, J.W.J., et al., "Quantitative assessment of T-cell repertoire recovery after hematopoietic stem cell transplantation." Nat Med. (2013); 19(3): 372-377.
Wilson-Lingardo et al., "Deconvolution of Combinatorial Libraries for Drug Discovery: Experimental Comparison of Pooling Strategies." J. Med. Chem., (1996); 39 (14): 2720-2726.
Bonilla, F.A. et al., "Adaptive Immunity." J. Allergy Clin. Immunol. (2010); 125: S33-S40.
Dueñas and Borrebaeck, "Clonal Selection and Amplification of Phage Displayed Antibodies by Linking Antigen Recognition and Phage Replication." Bio/Technology (1994);12 (10): 999-1002.
European Patent Application No. 15779750.7, Extended European Search Report dated Aug. 9, 2017, 9 pages.
European Patent Application No. 15758762.7, Extended European Search Report dated Sep. 22, 2017, 12 pages.
European Patent Application No. 15854358.7, Extended European Search Report dated Mar. 12, 2018, 12 pages.
Födinger et al., "Multiplex PCR for rapid detection of T-cell receptor-gamma chain gene rearrangements in patients with lymphoproliferative diseases." British Journal of Haematology (1996); 94(1): 136-139.
Georgiou, G., et al., "The promise and challenge of high-throughput sequencing of the antibody repertoire." Nat Biotechnol (2014); 32(2): 158-168.
Howie, et al., "High throughput pairing of T cell receptor α and β sequences." Science Translational Medicine (2015); 7(301): 301ra131, and supplementary materials, 19 pages.
Panzara, et al., "Analysis of the T cell repertoire using the PCR and specific oligonucleotide primers." Biotechniques (1992); 12(5): 728-735.
PCT/US2016/019343, International Preliminary Report on Patentability dated Aug. 29, 2017, 14 pages.
PCT/US2016/025535, International Preliminary Report on Patentability dated Oct. 3, 2017, 7 pages.
Sotomayor, et al., "Conversion of tumor-specific $CD4^+$ T-cell tolerance to T-cell priming through in vivo ligation of CD40." Nature Medicine (1999); 5(7): 780-787.
Szczepek, et al., "A high frequency of circulating B cells share clonotypic Ig heavy-chain VDJ rearrangements with autologous bone marrow plasma cells in multiple myeloma, as measured by single-cell and in situ reverse transcriptase-polymerase chain reaction." Blood (1998); 92(8): 2844-2855.
Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements." Am J Pathol. (2001); 158(5): 1851-1857.
Yagi, et al., "Detection of clonotypic IGH and TCR rearrangements in the neonatal blood spots of infants and children with B-cell precursor acute lymphoblastic leukemia." Blood (2000); 96(1): 264-268.
Bidwell, "Advances in DNA-based HLA-typing methods." Immunol Today (Jul. 1994); 15 (7): 303-307.
Du and Egholm, "The Next-Generation Genome Sequencing: 454/Roche GC FLX." Next-Generation Genome Sequencing: Towards Personalized Medicine, Wiley-VCH Verlag GmbH & Co., KGaA (2008); (ed. Michal Janitz), Chapter 4: pp. 43-56, 34 pages.
European Patent Application No. 16756268.5, Extended European Search Report dated Oct. 22, 2018, 20 pages.
European Patent Application No. 16756268.5, Partial Supplementary European Search Report dated Jun. 19, 2018, 21 pages.
European Patent Application No. 16774304.6, Extended European Search Report dated Oct. 15, 2018, 9 pages.
European Patent Application No. 18153536.0, Extended European Search Report dated Jun. 6, 2018, 7 pages.
European Patent Application No. 18184843.3, Extended European Search Report dated Aug. 13, 2018, 10 pages.
European Patent No. EP 2387627 (Application No. 10732172.1), EPO Communication dated Oct. 29, 2018 with Grounds of Appeal filed by Ablynx NV, dated Oct. 24, 2018, 62 pages.
European Patent No. EP 2387627 (Application No. 10732172.1), Interlocutory Decision issued by the European Patent Office, dated Jun. 15, 2018, (Opposition Proceedings filed by Ablynx NV), 17 pages.
European Patent No. EP 2387627 (Application No. 10732172.1), Notice of Opposition filed by Ablynx NV, dated Dec. 22, 2016, 34 pages.
Koumi, et al., "Evaluation and validation of the ABI 3700, ABI 3100, and the MegaBACE 1000 capillary array electrophoresis instruments for use with short tandem repeat microsatellite typing in a forensic environment." Electrophoresis (Jul. 2004); 25 (14): 2227-2241.
Mardis, E.R., "The impact of next-generation sequencing technology on genetics." Cell Press (2008); 24 (3): 133-141.
Miqueu, P., et al., "Analysis of the peripheral T-cell repertoire in kidney transplant patients." Eur J Immunol. (Nov. 2010); 40(11): 3280-3290. Epub Oct. 27, 2010.
Spellman, et al., "Advances in the selection of HLA-compatible donors: refinements in HLA typing and matching over the first 20 years of the National Marrow Donor Program Registry." Biol Blood Marrow Transplant (2008); (9 Suppl):37-44. Epub Jun. 20, 2008.
U.S. Appl. No. 61/145,039, filed Jan. 15, 2009, entitled "Adaptive Immunity Profiling and Methods for Generation of Monoclonal Antibodies", Inventor—Steven R. Wiley, 40 pages.

\* cited by examiner

Figure 3A

1: Overlay primer sequences onto raw sequences

2: Group by inter-primer sequences and decode primer barcodes to identify sample source

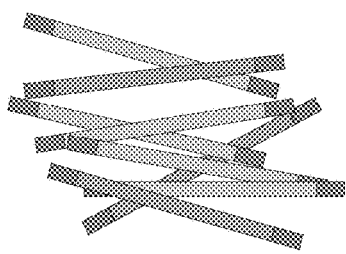

3: Create score-matrix for set of inter-primer sequences

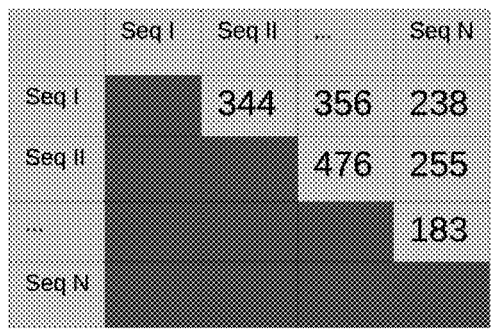

4: Create phylogenetic tree based on score matrix using algomerative clustering method; e.g. UPGMA

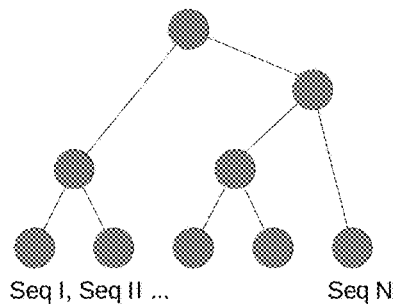

5: Calculate e-score of foreground vs background sample set counts at each node

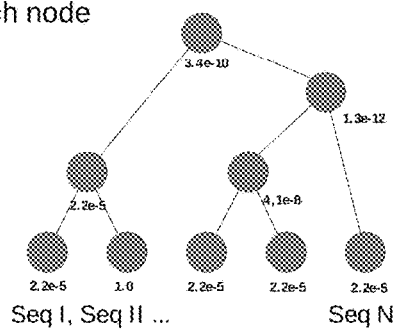

6: Identify local peak nodes; lowest e-score (maximum specificity).

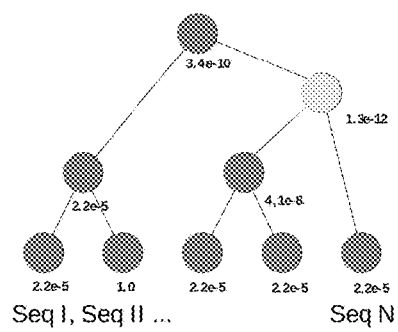

ADAPTIVE IMMUNITY PROFILING AND METHODS FOR GENERATION OF MONOCLONAL ANTIBODIES

CROSS REFERENCE TO RELATED APPLICATION

This application is a continuation of U.S. application Ser. No. 13/144,645, filed on Sep. 21, 2011 and issued as U.S. Pat. No. 8,685,898, which is a National Stage of International Application No. PCT/US2010/021264, filed on Jan. 15, 2010, which claims the benefit of U.S. Application No. 61/145,039, filed Jan. 15, 2009, which are hereby incorporated by reference in their entireties.

FIELD

The invention relates to the field of immunology, and in particular to adaptive immunity profiling and methods of producing monoclonal antibodies.

BACKGROUND

The existing methods for creating therapeutic monoclonal antibodies are primarily hybridoma, phage display, B cell isolation and antibody sequence rescue, followed if necessary by humanization of the antibody. The humanization step can be eliminated by using transgenic animals which are capable of themselves generating human antibodies.

The hybridoma method involves isolating large numbers of B cells from an immunized organism which are then fused with a myeloma tumor cell. These cells are then screened for individual cells producing antibodies with the desired properties. Once a particular hybridoma of interest is detected, a cDNA encoding the antibody is isolated and sequenced by standard molecular biology techniques, followed by a process of humanization. Humanization is the process of placing the variable region of the antibody, usually from a mouse or rabbit, into a human antibody backbone so that the resulting molecule is less immunogenic when used as a therapeutic agent in a human host. Hybridoma technology is limited by its low efficiency; the need for large numbers of B cells, which are generally obtained by sacrificing mice and harvesting from them splenic B cells; and the relative instability of the hybridomas themselves.

Phage display is a technology that uses a library of recombinant phage which present on their surface randomly paired variable domains of heavy and light chain antibodies taken from human donors. The phages are panned against the antigen of interest and those which specifically bind are amplified and the process is repeated. After multiple rounds of panning, representative phages' DNA are isolated and sequenced. The variable domains are then transferred into Ig constant region backbones. This technology often requires artificial affinity maturation in order to generate antibodies of sufficient affinity, which involves making a series of point mutations and retesting the affinity of the resulting antibodies. Moreover, the panning process is quite laborious and is often performed using robotics.

B cell isolation and antibody sequence rescue techniques involve isolating individual or small numbers of B cells and culturing them in vitro in order to create small amounts of conditioned supernatants which can be used to screen for antibodies with the desired properties. The selected lymphocyte antibody method (SLAM) is one aspect of this technology. Once an antibody with the desired properties is detected, the antibody's heavy and light chain are recovered from the cell or cells by standard molecular techniques such as PCR, and the resulting antibody is then humanized in the same manner as a hybridoma-derived antibody.

The methods currently available for the generation of monoclonal antibodies are laborious, time consuming, and subject to inaccuracy. Thus, there remains a need in the art for an efficient, easy, and accurate method for generating monoclonal antibodies.

SUMMARY

The present disclosure addresses long-felt needs in the field of immunology by providing a novel, efficient, and accurate method for producing high affinity monoclonal antibodies. The methods of the present disclosure are faster and less laborious than any existing technology for generating monoclonal antibodies. Using this method, sequence data can be generated in several days as compared to the weeks or months required by the other methods. Furthermore, since only small amounts of DNA are needed according to the present methods, data can be generated by non-invasive and non-lethal means which enables repeated sampling of the immunized organism and also allows the technique to be applied directly to human patients.

The adaptive immune system responds to changes in exposure of an organism to different pathogen and disease states by creating immune cells which are differentiated to respond to particular antigens. This occurs by genomic rearrangement at certain loci which in turn generates a wide variety of proteins not coded directly in the germline genomic DNA. Such regions subject to this kind of rearrangement include the Ig heavy and light chain variable domains, and the T-cell receptor alpha and beta variable domain regions. Once exposed to antigens which induce these changes, the cells which react to them will exist in the organism for years, and can rapidly proliferate in response to re-exposure to the antigen. In this way a record of antigen exposure is maintained in the host. This present disclosure describes a method to extract this information in order to create therapeutically useful monoclonal antibodies.

The present disclosure provides methods for producing monoclonal antibodies by applying new molecular and proteomic technologies with a novel method of data analysis.

Blood samples from immunized organisms are used to generate MPSS libraries profiling genes which are subject to rearrangement by the adaptive immune system, including but not limited to, the Ig heavy chain variable region.

According to one aspect, the present disclosure provides methods for producing monoclonal antibodies, the method comprising the steps of: (a) immunizing a host subject with an antigen; (b) creating a cDNA sequence library, the creating comprising the steps of: (i) isolating lymphocytes from the host subject, (ii) isolating mRNA from the lymphocytes, (iii) reverse transcribing the mRNA to cDNA, (iv) amplifying target antibody cDNA sequences, and (v) sequencing the target antibody cDNA sequences; and (c) analyzing the frequency of target antibody cDNA sequences, wherein target antibody cDNA sequences having a relatively high frequency are identified as candidate antibody sequences.

According to certain aspects, the lymphocytes comprise B cells and T cells. According to further aspects, the lymphocytes comprise isolated B cells. In some aspects, methods are provided wherein the relative frequencies of target antibody cDNA sequences are compared before and after exposure to the antigen, wherein target antibody cDNA sequences having a significantly higher frequency after exposure to the antigen are identified as candidate antibody sequences.

In further aspects, a host subject is re-immunized with the antigen, a cDNA sequence library is created after the re-immunization, and the relative frequencies of the target antibody sequences are compared before and after the re-immunization, wherein antibody sequences present at a significantly higher frequency after the re-immunization are identified as mature candidate antibody sequences.

In some aspects, methods are provided wherein the relative frequencies of target antibody cDNA sequences are compared at two or more times after exposure to the antigen, wherein target antibody cDNA sequences having a significantly lower frequency in later times are identified as candidate antibody sequences.

In some aspects, the target antibody sequences comprise immunoglobulin (Ig) heavy chain variable domain sequences. In further aspects the target antibody sequences comprise sequences of one or more complementarity determining regions (CDRs) of an immunoglobulin (Ig) heavy chain variable domain. In various aspects, a candidate antibody sequences with a light chain variable domain sequence and an Ig framework to produce a set of candidate monoclonal antibodies. In some aspects, the Ig framework is a human Ig framework.

According to certain aspects, the present disclosure provides methods for assaying the candidate monoclonal antibodies for affinity to an antigen. In further aspects, the present disclosure provides for subjecting the candidate monoclonal antibodies to positive selection to identify high affinity monoclonal antibodies. In yet further aspects, subjecting the candidate monoclonal antibodies to positive selection comprises contacting the candidate monoclonal antibodies to the antigen bound to a substrate and isolating bound antibodies from unbound antibodies. In certain aspects, the candidate monoclonal antibodies bind to an antigen with an affinity of at least $1 \times 10^{10}$ liter/mole, measured as an association constant ($K_{aff}$).

According to certain aspects, the present disclosure provides methods for sequencing the high affinity monoclonal antibodies. In further aspects, the relative frequencies of target antibody sequences are analyzed using a bioinformatics software algorithm. In yet further aspects the amplified target cDNA sequences are sequenced by massively parallel signature sequencing (MPSS).

In certain aspects, the host subject is an experimental animal. In some aspects, the host subject is a transgenic animal expressing human antibodies. In further aspects the host subject is a human patient that has been exposed to an antigen or a pathogen or is suffering from a disease which alters the adaptive immune response.

According to certain aspects, the present disclosure provides that a host subject is immunized with multiple antigens. In further aspects, the monoclonal antibody is reactive to multiple antigens.

According to certain aspects, the present disclosure provides methods for administering a background antigen and selecting against antibodies that are reactive to the background antigen. In further aspects, the background antigen is administered after a first antigen.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

DETAILED DESCRIPTION

Figure 1:
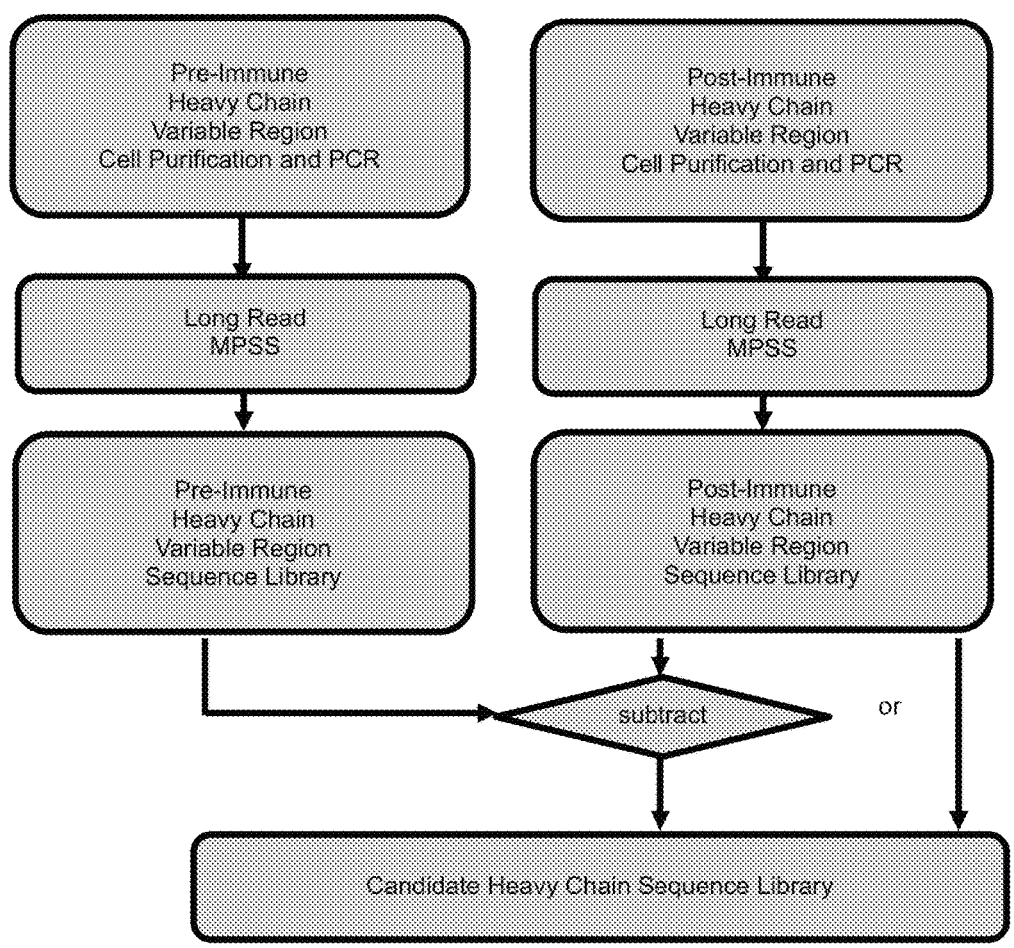
FIG. 1: Heavy Chain Sequence Library Generation. This figure illustrates an example process by which candidate antigen-specific variable chain regions can be generated. MPSS data is generated for a specific isotype of the Ig heavy chain variable region before and after exposure to antigen. These data are digitally analyzed in order to identify those sequences which have been generated in response to antigen exposure.

The present disclosure generally provides a novel, efficient, and accurate method for producing high affinity monoclonal antibodies. The methods of the present disclosure are faster and less laborious than any existing technology for generating monoclonal antibodies.

A person skilled in the art will appreciate that the present disclosure can be practiced without undue experimentation according to the methods given herein. The methods, techniques and chemicals are as described in the references given or from protocols in standard biotechnology and molecular biology textbooks.

The Figures and the following description relate to preferred aspects by way of illustration only. It should be noted that from the following discussion, alternative aspects disclosed herein will be readily recognized as viable alternatives that can be employed without departing from the principles of what is claimed.

It should be noted that the language used herein has been principally selected for readability and instructional purposes, and it can not have been selected to delineate or circumscribe the inventive subject matter. Accordingly, the disclosure is intended to be illustrative, but not limiting, of the scope of claimed methods.

As used in this specification and the appended claims, the singular forms "a", "an" and "the" include plural referents unless the content clearly dictates otherwise. Thus, for example, reference to "an antibody" includes a combination of two or more antibodies, and the like.

Any terms not directly defined herein shall be understood to have the meanings commonly associated with them as understood within the art of the present disclosure. Certain terms are discussed herein to provide additional guidance to the practitioner in describing the compositions, devices, methods and the like of aspects of the present disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the present disclosure herein.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Patient", "subject" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

The term "sufficient amount" means an amount sufficient to produce a desired effect, e.g., an amount of antigen sufficient to give rise to an immune response in a host.

The term "isolated" means a biological component, such as a cell, group of cells, nucleic acid, peptide or protein, that has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids.

The term "sample," is used in its broadest sense. A biological sample suspected of containing nucleic acids encoding at least one monoclonal antibody, or fragments thereof, or at least one monoclonal antibody itself and which sample can comprise a bodily fluid, an extract from a cell, chromosome, organelle, or membrane isolated from a cell, a cell, genomic DNA, RNA, or cDNA (in solution or bound to a solid support), a tissue, a tissue print, and the like.

As used herein any reference to "one aspect" or "an aspect" means that a particular element, feature, structure, or characteristic described in connection with the aspect is included in at least one aspect. The appearances of the phrase "in one aspect" in various places in the specification are not necessarily all referring to the same aspect.

The terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the aspects herein. This is done merely for convenience and to give a general sense of the invention. This description should be read to include one or at least one and the singular also includes the plural unless it is obvious that it is meant otherwise.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The present disclosure includes, but is not limited to, a method to derive monoclonal antibodies from an immunized organism. The organism can be an experimental organism treated with the antigen and appropriate adjuvant, or exposed to a pathogen or other biological agent. The organism can also be a human patient suffering from exposure to a pathogen or a disease. Since the method requires only small amounts of blood or tissue, the same organism can be sampled multiple times and subject to the following described analysis.

According to one aspect, the present disclosure provides methods for producing a monoclonal antibodies, the method comprising the steps of: (a) immunizing a host subject with an antigen; (b) creating a cDNA sequence library, the creating comprising the steps of: (i) isolating lymphocytes from the host subject, (ii) isolating mRNA from the lymphocytes, (iii) reverse transcribing the mRNA to cDNA, (iv) amplifying target antibody cDNA sequences, and (v) sequencing the target antibody cDNA sequences; and (c) analyzing the frequency of target antibody cDNA sequences, wherein target antibody cDNA sequences having a relatively high frequency are identified as candidate antibody sequences.

According to certain aspects, the lymphocytes comprise B cells and T cells. According to further aspects, the lymphocytes comprise isolated B cells.

In some aspects, methods are provided wherein the relative frequencies of target antibody cDNA sequences are compared before and after exposure to the antigen, wherein target antibody cDNA sequences having a significantly higher frequency after exposure to the antigen are identified as candidate antibody sequences.

In further aspects, a host subject is re-immunized with the antigen, a cDNA sequence library is created after the re-immunization, and the relative frequencies of the target antibody sequences are compared before and after the re-immunization, wherein antibody sequences present at a significantly higher frequency after the re-immunization are identified as mature candidate antibody sequences.

In some aspects, methods are provided wherein the relative frequencies of target antibody cDNA sequences are compared at two or more times after exposure to the antigen, wherein target antibody cDNA sequences having a significantly lower frequency in later times are identified as candidate antibody sequences.

Host Immunization and Antibody Production

Immunogens are delivered to a host for eliciting an immune response. The host can be any animal known in the art that is useful in biotechnological screening assays and is capable of producing recoverable antibodies when administered an immunogen, such as but not limited to, rabbits, mice, rats, hamsters, monkeys, baboons and humans. In yet another aspect, the host is transgenic and produces human antibodies, thereby greatly easing the development work for creating a human therapeutic.

In some aspects of the present disclosure, methods are provided wherein the target antibody sequences comprise immunoglobulin (Ig) heavy chain variable domain sequences. In further aspects the target antibody sequences comprise sequences of one or more complementarity determining regions (CDRs) of an immunoglobulin (Ig) heavy chain variable domain. In various aspects, a candidate antibody sequences with a light chain variable domain sequence and an Ig framework to produce a set of candidate monoclonal antibodies. In some aspects, the Ig framework is a human Ig framework.

In certain aspects, the host subject is an experimental animal. In some aspects, the host subject is a transgenic animal expressing human antibodies. In further aspects the host subject is a human patient that has been exposed to an antigen or a pathogen or is suffering from a disease which alters the adaptive immune response.

The term "antibody" refers to any immunoglobulin or intact molecule as well as to fragments thereof that bind to a specific epitope. Such antibodies include, but are not limited to polyclonal, monoclonal, chimeric, humanized, single chain, Fab, Fab', F(ab)' fragments and/or F(v) portions of the whole antibody. Antibodies can include monoclonal antibodies, polyclonal antibodies, single-chain antibodies, and fragments thereof which retain the antigen binding function of the parent antibody.

An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a VH domain; and (vi) an isolated complementarity determining region (CDR).

The term "single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments can be prepared by recombinant techniques or enzymatic or chemical cleavage of intact antibodies.

The term "antibody fragment" refers to an incomplete or isolated portion of the full sequence of the antibody which retains the antigen binding function of the parent antibody. Examples of antibody fragments include Fab, Fab', F(ab')2, and Fv fragments; diabodies; linear antibodies; single-chain antibody molecules; and multispecific antibodies formed from antibody fragments. Antibody fragments are encompassed by the present disclosure so long as they retain the desired affinity of the full-length antibody. In particular, it can be shorter by at least one amino acid.

Also, recombinant immunoglobulins can be produced. See, Cabilly, U.S. Pat. No. 4,816,567, incorporated herein by reference in its entirety and for all purposes; and Queen et al., Proc Natl Acad Sci USA, 86:10029-10033 (1989).

The term "monoclonal antibody" refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences.

The term "immune cell response" refers to the response of immune system cells to external or internal stimuli (e.g., antigen, cell surface receptors, cytokines, chemokines, and other cells) producing biochemical changes in the immune cells that result in immune cell migration, killing of target cells, phagocytosis, production of antibodies, other soluble effectors of the immune response, and the like.

"Immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, metastatic breast cancer cells, invading pathogens, cells or tissues infected with pathogens, or, in cases of autoimmunity or pathological inflammation, normal human cells or tissues.

The term "protective immunity" means that the subject mounts an active immune response to the immunogenic composition and/or that the subject has been provided with passive immunity, such that upon subsequent exposure or a challenge, the subject is able to resist and/or overcome infection and/or disease. Thus, a protective immune response will preferably decrease the incidence of morbidity and/or mortality from subsequent exposure to infection and/or disease.

"Adaptive immunity" or "adaptive immune response" are used interchangeably and in a broad sense herein and mean the immune response to antigen challenge, including the development of immunological memory. The adaptive immune response includes, without limitation, humoral and cellular immunity.

An "active immune response" is mounted by the host after exposure to immunogens by infection or by vaccination. In contrast, "passive immunity" is acquired through the transfer of preformed substances (e.g., antibodies, transfer factors, thymic grafts, interleukin-2, and the like) from an actively immunized host to a non-immune host.

"Lymphocyte" as used herein has the normal meaning in the art, and refers to any of the mononuclear, non-phagocytic leukocytes, found in the blood, lymph, and lymphoid tissues, e.g., B and T lymphocytes.

"T lymphocyte response" and "T lymphocyte activity" are used here interchangeably to refer to the component of immune response dependent on T lymphocytes (e.g., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen et al., Immunity, 2:373-380 (1995)); (3) antigen presenting cells can be incubated with whole protein antigen and the presentation of that antigen on MHC detected by either T lymphocyte activation assays or biophysical methods (Harding et al., Proc Natl Acad Sci, 86:4230-4234 (1989)); (4) mast cells can be incubated with reagents that cross-link their Fc-epsilon receptors and histamine release measured by enzyme immunoassay (Siraganian et al., TIPS, 4:432-437 (1983)).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., Blood, 72:1310-1315 (1988)); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in peripheral blood mononuclear cells (PBMCs)s can be measured by placing PBMCs in wells together with labeled particles (Peters et al., Blood, 72:1310-1315 (1988)); and (5) the differentiation of immune system cells can be measured by labeling PBMCs with antibodies to CD molecules such as CD4 and CD8 and measuring the fraction of the PBMCs expressing these markers.

For convenience, immune responses are often described in the present disclosure as being either "primary" or "secondary" immune responses. A primary immune response, which is also described as a "protective" immune response, refers to an immune response produced in an individual as a result of some initial exposure (e.g., the initial "immunization") to a particular antigen, e.g., cell surface receptor, or activated integrin receptor. Such an immunization can occur, for example, as the result of some natural exposure to the antigen (for example, from initial infection by some pathogen that exhibits or presents the antigen) or from antigen presented by cancer cells of some tumor in the individual. Alternatively, the immunization can occur as a result of vaccinating the individual with a vaccine containing the antigen.

A primary immune response can become weakened or attenuated over time and can even disappear or at least become so attenuated that it cannot be detected. Accordingly, the present disclosure also relates to a "secondary" immune response, which is also described here as a "memory immune response." The term secondary immune response refers to an immune response elicited in an individual after a primary immune response has already been produced. Thus, a secondary or immune response can be elicited, e.g., to enhance an existing immune response that has become weakened or attenuated, or to recreate a previous immune response that has either disappeared or can no longer be detected. An agent that can be administrated to elicit a secondary immune response is after referred to as a "booster" since the agent can be said to "boost" the primary immune response.

As an example, and not by way of limitation, a secondary immune response can be elicited by re-introducing to the individual an antigen that elicited the primary immune response (for example, by re-administrating a vaccine). However, a secondary immune response to an antigen can also be elicited by administrating other agents that cannot contain the actual antigen. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4+ cells. A first exposure to an antigen primes the immune system and additional exposure(s) results in a DTH.

According to certain aspects, the present disclosure provides that a host subject is immunized with multiple antigens. In further aspects, the monoclonal antibody is reactive to multiple antigens.

"Immunologically cross-reactive" or "immunologically reactive" refers to an antigen which is specifically reactive with an antibody which was generated using the same ("immunologically reactive") or different ("immunologically cross-reactive") antigen.

"Immunologically reactive conditions" refers to conditions which allow an antibody, generated to a particular epitope of an antigen, to bind to that epitope to a detectably greater degree than the antibody binds to substantially all other epitopes, generally at least two times above background binding, preferably at least five times above background Immunologically reactive conditions are dependent upon the format of the antibody binding reaction and typically are those utilized in immunoassay protocols. See, Harlow and Lane, Antibodies, A Laboratory Manual (1988) for a description of immunoassay formats and conditions.

"Effector cell" refers to an immune cell which is involved in the effector phase of an immune response, as opposed to the cognitive and activation phases of an immune response.

Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fe receptors and carry out specific immune functions. An effector cell can induce antibody-dependent cell-mediated cytotoxicity (ADCC), e.g., a neutrophil capable of inducing ADCC. An effector cell can also phagocytose a target antigen, target cell, metastatic cancer cell, or microorganism.

The term "antigen" refers to a substance that prompts the generation of antibodies and can cause an immune response. It can be used interchangeably in the present disclosure with the term "immunogen". In the strict sense, immunogens are those substances that elicit a response from the immune system, whereas antigens are defined as substances that bind to specific antibodies. An antigen or fragment thereof can be a molecule (i.e., an epitope) that makes contact with a particular antibody. When a protein or a fragment of a protein is used to immunize a host animal, numerous regions of the protein can induce the production of antibodies (i.e., elicit the immune response), which bind specifically to the antigen (given regions or three-dimensional structures on the protein).

The term "epitope" refers to a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Examples of the methods used for the production of the monoclonal antibodies of the present disclosure are given in EXAMPLES 1-5. These examples provide general methods used for the production of monoclonal antibodies.

In addition, techniques developed for the production of "chimeric antibodies" (Morrison et al., Proc Natl Acad Sci, 81:6851-6855 (1984)), incorporated herein by reference in their entirety) by splicing the genes from a mouse antibody molecule of appropriate antigen specificity together with genes from a human antibody molecule of appropriate biological activity can be used. For example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region.

The term "human sequence antibody" includes antibodies having variable and constant regions (if present) derived from human germline immunoglobulin sequences. The human sequence antibodies of the present disclosure can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT App. Pub. Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

The term "humanized antibody," refers to at least one antibody molecule in which the amino acid sequence in the non-antigen binding regions has been altered so that the antibody more closely resembles a human antibody, and still retains its original binding ability.

In addition, techniques have been developed for the production of humanized antibodies (see, e.g., U.S. Pat. Nos. 5,585,089 and 5,225,539, which are incorporated herein by reference in their entirety). An immunoglobulin light or heavy chain variable region consists of a "framework" region interrupted by three hypervariable regions, referred to as complementarity determining regions (CDRs). Briefly, humanized antibodies are antibody molecules from non-human species having one or more CDRs from the non-human species and a framework region from a human immunoglobulin molecule.

In certain aspects of the present disclosure, humanized antibodies are produced. In order to humanize an antibody derived from a different species, the antibody is sequenced and those sequences are placed into a human antibody backbone. Because certain sequences are predictably easier than others to place into the human backbone, the list of candidate sequences can be selected on the basis of ease of humanization.

In further aspects, the candidate sequences can be placed directly into a human backbone, thereby bypassing the steps of cloning and expression of the native non-humanized protein. Humanized animal technology is a method to create monoclonal antibodies that do not require humanization. The humanized antibodies are produced by creating a transgenic mouse wherein the native Ig loci are replaced with the corresponding human Ig loci. The resulting antibody is thus human and does not require humanization. However, this process still requires that a monoclonal antibody with a desired property is recovered from the humanized animal using either hybridoma or B cell isolation techniques.

Alternatively, techniques described for the production of single chain antibodies can be adapted to produce single chain antibodies against an immunogenic conjugate of the present disclosure. Single chain antibodies are formed by linking the heavy and light chain fragments of the Fv region via an amino acid bridge, resulting in a single chain polypeptide. Fab and F(ab')2 portions of antibody molecules can be prepared by the proteolytic reaction of papain and pepsin, respectively, on substantially intact antibody molecules by methods that are well-known. See e.g., U.S. Pat. No. 4,342,566. Fab' antibody molecule portions are also well-known and are produced from F(ab')2 portions followed by reduction of the disulfide bonds linking the two heavy chain portions as with mercaptoethanol, and followed by alkylation of the resulting protein mercaptan with a reagent such as iodoacetamide.

The antibodies of the present disclosure can bind to their corresponding antigen. For example, the antibodies can bind to a corresponding antigen displayed on the surface of a cell, in which case, the cell is targeted for immune mediated lysis. The monoclonal antibodies of the present disclosure have high affinity for their corresponding antigens.

According to some aspects, the present disclosure provides for a method for deriving monoclonal antibodies from an immunized organism. The organism can be an experimental organism treated with the antigen and appropriate adjuvant, or exposed to a pathogen or other biological agent. The organism can also be a human patient suffering from exposure to a pathogen or a disease. Since the method requires only small amounts of blood or tissue, the same organism can be sampled multiple times.

The antibody can be labeled with at least one radionuclide in order to improve targeting of infectious and/or diseased elements in vivo in at least a diagnostic and/or therapeutic capacity. The antibody can be labeled with at least one toxin and/or chemotherapeutic reagent. In particular, the labeled antibody can be used as an immunotoxin that better targets these toxic agents to infectious and/or diseased elements.

It will be appreciated that once the CDRs of an antibody are identified, conventional genetic engineering techniques can be used to devise expressible polynucleotides encoding any of the forms or fragments of antibodies described herein.

Adjuvants

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Further suitable adjuvants can include, for example, any of the following: aluminum salts (alum), Complete Freund's adjuvant (CFA), Incomplete Freund's adjuvant (IFA), muramyl dipeptide (MDP). See, e.g., Ellouz et al., Biochem Biophys Res Commun, 59:1317 (1974). Synthetic analogs of MDP (see, Chedid et al., Prog Allergy, 25:63 (1978)), analogs of MDP including threonyl derivatives of MDP (Byars et al., Vaccine, 5:223 (1987)), n-butyl derivatives of MDP (Chedid et al., Infect Immun, 35:417), and a lipophilic derivative of a muramyl tripeptide (Gisler et al., in Immunomodulations of Microbial Products and Related Synthetic Compounds, 167 (1981)). MDP compounds, such as thurMDP and nor-MDP, CGP (MTP-PE). Additional adjuvants include MF59 (See, e.g., Ott et al., "MF59—Design and Evaluation of a Safe and Potent Adjuvant for Human Vaccines" in Vaccine Design: The Subunit and Adjuvant Approach, 277-296 (1995)). QS21 is another adjuvant that has been shown to have significant immunological activity (Kensil et al., (1991); Wu et al., (1992); White et al., (1991) and White et al., Adv Exp Med Biol, 303:207-210 (1991)). Additional adjuvants include saponin (Kensil et al., J Immunol, 148:1519-1525 (1992); and Kensil et al., J Immunol, 146:431-437 (1991)). Yet further adjuvants according to the present methods include IL-1, IL-2, IL-4, IL-7, IL-12, γ-interferon, GMCSP, BCG, Resiquimod (R-848), aluminum hydroxide, lipid A, and monophosphoryl lipid A (MPL). RIBI, MPL, trehalose dimycolate (TDM) and cell wall skeleton (CWS) in a 2% squalene/Tween 80 emulsion is also contemplated.

Absence of Pre-Immunization

In another aspect, the present methods can be performed in the absence of pre-immunization data. For instance, this method is useful when pre-immune serum samples are not available such as can be the case if a human is exposed to a pathogen. Under these conditions, sequence frequency data post-infection is be used to derive a list of candidate antibody sequences as the number of circulating plasmacytes will fall off significantly. This technique is particularly useful for rapid antibody generation during epidemics.

Generation of Antibodies Against Multiple Related Antigens

In certain aspects of the present disclosure, different but related species of antigens are given to the host after multiple boosts. The antibodies are subsequently screened for cross-reactivity between multiple antigens, such as can be required for certain applications. For example, it can be desirable to create antibodies against a family of pathogen-derived proteins, or a set of synthetically designed proteins. In EXAMPLE 5 below, it is shown that multiple IgG heavy and variable domain sequences were present in both arm 3 and arm 5 of the experiment in high significance clusters. The presence of identical significant sequences across samples shows that there is a level of overlap between different animals in generating antibodies against a common antigen. Therefore, antibodies against shared epitopes can be found across multiple related antigens by immunizing related antigens into separate cohorts and comparing induced sequences between the cohorts. Accordingly, a single animal can be boosted with different, but related, antigens in order to determine whether there are sets of related sequences that are induced after each boost. Thus, one aspect of the present disclosure provides for antibodies having reactivity to greater than one antigen, especially where the antigens are related.

Negative Selection Antigens

In certain aspects of the present disclosure, a final boost of a background antigen, for which it is undesirable to have antibodies against, can be performed. In this case, MPSS data from post-immunization of the background antigen is used to screen out undesired antibody candidates. For example, a synthetic epitope or protein backbone might be used to assist in creation of the antigen, such that the same epitope or backbone could be placed in the background antigen. In this case, the candidate antibody sequences matching the background data set are removed from the list of antibody sequences.

According to certain aspects, the present disclosure provides methods for administering a background antigen and selecting against antibodies that are reactive to the background antigen. In further aspects, the background antigen is administered after a first antigen.

Isolation of Lymphocytes

Once the host has been immunized, lymphocytes can be isolated from circulating blood or other tissues as appropriate. Various methods for isolating lymphocytes are well known in the art, for example, lymphocytes can be isolated from human peripheral blood by standard density gradient centrifugation, apheresis, negative selection (e.g., by removing red blood cells using red blood cell-specific antibodies or by osmotic lysis of red blood cells followed by washing in PBS), or any other suitable means known in the art.

In some aspects, the B cells are isolated away from other blood lymphocytes by positive or negative selection techniques. Examples of reagents for isolating B-Cells include conjugated antibodies for positive selection such as anti-CD19 antibodies and pluralities of conjugated antibodies for negative selection such as anti-CD2, anti-CD3, anti-CD14, anti-CD16, anti-CD56, anti-Glycophorin A antibody cocktails, where the antibodies are conjugated to an appropriate support.

In another aspect, antigen specific B cells can be isolated, using a biotinylated form of the monomer linked to an immunomagnetic bead. In a further aspect, cell sorting is utilized to isolate desired B cells, such as B memory cells. One method of sorting which can be utilized in accordance with the present disclosure is a sorting method using magnetic beads, such as those produced by Dynal or Miltenyi, can be utilized. Another method of B cell selection that can be used is fluorescence-activated cell sorting (FACS). Since B memory cells have immunoglobulin on their surface, this specificity can be utilized to identify and capture these cells. Optionally, beads can be coated with an antigen of interest and attached to a column. B cells with immunoglobulin on their surface can be identified by FACS as well as by binding to the antigen. In certain aspects, B cells are selected by first biotynylating immunogens that bind to specific B cell receptors found on the surface of B cells specific to the monomer. Anti-biotin coated magnetic-activated cell sorting (MACs) beads can then be used to isolate bound B cells on magnetic columns.

Isolating mRNA

In the present disclosure, mRNAs derived from a small number of lymphocytes or B cells are used. mRNAs are extracted from isolated lymphocytes or isolated B cells. cDNAs are synthesized by using the extracted mRNAs as a template to obtain a cDNA library. Commercially available kits are conveniently used for extracting mRNAs and for constructing the cDNA library. Total cellular RNA can be isolated from a biological sample such as the isolated lymphocytes, or alternatively the isolated B cells, using any suitable technique such as the single-step guanidinium-thiocyanate-phenol-chloroform method described by Chomczynski and Sacchi (Anal Biochem, 162:156-159 (1987)). A portion of the total RNA comprises nucleic acid molecules encoding the heavy or entire light chain of antibodies produced in response to an immunogen.

In various aspects, the nucleic acid molecules are isolated from lymphocytes or B cells derived from an immunized subject. Methods of isolating mRNA encoding an antibody are well-known in the art. See, e.g., Sambrook et al. The mRNA can be used to produce cDNA for use in the polymerase chain reaction (PCR) or cDNA cloning of antibody genes. In another aspect, the nucleic acid is isolated from a non-human, non-transgenic animal. The nucleic acid molecules isolated from a non-human, non-transgenic animal can be used, e.g., for humanized antibodies.

Production and Amplification of cDNA

In certain aspects, mRNA in a biological sample is used to produce cDNA from a sample by reverse transcription using at least one primer; amplifying the cDNA so produced using polynucleotides as sense and antisense primers to amplify cDNAs therein; and detecting the presence of the amplified cDNA. In further aspects, the sequence of the amplified cDNA can be determined by any suitable method.

A number of methods for amplifying and/or detecting the presence of polynucleotides are well known in the art and can be employed in the practice of the present methods. For instance, reverse transcription-polymerase chain reaction (RT-PCR) can be used to amplify sequences encoding the conserved regions from RNA obtained from a variety of cell or tissue sources or cell lines. In practicing the invention, nucleic acids encoding the polypeptides of the invention, or modified nucleic acids, can be reproduced by, e.g., amplification. Amplification methods include, e.g., polymerase chain reaction, PCR (PCR PROTOCOLS, A GUIDE TO METHODS AND APPLICATIONS, ed. Innis, Academic Press, N.Y. (1990) and PCR STRATEGIES, ed. Innis, Academic Press, Inc., N.Y., ligase chain reaction (LCR) (1995) (see, e.g., Wu, Genomics, 4:560 (1989); Landegren, Science, 241:1077 (1988); Barringer, 89:117 (1990)); transcription amplification (see, e.g., Kwoh, Proc Natl Acad Sci USA, 86:1173 (1989)); and, self-sustained sequence replication (see, e.g., Guatelli, Proc Natl Acad Sci USA, 87:1874 (1990)); Q Beta replicase amplification (see, e.g., Smith, J Clin Microbiol, 35:1477-1491 (1997)), automated Q-beta replicase amplification assay (see, e.g., Burg, Mol Cell Probes, 10:257-271 (1996)) and other RNA polymerase mediated techniques (e.g., NASBA, Cangene, Mississauga, Ontario); see also Berger, Methods Enzymol, 152:307-316 (1987); Sambrook; Ausubel; U.S. Pat. Nos. 4,683,195 and 4,683,202; Sooknanan, Biotechnology, 13:563-564 (1995).

Methods for designing and using primers for RT-PCR are well known in the art and can be readily performed by one of skill in the art. Any number of appropriate sense and antisense probe combinations can be designed from a nucleotide sequence and used for this purpose.

In certain aspects, the B cells are isolated from other blood lymphocytes by positive or negative selection techniques before generating the mRNA sample. Additionally, a linear amplification step can be applied to create a more representative sequencing sample, for example T7 RNA polymerase sites can be placed in the cDNA primer in order to create more mRNA corresponding to the the Ig heavy chain region by using T7 RNA polymerase, which can then be used for cDNA creation and PCR.

Sequencing

The methods of the present disclosure are not limited to any particular sequencing method but can be used in conjunction with essentially any sequencing methodology which relies on successive incorporation of nucleotides into a polynucleotide chain. Suitable techniques include, for example, Pyrosequencing™, FISSEQ (fluorescent in situ sequencing), MPSS (massively parallel signature sequencing), and sequencing by litigation-based methods, some of which are described in more detail below.

According to certain aspects, the present disclosure provides methods for sequencing the high affinity monoclonal antibodies. In further aspects, the relative frequencies of target antibody sequences are analyzed using a bioinformatics software algorithm. In yet further aspects the amplified target cDNA sequences are sequenced by massively parallel signature sequencing (MPSS).

In one aspect of the present disclosure, massively parallel methods are used for the identification and quantification of nucleotide sequences. Additionally, the method preferably exhibits a wide, dynamic range and high sensitivity enabling the quantitation of highly abundant as well as rare species. Also preferred is a method that provides an absolute measure of abundance, rather than relative quantitation as a ratio to a housekeeping or normalizing gene. Absolute abundance facilitates comparison of the nucleotide abundances between samples and between experiments, and allows the data from different runs to be "banked" in a database and directly compared. Finally, in order to permit the discovery of new nucleotide sequences, the method preferably provides direct sequence readout, and is independent of prior sequence knowledge. Several methods for nucleotide sequence analysis have been described that demonstrate one or more of these performance features.

The sequencing methods of Mermod et al. (PCT App. Pub. No. WO 00/18957) and Adessi et al., Nucleic Acids Res, 28(20):e87 (2000)) can also be used according to the present disclosure. They have described a method of solid-phase PCR in which highly multiplexed DNA colonies derived from individual DNA fragments are created on the surface of a solid support. In this method, primer pairs and templates containing universal priming sites are immobilized on the surface of a functionalized glass slide at a density appropriate for the generation of discrete colonies. Amplification of the templates occurs by primer extension in a process called "bridge amplification" to create on the order of two thousand copies of each template per colony. This method is purported to yield colonies at a density of millions of features per $mm^2$, which is suitable for genome-wide analysis. Sequence analysis of the colonies can be carried out by traditional methods, such as sequencing by addition or MPSS.

Leamon et al., have described a method of highly multiplexed genomic DNA amplification in a low volume plate-based platform that is also applicable to the present disclosure. PCR products derived from genomic fragments are attached to solid-phase beads, and sequencing of the fragments is carried out by synthesis using the Pyrosequencing™ technology. Such technology is applicable to the present disclosure.

Other appropriate sequencing methods include multiplex polony sequencing (as described in Shendure et al., Accurate Multiplex Polony Sequencing of an Evolved Bacterial Genome, Sciencexpress, Aug. 4, 2005, pg 1 available at www.sciencexpress.org/4 Aug. 2005/Page1/10.1126/science.1117389, incorporated herein by reference), which employs immobilized microbeads, and sequencing in microfabricated picoliter reactors (as described in Margulies et al., Genome Sequencing in Microfabricated High-Density Picolitre Reactors, Nature, August 2005, available at www.nature.com/nature (published online 31 Jul. 2005, doi: 10.1038/nature03959, incorporated herein by reference). In certain aspects of the present disclosure, any one of these methods can be used to sequence the cDNA vectors to obtain sequence data on the isolated RNA sequences.

Massively Parallel Signature Sequencing (MPSS)

In certain aspects of the present disclosure, MPSS is used for sequencing cDNA. When using MPSS, a single species of DNA is attached to a solid support bead. Millions of these beads are created in a single reaction using emulsive PCR. The beads are placed in a chamber and subject to multiple rounds of pyrogenic sequencing, which is a chemistry that allows the beads to fluoresce depending on what base is next in the sequence. During each round the beads are photographed by a sensitive CCD camera and in this manner the sequence of the DNA on each of the bead is deduced. The result is that millions of sequences can be produced in a single run. Until recently, the length of these sequence reads were only 20 to 30 bases. Newer chemistry now allows for reads in the range of 400 bases, such as is the case with the Roche 454 titanium technology. These longer read methods allow of the generation of millions of 400 base long sequences in parallel which is a sufficient length to cover the entire variable domain region of both Ig heavy and light chain sequences. Furthermore, this type of sequencing does not require large amounts of starting material. For example, a long read MPSS run requires only 250 nanograms of DNA.

After hybridization, a minimum of one million beads are immobilized in a flow cell for sequencing biochemistry and imaging. The signature sequence on each bead is determined in parallel. The novel sequencing process involves repeatedly exposing four nucleotides by enzymatic digestion, ligating a family of encoded adapters, and decoding the sequence by sequential hybridization with fluorescent decoder probes.

The MPSS sequencing process is fully automated. Buffers and reagents are delivered to the beads in the flow cell via a proprietary instrumentation platform, and sequence-dependent fluorescent responses from the micro-beads are recorded by a CCD camera after each cycle.

MPSS data have many uses. The expression levels of nearly all polyadenylated transcripts can be quantitatively determined; the abundance of signatures is representative of the expression level of the gene in the analyzed tissue. Quantitative methods for the analysis of tag frequencies and detection of differences among libraries have been published and incorporated into public databases for SAGE™ data and are applicable to MPSS data. The availability of complete genome sequences permits the direct comparison of signatures to genomic sequences and further extends the utility of MPSS data. Because the targets for MPSS analysis are not pre-selected (like on a microarray), MPSS data are able to characterize the full complexity of transcriptomes, and can be used for "gene discovery". This is analogous to sequencing millions of ESTs at once, but the short length of the MPSS signatures makes the approach most useful in organisms for which genomic sequence data are available so that the source of the MPSS signature can be readily identified by computational means.

Additional information regarding MPSS technology can be obtained by reviewing the many publications on this subject, including U.S. Pat. Nos. 6,013,445, 5,846,719, and 5,714,330, all of which are incorporated herein by reference.

In one aspect of the present disclosure the heavy chain variable domain region for a specific isotype of antibody is used to create an MPSS library and subject to MPSS sequencing. The sample can be taken from lymphocytes or isolated B cells found in circulating blood or other appropriate tissue. In order to apply the MPSS sequencing technology, specific DNA sequence tags must be placed at either end of the region of DNAs to be sequenced. This can be accomplished by creating a cDNA from mRNA taken from B cells using reverse-transcriptase, and then applying polymerase chain reaction (PCR) using primers with both the appropriate isotype specific sequences and the MPSS tags to generate the DNA library.

The MPSS method involves significant amounts of digital analysis. As a result, perfect sequence subtraction and analysis can be preformed, as opposed to physical methods which are always subject to imperfections and contamination. Also, unlike physical methods, the digital analysis technique can be altered and applied multiple times without the need for additional physical samples.

More precise information about the candidate antibody sequences can be produced by more frequent sampling using MPSS. Samples might be taken as the organism's response falls back to background levels and to establish the background before the next boost. Another advantage of multiple data points is that affinity maturation data of the antibody can be generated. For example one or more highly related antibodies to an antibody detected in a previous sample might appear over time that represents a B cell line which has undergone affinity maturation. Affinity matured antibodies have higher affinity for the target sequence than the parental sequence, so identification of these sequences can be desirable.

In certain aspects, the list of candidate sequences might be changed by applying filters based on the DNA sequence or predicted protein sequence. For example, if additional cysteine residues are present in the sequence, which are judged as likely to create potential difficulties in manufacturing of the protein, those sequences could be removed from the candidate antibody sequence list. Other properties of the predicted protein sequences could also be used, such as the presence or absence of charged residues, or conformance to canonical antibody sequence patterns.

Nucleic Acids

According to another aspect, the present disclosure provides an isolated nucleic acid molecule encoding: at least one heavy chain of an antibody or a fragment thereof as identified by the present methods and/or at least one light chain of an antibody as identified by the present methods. In further aspects, the present disclosure provides for variants, mutants or fragments of the isolated nucleic acids as well.

According to further aspects, the present disclosure provides an expression vector comprising the nucleic acid which encodes an antibody identified according to the present methods and a host cell comprising the expression vector. In particular, the vectors can comprise, but are not limited to, lentiviral vectors, retroviral vectors, adenoviral vectors, adeno-associated virus vectors and Herpes Simplex Virus vectors. More in particular, retroviral vectors can be used for delivery of the constructs either in vitro, ex vivo or in vivo.

Recombinant Nucleic Acid Techniques

The nucleic acids used to practice this invention, whether RNA, siRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams, J Am Chem Soc, 105:661 (1983); Belousov, Nucleic Acids Res, 25:3440-3444 (1997); Frenkel, Free Radic Biol Med, 19:373-380 (1995); Blommers, Biochemistry, 33:7886-7896 (1994); Narang, Meth Enzymol, 68:90 (1979); Brown, Meth Enzymol, 68:109 (1979); Beaucage, Tetra Lett, 22:1859 (1981); U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook and Russell, ed., MOLECULAR CLONING: A LABORATORY MANUAL (3rd ED.), Vols. 1-3, Cold Spring Harbor Laboratory (2001); CURRENT PROTOCOLS IN MOLECULAR BIOLOGY; Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, adioimmunoassay (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the present disclosure can be done by cloning from genomic samples, and, if desired, screening and re-cloning inserts isolated or amplified from, e.g., genomic clones or cDNA clones. Sources of nucleic acid used in the methods of the present disclosure include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld, Nat Genet, 15:333-335 (1997); yeast artificial chromosomes (YAC); bacterial artificial chromosomes (BAC); P1 artificial chromosomes, see, e.g., Woon, Genomics, 50:306-316 (1998); P1-derived vectors (PACs), see, e.g., Kern, Biotechniques, 23:120-124 (1997); cosmids, recombinant viruses, phages or plasmids.

The present disclosure provides fusion proteins and nucleic acids encoding an antibody as identified by the present methods. An antibody can be fused to a heterologous peptide or polypeptide, such as N-terminal identification peptides which impart desired characteristics, such as increased stability or simplified purification. Peptides and polypeptides of the present disclosure can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Sigma Aldrich, St. Louis, Mo.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams, Biochemistry, 34:1787-1797 (1995); Dobeli, Protein Expr Purif, 12:404-414 (1998). The histidine residues facilitate detection and purification while the enterokinase cleavage site provides a means for purifying the epitope from the remainder of the fusion protein. In one aspect, a nucleic acid encoding a polypeptide is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll, DNA Cell Biol, 12:441-53 (1993).

In some aspects, a nucleic acid encoding a heavy chain of an antibody of the present disclosure can comprise a nucleotide sequence encoding a $V_H$ domain of the present disclosure joined in-frame to a nucleotide sequence encoding a heavy chain constant domain from any source. Similarly, a nucleic acid molecule encoding a light chain of an antibody as identified by the present methods can comprise a nucleotide sequence encoding a $V_L$ domain of the present disclosure joined in-frame to a nucleotide sequence encoding a light chain constant domain from any source.

In a further aspect of the present disclosure, nucleic acid molecules encoding the variable domain of the heavy ($V_H$) and light ($V_L$) chains are "converted" to full-length antibody genes. In one aspect, nucleic acid molecules encoding the $V_H$ or $V_L$ domains are converted to full-length antibody genes by insertion into an expression vector already encoding heavy chain constant ($C_H$) or light chain ($C_H$) constant domains, respectively, such that the $V_H$ segment is operatively linked to the $C_H$ segment(s) within the vector, and the $V_L$ segment is operatively linked to the $C_L$ segment within the vector. In another aspect, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the art. See, e.g., Kabat et al., Sequences of Proteins of Immunological Interest, 5th Ed., NIH Publ. No. 91-3242 (1991). Nucleic acid molecules encoding the full-length heavy and/or light chains can then be expressed from a cell into which they have been introduced and the particular monoclonal antibody isolated.

The nucleic acid molecules can be used to recombinantly express large quantities of monoclonal antibodies. The nucleic acid molecules also can be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules can be used for antibody humanization, also as described herein.

In another aspect, a nucleic acid molecule of the present disclosure is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of particular antibodies. In some aspects, the nucleic acid molecules are oligonucleotides. In some aspects, the oligonucleotides are from highly variable regions of the heavy and light chains of the antibody of interest.

Transcriptional Control Elements

The nucleic acids, as aspects of the present disclosure, can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

Expression Vectors and Cloning Vehicles

Aspects of the present disclosure provide expression vectors and cloning vehicles comprising nucleic acids of the invention, e.g., sequences encoding the proteins of the invention. Expression vectors and cloning vehicles can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, Aspergillus and yeast). Vectors can include chromosomal, non-chromosomal and synthetic DNA sequences. Large numbers of suitable vectors are known to those of skill in the art, and are commercially available.

The nucleic acids of the present disclosure can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair.

The present disclosure provides libraries of expression vectors encoding polypeptides and peptides of the invention. These nucleic acids can be introduced into a genome or into the cytoplasm or a nucleus of a cell and expressed by a variety of conventional techniques, well described in the scientific and patent literature. See, e.g., Roberts, Nature, 328:731 (1987); Schneider, Protein Expr Purif, 6435:10 (1995); Sambrook, Tijssen or Ausubel. The vectors can be isolated from natural sources, obtained from such sources as ATCC or GenBank libraries, or prepared by synthetic or recombinant methods. For example, the nucleic acids of the present disclosure can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the present disclosure are administered in vivo for in situ expression of the peptides or polypeptides of the present disclosure. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors can also be employed which exploit advantageous merits of each of the parent vector properties (See e.g., Feng, Nature Biotechnology, 15:866-870 (1997)). Such viral genomes can be modified by recombinant DNA techniques to include the nucleic acids of the present disclosure; and can be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher, J Virol, 66:2731-2739 (1992); Johann, J Virol, 66:1635-1640 (1992). Adeno-associated virus (AAV)-based vectors can be used to adioimmun cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada, Gene Ther, 3:957-964 (1996).

The term "expression cassette" refers to a nucleotide sequence which is capable of affecting expression of a structural gene (i.e., a protein coding sequence, such as a polypeptide of the present disclosure) in a host compatible with such sequences. Expression cassettes include at least a promoter operably linked with the polypeptide coding sequence; and, optionally, with other sequences, e.g., transcription termination signals. Additional factors necessary or helpful in effecting expression can also be used, e.g., enhancers.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination. Thus, expression cassettes also include plasmids, expression vectors, recombinant viruses, any form of recombinant "naked DNA" vector, and the like.

The term "vector" is intended to refer to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

Host Cells and Transformed Cells

The present disclosure also provides a transformed cell comprising a nucleic acid sequence of the invention, e.g., a sequence encoding a polypeptide of the invention, or a vector of the invention. The host cell can be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the present disclosure. Following transformation of a suitable host strain and growth of the host strain to an appropriate cell density, the selected promoter can be induced by appropriate means (e.g., temperature shift or chemical induction) and the cells can be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector can be glycosylated or can be non-glycosylated. Polypeptides of the present disclosure can or can not also include an initial methionine amino acid residue.

Cell-free translation systems can also be employed to produce a polypeptide of the present disclosure. Cell-free translation systems can use mRNAs transcribed from a DNA construct comprising a promoter operably linked to a nucleic acid encoding the polypeptide or fragment thereof. In some aspects, the DNA construct can be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Functional Moieties

In one aspect, the monoclonal antibodies generated according to the present methods can be modified to have at least one functional moiety, such as but not limited to, a detectable moiety or a therapeutic moiety, bound thereto. For example, but not by way of limitation, the detectable moiety can be selected from the group consisting of a fluorophore, an enzyme, a radioisotope and combinations thereof, while the therapeutic moiety can be selected from the group consisting of a cytotoxic moiety, a toxic moiety, a cytokine moiety, a bi-specific antibody moiety, and combinations thereof.

Many methods are known in the art to conjugate or fuse (couple) molecules of different types, including peptides. These methods can be used according to the present disclosure to couple an antibody another moiety, such as a therapeutic moiety or an identifiable moiety, to thereby provide an immunotoxin or immunolabel.

Two isolated peptides can be conjugated or fused using any conjugation method known to one skilled in the art. A peptide can be conjugated to an antibody of interest, using a 3-(2-pyridyldithio)propionic acid N-hydroxysuccinimide ester (also called N-succinimidyl 3-(2-pyridyldithio) propionate) ("SDPD"), a glutaraldehyde conjugation procedure, or a carbodiimide conjugation procedure.

Any SPDP conjugation method known to those skilled in the art can be used. For example, in one illustrative aspect, the method of conjugation by Cumber et al., Methods of Enzymology, 112:207-224 (1985), can be used.

Conjugation of a peptide (e.g., an identifiable or therapeutic moiety) with an antibody can be accomplished by methods known to those skilled in the art using glutaraldehyde. For example, in one illustrative aspect, the method of conjugation by G. T. Hermanson, "Antibody Modification and Conjugation, in Bioconjugate Techniques", Academic Press, San Diego (1996) can be used.

Conjugation of a peptide with an antibody can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond).

Likewise, carbodiimide coupling can be used to form analogous covalent bonds between a carbon group of an antibody and a hydroxyl, amino or sulfhydryl group of the peptide. See, generally, March, Advanced Organic Chemistry: Reaction's, Mechanism, and Structure, 3d ed.:349-50 & 372-74 (1985). By means of illustration, and not limitation, the peptide is conjugated to an antibody via a covalent bond using a carbodiimide, such as dicyclohexylcarbodiimide. See generally, the methods of conjugation by Neises et al., Angew Chem, Int Ed Engl, 17:522 (1978); Hassner et al., Tetrahedron Lett, 4475 (1978); Boden et al., J Org Chem, 50:2394 (1986) and Mathias, Synthesis, 561 (1979).

Antibody Assays

According to certain aspects, the present disclosure provides methods for assaying the candidate monoclonal antibodies for affinity to an antigen. In further aspects, the present disclosure provides for subjecting the candidate monoclonal antibodies to positive selection to identify high affinity monoclonal antibodies. In yet further aspects, subjecting the candidate monoclonal antibodies to positive selection comprises contacting the candidate monoclonal antibodies to the antigen bound to a substrate and isolating bound antibodies from unbound antibodies.

The terms "specific binding" or "specifically binding" refer to the interaction between the antigen and their corresponding antibodies. The interaction is dependent upon the presence of a particular structure of the protein recognized by the binding molecule (i.e., the antigen or epitope). In order for binding to be specific, it should involve antibody binding of the epitope(s) of interest and not background antigens.

Once the antibodies are produced, they are assayed to confirm that they are specific for the antigen of interest and to determine whether they exhibit any cross reactivity with other antigens. One method of conducting such assays is a sera screen assay as described in U.S. App. Pub. No. 2004/0126829, the contents of which are hereby expressly incorporated herein by reference. However, other methods of assaying for quality control are within the skill of a person of ordinary skill in the art and therefore are also within the scope of the present disclosure.

Antibodies, or antigen-binding fragments, variants or derivatives thereof of the present disclosure can also be described or specified in terms of their binding affinity to an antigen. The affinity of an antibody for an antigen can be determined experimentally using any suitable method. (See, e.g., Berzofsky et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer.

The affinity binding constant ($K_{aff}$) can be determined using the following formula:

$$K_{aff} = \frac{(n-1)}{2(n[mAb']_t - [mAb]_t)}$$

in which:

$$n = \frac{[mAg]_t}{[mAg']_t}$$

[mAb] is the concentration of free antigen sites, and [mAg] is the concentration of free monoclonal binding sites as determined at two different antigen concentrations (i.e., $[mAg]_t$ and $[mAg']_t$) (Beatty et al., J Imm Meth, 100:173-179 (1987)).

The term "high affinity" for an antibody refers to an equilibrium association constant ($K_{aff}$) of at least about $1\times10^7$ liters/mole, or at least about $1\times10^8$ liters/mole, or at least about $1\times10^9$ liters/mole, or at least about $1\times10^{10}$ liters/mole, or at least about $1\times10^{11}$ liters/mole, or at least about $1\times10^{12}$ liters/mole, or at least about $1\times10^{13}$ liters/mole, or at least about $1\times10^{14}$ liters/mole or greater. "High affinity" binding can vary for antibody isotypes.

EXEMPLARY ASPECTS

Example 1

Antigen Specific Ig Heavy Chain Variable Region Candidate Library Generation

FIG. 1 describes a representative process of identification of antigen-specific heavy chain sequences using MPSS and bioinformatic subtraction. In this example, an isotype of Ig heavy chain's variable region is used to create a sample for MPSS sequencing as described above. Samples are generated from the organism both before and after exposure to the antigen. Once these data are generated, then the sequences are compared using a bioinformatic algorithm which identifies those sequences which are significantly amplified or appear only after exposure to the antigen. Those sequences matching these criteria are used to create a set of candidate antigen specific heavy chain sequences. Due to the large number of sequences generated by MPSS, it is possible to estimate the relative abundance of individual sequences by counting the number of times that sequences appears in the database. This quantitative estimate can be used to find sequences that are present in significantly greater numbers in the post-immunized sample as compared to the pre-immunized sample.

Example 2

Figure 2:
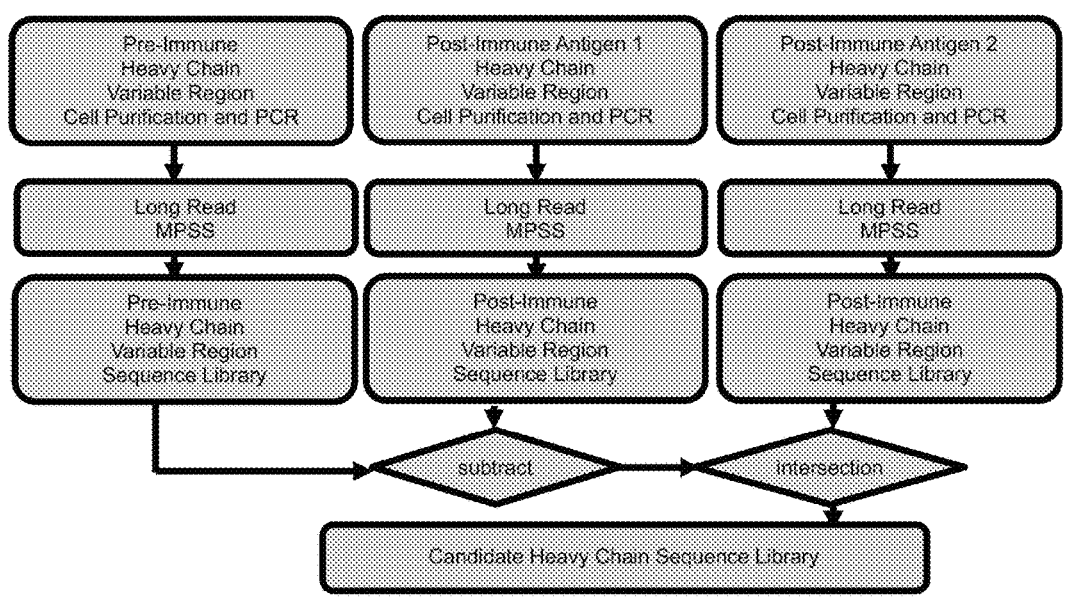
FIG. 2: Heavy Chain Sequence Library Generation using Multiple Boosts/Antigens. This figure is an extension of FIG. 1 whereby the variable region is sampled at multiple times after repeated boost with the same or related antigens. These data are digitally analyzed in order to identify candidate antibody variable domains that are induced after each boost which will react with the antigen(s).

Antigen Specific Ig Heavy Chain Variable Region Candidate Library Generation from Multiple Boosts or Antigens FIG. 2 describes an extension of the method described in FIG. 1 which can be used to identify antibodies that react to multiple related antigens or reaction to a single antigen over multiple boosts. In this example, Ig heavy chain specific MPSS sequencing is applied to the organism after each immunization with the same or different antigens and the bioinformatic subtraction is performed using the pre-immune sequences, while the intersection or union of the remaining sequences is performed between the first post-immune sample and the second post-immune sample. Stated otherwise, sequences common to the post-immune samples but not present, or present in significantly lower levels in the pre-immune sample are selected. One variant of this method is to look for related but not identical heavy chain regions that might represent affinity maturation of the antibody induced by multiple exposures to the same or related antigens.

Example 3

Formula for Variable Region Homology Tree Probability Calculation

Given a set of samples taken from different experimental arms at different time points and/or tissues, those samples can be divided into a foreground set A, a background set B, or neither, depending on the circumstances of the experiment and the calculation to be performed. The chances of a random occurrence of m of sequences or more in set A, compared to the total number of sequences n in both foreground A and background B sets defines the e-score, E(n,m,Pa), and is calculated using the following formula:

$$Pa = \frac{\text{(number of samples in set } A\text{)}}{\text{(number samples in set } A\text{)(number of samples in set } B\text{)}}$$

wherein Pa is defined as the probability of a sequence being in set A.

The binomial coefficient, i.e., the number of ways in which k items can be chosen from a set of n choices, can be determined using the following formula:

$$C(k, n) = \frac{n!}{k!(n-k)!}$$

wherein the symbol "!" indicates the integer factorial function.

The probability of k occurrences in set A is given by the following formula:

$$C(k,n)(Pa^k)((1-Pa)^{(n-k)})$$

The probability of m or more occurrences of sequences in set A is determined from the sum from m to n in the following formula:

$$E(n, m, Pa) = \sum_{K=m}^{n} C(k, n)(Pa^k)((1 - Pa)^{(n-k)})$$

The value E(n,m,Pa) is a calculation of the e-score, which is defined to be the chance at random of the event occurring n or more times in Pa versus anything other than Pa; i.e., the likelihood of m or more occurrences in set A out of n total events.

When this formula is applied to NGS sequence data potential errors from both sequencing and from sample preparation must be taken into account. While it can be applied at the individual sequence level the numerical count for that sequence may not be great enough for statistical significance. The e-score formula can also be applied to clusters of related sets of sequences and thus have higher significance values and be more tolerant of possible errors in the data. The logic is as follows: since not only is this single sequence present mostly in the set A and not set B, and all the most closely related sequences are also over-represented in set A but not set B, then the single sequence is more likely to be genuinely present in the sample than if the related sequences were not present.

In order to apply the formula to clusters of sequences, a phylogenetic tree can be created from the NGS sequence data. First a similarity score must be generated against each other member for the sequences between the primer sites. These scores are used to populate a similarity matrix. This matrix can be populated by using, as an example, the blast score resulting from an all-against-all blast searching. Next these data are used to produce clusters of sequences.

Figure 3B:
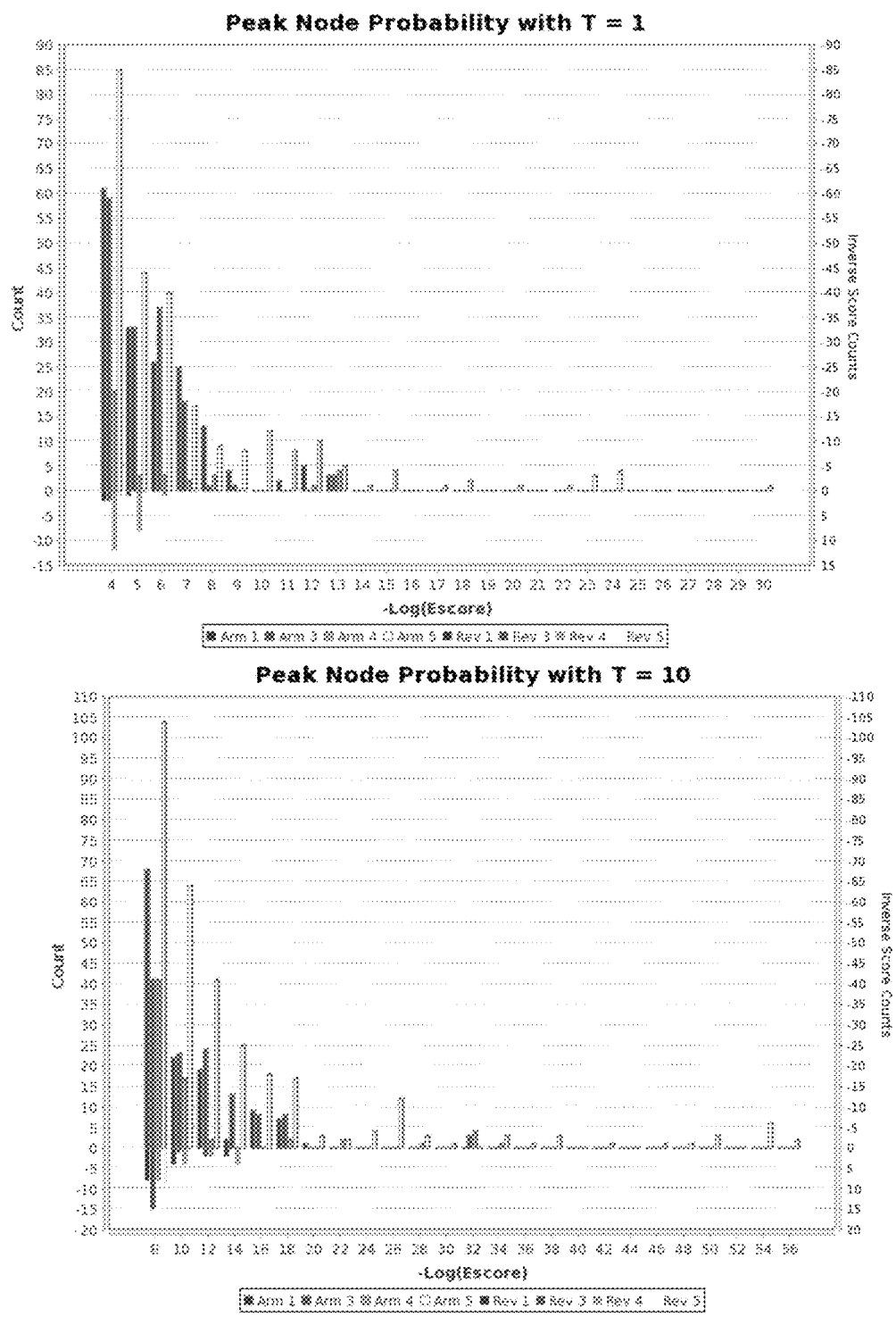
FIG. 3: Cluster based e-score analysis. (A) This figure shows the process of identifying peak nodes of statistical significance starting from barcoded NGS sequence data. (B) This figure shows histograms of the negative log of e-scores from the indicated experimental arm peak nodes on the upper Y axis, and the log inverse control scores in the lower Y axis. Experimental scores for experimental cohorts are indicated arm 1 . . . 5 and the inverse scores are indicated rev 1 . . . 5. The four graphs show the effects of different values of T from 1 to 1000 on the e-scores.
Figure 3B:
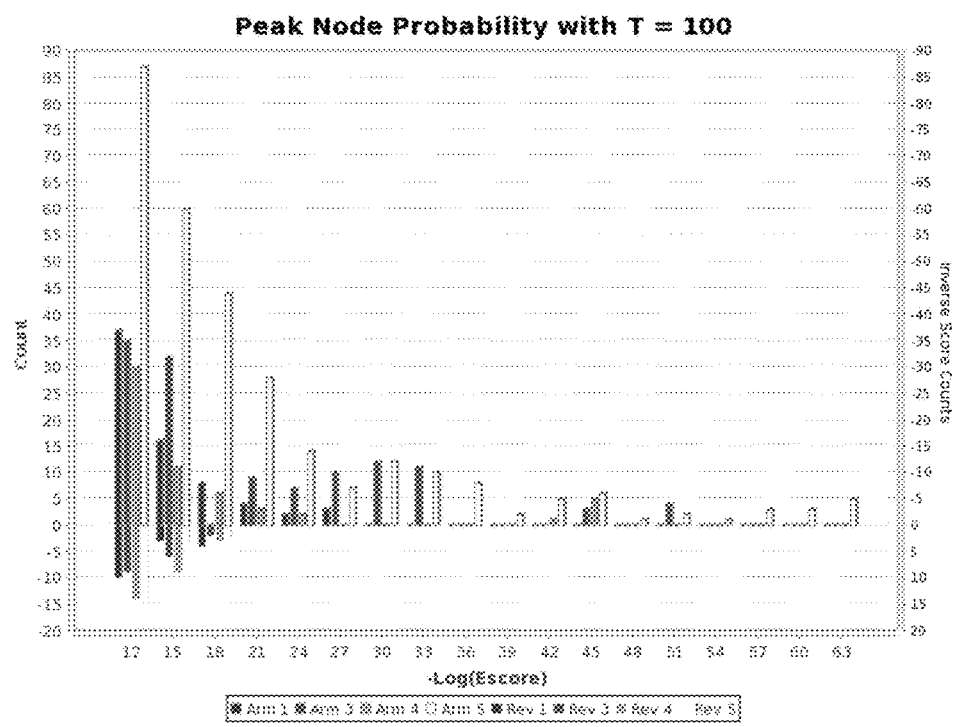
Figure 3B:
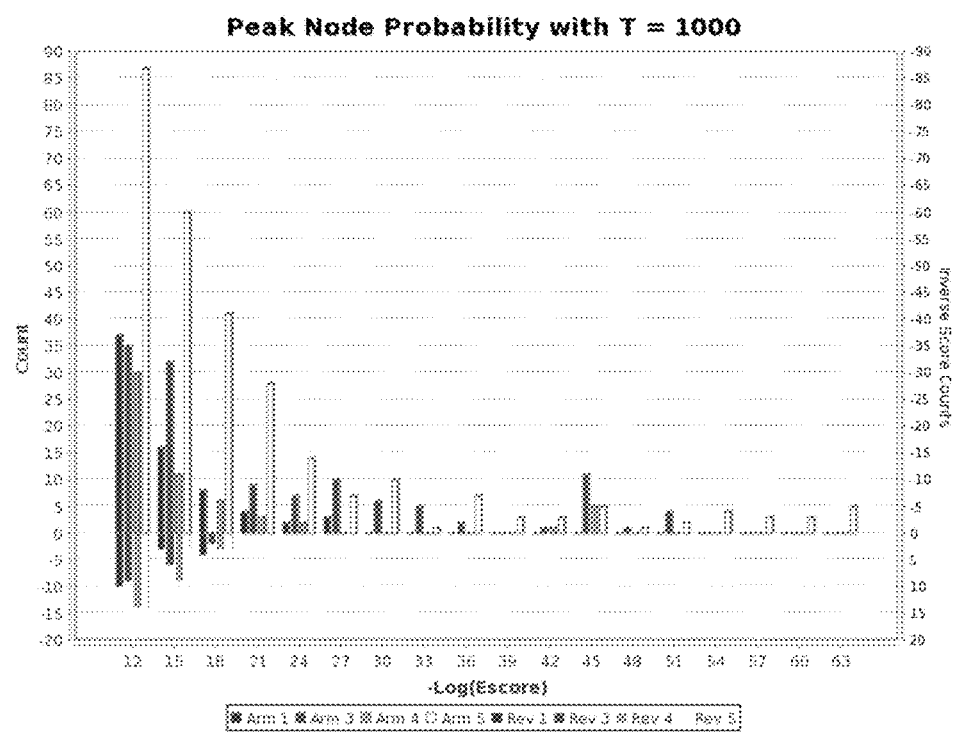

FIG. 3 summarizes the process of using NGS sequence data in creating the phylogenetic tree and assigning significance values to the leaf and node elements of the tree.

From the matrix data, a phylogenetic tree can be constructed using an agglomerative clustering algorithm such as Unweighted Pair Group Method with Arithmetic mean, (UPGMA). The expected formula E(n, m, Pa) can be applied to each node of the resulting tree, where the total events in the foreground or background are the sum of foreground or background events in the child nodes. This provides a straightforward statistical significance measure to sets of related sequences, rather than sequences measured one-by-one.

In order to divide the tree into significance-based subsets, peak nodes of e-scores in a given tree can be selected. A peak node is a node of the tree whose parent and child node's e-scores are less significant than its own. These represent local maximums in the tree graph, and the counts and significance of these nodes can be used to report overall differences between foreground and background sample sets.

How the raw count of a given sequence in a sample relates to the expected score formula depends on whether or not the events are independent. For example, if amplification of a sample by means such as non-linear PCR has the potential to favor one sequence over others, then counts of those sequences in a given sample would not be completely independent. If the events are totally dependent then one event would count the same as 100 events in a given PCR sample. On the other extreme, if the sequences are totally independent then each occurrence counts equally, whether one or 100 are detected in a sample. A generalization of the e-score formula is to limit the total counts allowed from a sample to a maximum number T. For example T=100 means that occurrences of sequences more than 100 times in a sample are not considered independent events, but less than 20 are. This parameter is T. FIG. 3B shows the effects of different values of T on significance scores of the 5 test arms described in the experimental method tested against naive controls. As an additional control for the calculation, the e-score of the background set against the foreground set can be calculated. In other words, by swapping the foreground with the background, the probability of sequence clusters being significant in the naive set as compared to the experiment set can be calculated. Graphed in the lower half of the graph are the scores for the corresponding inverse experiment which measures the probability of sequences from the naive arm being unique relative to the test arm. The presence of fewer of these scores and their lower significance indicate that most unique sets of sequences are present in the experimental sample set rather than the naive set. The presence of most of the very high probability specific sequences in experimental arms 3 and 5 correlates with the strongest immune response seen in those arms as measured by antigen blocking activity in the serum. This indicates that most of the sequences farther down the tree are produced in response to treatment as compared to the control samples. The likelihood of a given sequence in the set of being antigen-specific is extremely high.

Example 4

Light Chain Matching

Figure 4:
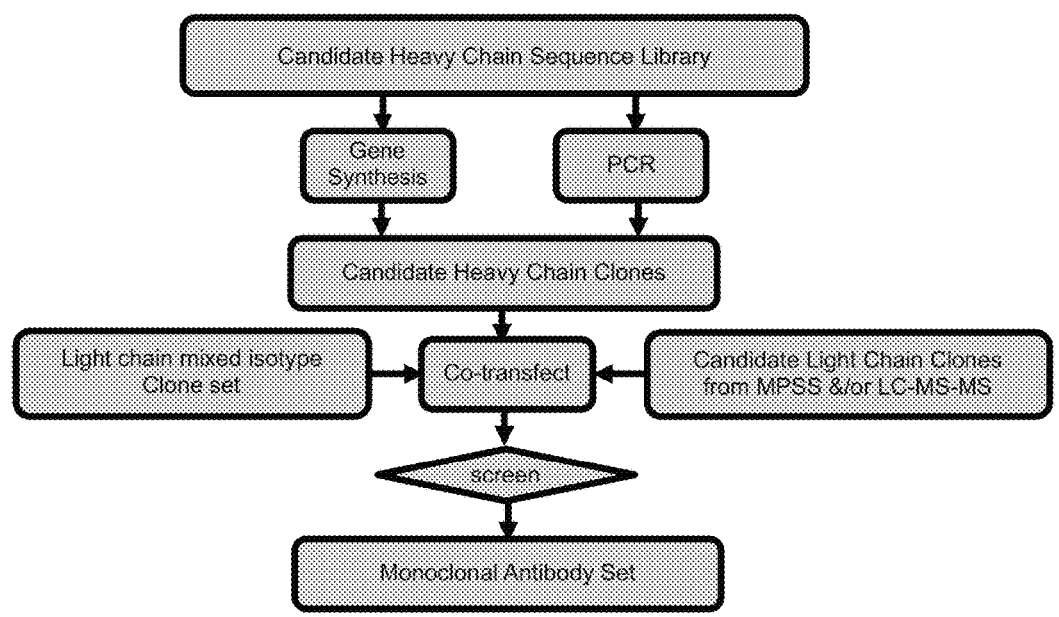
FIG. 4: Light Chain Pairing to Heavy Chain Sequence Library. This figure shows a method for pairing the heavy chain sequences with candidate light chain sequences in order to generate full length antibodies which are then expressed and screened for desired properties. The candidate light chain sequences can either be generated in a similar manner as the heavy chain candidate sequences, or deduced on the basis of isotypes that are known to frequently be paired with and to stabilize the isotype of the heavy chain candidate list.

Antibodies are paired dimers of heavy and light chain proteins. Therefore, in order to create a full monoclonal antibody, a light chain must be matched to the heavy chain. FIG. 4 illustrates several methods which can be used to accomplish this. Since light chains primarily contribute stability of binding to the antibody but not antigen specificity, candidate antigen specific heavy chains can be co-transfected with a limited set of light chain antibodies which can then be tested for binding against the target antigen. The set of light chain clones can be biased based on the isotype of the candidate heavy chain clones, since it is known that certain light chain isotypes are more likely than others to form stable high-affinity antibodies when combined with certain heavy chain isotypes. Efficient searching for a suitable light chain can be accomplished by co-transfection of multiple light chain clones with a single heavy chain, testing for antigen binding and once a high affinity antibody is found, deconvoluting the set of light chains with a second set of transfections with each of the light chains alone with the heavy chain.

Additionally one can perform MPSS on light chain sequences in the same manner as described above for heavy chain sequences. This would provide a set of candidate light chains which can be co-transfected with heavy chain sequences alone or in multiplexed combinations in order to find an optimal heavy and light chain pair. This would have the advantage of utilizing native light chain sequences specific for a particular adaptive immune state of an organism.

All of the data from each time point is desirable but not necessarily required for identification of candidate antibody sequences. The combined data processing algorithm takes into account various incomplete combinations of the data set.

Example 5

Experimental Data Set from Vaccinated Mice

Immunization

Mice were injected with a blood stage antigen from malaria in combination with four different adjuvant formulations, i.e., arms 1, 3, 4 and 5 of the experiment. Arm 1 was a base formulation while arms 3 and 5 were supplemented with Glycopyranosyl Lipid Adjuvant (GLA), and arms 4 and 5 were supplemented with Resiquimod (R-848). Each of these agents are agonists of Toll-Like Receptors (TLR). In addition samples from a naive control arm was harvested at each time point. Mice were given an initial injection followed by a primary boost at three weeks and a secondary boost at six weeks. cDNA samples were made from circulating blood cells taken on day 6 post-second boost of the adjuvant-antigen combination, and 4 weeks later from both circulating blood samples and bone marrow samples. Biochemical testing of serum taken post vaccination showed that arms 3 and 5 had the highest titer of antibodies with blocking activity of antigen to the host target protein.

Sequencing Sample Generation

Red blood cells in the samples were removed by osmotic lysis followed by washing in PBS. The remaining cells were lysed and used for cDNA synthesis onto oligo-dT coated magnetic beads. The polymerase used was SuperScript III, a highly processive engineered form of reverse transcriptase. A highly processive polymerase master mix, phusion flash, was used for the thermal cycling of the samples. These samples were used in six rounds of synthesis using just upstream primers after which the magnetic cDNA beads were removed by use of a magnetized sample tube holder. Then the 1 µl of the one-way reaction was placed in a 10 µl reaction with both upstream and downstream primers. This mixture was cycled for 18 rounds using a 10 second extension time. Three µl of each of these samples were added to a 30 µl fresh reaction mixture using the same primers and then cycled for an additional 18 rounds.

Primer Sets

PCR primer sets were designed to cover the Ig heavy chain locus of the mouse. First, a list of intact V region sequences with appropriate in-frame leader sequences was created by cross-referencing the Genbank record of the locus with references from the IMGT database. Upstream primer sets were designed to cover the list of V region. By combining together primer sets with a common 3' six base sequence, six pools of forward V region primers were created to cover the entire set of V regions. Two sets of reverse sequence primers were used, a single sequence which was sufficient to cover IgM constant region transcripts and a set of 3 needed to cover the IgG constant isotypes. The IgG reverse primers were also designed with identical 3' six base sequences, and used together in a single pool. The 5' most 8 bases of the primers were designed with a four letter bar-code on the 3' side. The combinations of the barcodes on the forward and reverse primers used on each sample was unique and enables identification of which sample the sequence was derived from. Final PCR reactions programmed from the same cDNA were pooled, and DNA was recovered using a Quiagen PCR cleanup column. The concentration of DNA in each sample was determined from 260/280 OD measurements and the samples were then mixed with equals amounts of DNA from each. This sample was used for library generation and sequencing using the Titanium 454 process.

The results shown in FIG. 3B was obtained by performing a run in a half-plate format and filtered to consider only IgG sequences.

Some portions of above description describe the aspects in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules can be embodied in software, firmware, hardware, or any combinations thereof.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A method for generating cDNA sequence libraries useful in producing monoclonal antibodies, the method comprising:
    generating a pre-immunized cDNA sequence library comprising cDNA sequences encoding proteins generated from a region subject to genomic rearrangement, wherein the region is an Ig heavy chain or light chain variable domain in a B-cell, or a T-cell alpha or beta variable domain in a T-cell, wherein the cDNA sequences are obtained from a first sample comprising lymphocytes of a host subject that has not been immunized with an antigen, wherein generating the pre-immunized cDNA sequence library comprises amplifying the cDNA sequences and sequencing the amplified cDNA sequences;
    generating an immunized cDNA sequence library comprising cDNA sequences encoding proteins generated from a region subject to genomic rearrangement, wherein the region is an Ig heavy chain or light chain variable domain in a B-cell, or a T-cell alpha or beta variable domain in a T-cell, wherein the cDNA sequences are obtained from a second sample comprising lymphocytes of said host subject after being immunized with said antigen, wherein generating the immunized cDNA sequence library comprises amplifying the cDNA sequences and sequencing the amplified cDNA sequences;
    analyzing the frequencies of occurrence of each of said pre-immunized and immunized set of cDNA sequences; and
    identifying candidate cDNA sequences useful in producing monoclonal antibodies from said pre-immunized and immunized libraries of cDNA sequences by comparing the frequency of occurrence in each library of cDNA sequences, wherein each candidate cDNA sequence is one which has a significantly higher frequency of occurrence in the immunized sample as compared to the frequency of occurrence in the pre-immunized sample.

2. The method of claim 1, wherein the lymphocytes comprise isolated B cells.

3. The method of claim 1, wherein the frequencies of occurrence of said pre-immunized and immunized cDNA sequence libraries are analyzed using a bioinformatics software algorithm.

4. The method of claim 1, wherein the host subject is an experimental animal.

5. The method of claim 4, wherein the host subject is a mouse.

6. The method of claim 4, wherein the host subject is a transgenic animal expressing human antibodies.

7. The method of claim 1, wherein the host subject is a human.

8. The method of claim 1, wherein the method further comprises bridge amplification of the pre-immunized and/or immunized cDNA sequences.

9. The method of claim 1, wherein the sequencing steps are performed by massively parallel sequencing.

* * * * *